US007659284B2

(12) United States Patent
Connolly et al.

(10) Patent No.: US 7,659,284 B2
(45) Date of Patent: Feb. 9, 2010

(54) THIAZOLOPYRIDINE KINASE INHIBITORS

(75) Inventors: Peter J. Connolly, New Providence, NJ (US); Sigmond G. Johnson, Flemington, NJ (US); Niranjan B. Pandey, Flemington, NJ (US); Steven A. Middleton, Flemington, NJ (US)

(73) Assignee: Janssen Pharmaceutica NV (BE)

( * ) Notice: Subject to any disclaimer, the term of this patent is extended or adjusted under 35 U.S.C. 154(b) by 316 days.

(21) Appl. No.: 11/226,961

(22) Filed: Sep. 15, 2005

(65) Prior Publication Data

US 2006/0058341 A1 Mar. 16, 2006

Related U.S. Application Data

(60) Provisional application No. 60/609,992, filed on Sep. 15, 2004.

(51) Int. Cl.
*A61K 31/4745* (2006.01)
*C07D 513/04* (2006.01)

(52) U.S. Cl. ........................ 514/301; 546/114

(58) Field of Classification Search ................ 546/114; 514/301
See application file for complete search history.

(56) References Cited

U.S. PATENT DOCUMENTS

| 4,880,916 | A | 11/1989 | Adam |
| 6,232,320 | B1 | 5/2001 | Stewart et al. |
| 6,452,014 | B1 | 9/2002 | Akama et al. |
| 6,579,882 | B2 | 6/2003 | Stewart et al. |
| 2001/0020030 | A1 | 9/2001 | Stewart et al. |
| 2002/0120144 | A1 | 8/2002 | Akama et al. |
| 2003/0220365 | A1 | 11/2003 | Stewart et al. |
| 2004/0058934 | A1 | 3/2004 | Carruthers et al. |
| 2004/0127395 | A1 | 7/2004 | Desai et al. |

FOREIGN PATENT DOCUMENTS

| DE | 285982 A5 | 10/1983 |
| WO | WO 98/02434 A2 | 1/1998 |
| WO | WO 02/051409 A1 | 7/2002 |
| WO | WO 03/040108 A1 | 5/2003 |
| WO | WO 2004/022060 A2 | 3/2004 |
| WO | WO 2004/046101 A2 | 6/2004 |

OTHER PUBLICATIONS

Wang X. et al., Nature, 2003, vol. 424, pp. 456-461.
Yeatman T.J., Nature Reviews Cancer, 2004, vol. 4(6), pp. 470-480.
Goldenberg-Furmanov M. et al., Cancer Research, 2004, 64, pp. 1058-1064.
Shah N. et al., Science, 2004, vol. 305, pp. 399-401.
Donato N. et al., Blood, 2003, 101(2), pp. 690-698.
V. L. Ivanov, V. A. Artemov, A. M. Shetopalov, V. N. Nesterov, Yu. T. Struchkov, and V. P. Litvinov, *2-Bromo-1-Phenylethylidenemalononitrile In The Synthesis of Thieno{3,2-b}Pyridines and Thiazolo{4,5-b}Pyridines*, Organic Synthesis, pp. 413-419, Mar. 1996.
Nabila A. Ismail, Fathy A. Khalifa, Reda M. Fekry and Yasser N. Abdel Azim, *Reactions with Cyanothioacetamide Derivatives: A New Route for The Synthesis of 2-Thiazolin-4-One, Thiazolo{4,5-b}Pyridine, Thiazolinonylpyrazole and Pyrano{2,3-d}-1,3-Thiazole Derivatives*, Phosphorus, Sulfur, and Silicon, 1992, vol. 66, pp. 29-35.
Nirupama Tiwari, Bandana Chaturvedi and Nizamuddin, *Synthesis and Fungicidal Activity of Some 3,7-Diaryl-6-Cyanorhodanino{4,5-b}-Pyridin-5 (AH)-Ones and 3-Arylrhodanino{4,5-b}Furan-6 (5H)-Ones*, Indian Journal of Chemistry, vol. 28B, Sep. 1989, pp. 796-798.
Mukhtar Hussain Khan, Raziul Haque, Ahmed Safi and Nizamuddin, *Synthesis and Insecticidal Activity of 5-Amino-7-Aryl-6-Cyano-3-Substituted-Thiazolo{4,5-b}-2,3,4,7-Tetrahydropyridine-2-Thione and 7-Aryl-6-Cyano-3-Substituted-2-Thioxo-Thiazolo {4,5-b}-2,3,4,5,6,7-Hexahydropyridin-5-One*, Indian Journal of Chemistry, vol. 37B, Oct. 1998, pp. 1069-1074.
V. A. Sodha, H. M. Hirpara, A. M. Trivedi, B. L. Khatri and A. R. Parikh, *Microwave Assisted Synthesis and Antimicrobial Activity of Some New Thiazolidinones*, Indian Journal of Chemistry, vol. 42B, Nov. 2003, pp. 2892-2895.
M. Seada, M. Abdel-Megid and I. M. El-Deen, *Synthesis and Biological Activity of Some New Thiazolidinones*, Indian Journal of Heterocyclic Chemistry, vol. 3, Oct.-Dec. 1993, pp. 81-86.
Rafat Milad Mohareb, Wagnat Wahba Wardakhan and Fawzia Zakeria El-Ablack, *The Reaction of Active Methylene Reagents with Sulfur and Phenyl Isothiocyanate: Novel Synthesis of Thiazole, Thiazolo{4,5-d}Pyrimidine and 4,5'-Bithiazolyl Derivatives*, J. Chem. Research, 1994, pp. 126-127.
Rafat M. Mohareb, Hoda Z. Shams and Yehia M. Elkholy, *Reactions of Phenyl Isothiocyanate and Sulfur with Dimeric Adducts: Novel Synthesis of Thiazoles, Thiazolo-{4,5-d}Pyrimidine and Thiazolo{4,5-d}-Pyridine Derivatives*, Phosphorus, Sulfur and Silicon, 1992, vol. 70, pp. 317-324.
Vasilii A. Artyomov, Vladimir L. Ivanov, Anatolii M. Shestopalov, Victor P. Litvinov, *2-Bromo-1-Arylethylidenemalononitriles-Convenient Reagents for The Regioselective Synthesis of Fused Pyridines*, Tetrahedron, Elsevier Science Ltd., vol. 53, No. 39, pp. 13351-13360, 1997.

(Continued)

*Primary Examiner*—Patricia L Morris

(57) ABSTRACT

The present invention is directed to novel thiazolopyridines, pharmaceutical compositions thereof, and the use thereof as inhibitors of ATP-protein kinase interactions. The thiazolopyridine compounds have the following Formula (I):

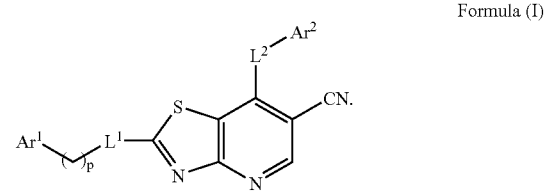

Formula (I)

13 Claims, No Drawings

OTHER PUBLICATIONS

Rafat M. Mohareb, Fatma A. Al-Omran, and Jonathan Z. Ho, *Reaction of 3-Cyano-2-Amino-4,5,6,7-Tetrahydrobenzo{b}Thiophene with Enaminonitriles,* Monatshefte fur Chemie Chemical Monthly, 133, 1443-1452, 2002.

Hussein F. Zohdi, Rafat M. Mohareb, and Wagnat W. Wardakhan, *Heterocyclic Synthesis with Isothiocyanate and Sulfur: A Novel Route for The Synthesis of Pyridino{2,3-d{Thiazole, Thiazolo{4',5':2,3}Pyridino{4,3-d}Pyridazine and Thiazolo{4,5-b}Isoquinoline Derivatives,* Phosphorous, Sulfur and Silicon, 1995, vol. 101, pp. 179-187.

Y. M. Elkholy and A. A. Elassar, *Enaminonitrile in Heterocyclic Synthesis: Synthesis of Thiazolo{4,5-b}Pyridine and Thiazolo{4,5-d}Pyrimidine Derivatives,* Egypt. J. Chem. 38, No. 1, pp. 67-76 (1995).

Fawzia Zakeria El-Ablack, *Synthesis of Some New Thiazole Derivatives of Pharmaceutical Interest,* Boll, Chim, Farmac.-Anno 142- p. 406-409, Nov. 2003.

Ahmed Kamal, El-Shafei, Ahmed Mahmoud El Sayed, Adel Sultan and Hossam Abdel-Ghany, *Application of Phase-Transfer Catalysis in Reactions with Some Rhodanine Derivatives,* Gazzetta Chimica Italiana, 120, 1990.

S. M. Sayed, *Nitriles in Heterocyclic Synthesis: Reactivity of 2-(Benzothiazol-1-ylmethyl)1,3-Thiazol-4(5H)-One Towards α, β-Unsaturated Nitriles,* Journal of the Chinese chemical Society, 2003, 50, 1081-1073.

Klaus Hartke and Gunter Golz, *Schwefelheterocyclen Durch Thioacylierung,* Liebigs Ann. Chem. 1973, pp. 1644-1651.

IUPAC Recommendations for Fundamental Stereochemistry (Section E), Pure Appl. Chem., 1976, 45:13-30.

Mitsuru Shiraishi, et al., *J. Med. Chem.*, 2000, 43, 2049-2063.

Far AR, Cho Yl, Rang A, Rudkewich DM, Rebek J, *Tetrahedron,* 2002, 58(4), 741-756.

THIAZOLOPYRIDINE KINASE INHIBITORS

CROSS REFERENCE TO RELATED APPLICATIONS

This present application claims benefit of U.S. Provisional Patent Application Ser. No. 60/609,992, filed Sep. 15, 2004, which is incorporated herein by reference in its entirety and for all purposes.

FIELD OF THE INVENTION

The present invention is in the area of novel thiazolopyridines and pharmaceutically acceptable forms thereof, their syntheses, and their use as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR-α, PDGFR-β, Tie-1, Tie-2 (also Tek-1 or Tek), VEGFRI (also FLT-1), VEGFR2 (also KDR), FLT-3, FLT-4, c-KIT, JAKI, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (I-IV), CamKK, Chk1 and 2 (Checkpoint kinases), CKI, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 (A and B), PKA, P38, Erk (1-3), PKB (including all PKB subtypes) (also AKT-1, AKT-2, AKT-3 or AKT3-1), IRAK1, FRK, SGK, TAK1 or Tpl-2 (also COT).

Protein kinases play very important roles in the normal regulation of cell growth. However, as a result of either mutation or overexpression of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Uncontrolled signaling for cell growth due to defective control of protein phosphorylation has also been implicated in a number of diseases and disease conditions, such as osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus CMV), heart disease (such as atherosclerosis, neointima formation or transplantation-induced vasculopathies (such as restenosis and the like), lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like). Therefore, kinase inhibitors have potential use as therapeutic agents.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

The epidermal growth factor receptor (EGFR) tyrosine-kinase family includes the receptors EGFR (also referred to as EGFR-1 or Erb-B1), HER-2 (or neu), EGFR3 and EGFR4. Epidermal Growth Factor (EGF), Transforming Growth Factor-α (TGF-α) and the HER-2 ligand heregulin are three of the ligands that bind to the EGFR receptors.

For example, EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs. Diseases associated with increased EGFR expression include proliferative glomerulonephritis, diabetes-induced renal disease and chronic pancreatitis. Overexpression of HER2 has been associated with breast and ovarian cancer. Diseases associated with the overproduction of TGF-α, rather than overexpression of EGFR, include psoriasis, a cell-proliferative skin disorder. Since EGFR expression levels in uterine tissues are elevated during implantation of a fertilized egg, an EGFR inhibitor may also have potential use as a contraceptive to reduce fertility.

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG1478 has been shown to reduce the viral load in cells that were infected in the presence of the tyrphostin (Wang, et al., Nature, 24 Jul. 2003, Vol 424). Accordingly, potent EGFR selective inhibitors may be useful in anti-CMV therapy.

The Src family of tyrosine-kinases includes the sub-family proteins c-Src, Lyn, Fyn, Lck, Syk, Hck, Yes, Blk, Fgr and Frk. While various members of the c-Src family are important for normal cellular proliferation, their overexpression and overactivation can promote development of cancer (Yeatman T J, Nature, June 2004, Vol. 4). For example, the Lyn kinase has been shown to be upregulated in hormone resistant prostate cancer. Tumor xenografts of hormone resistant prostate cancer cells showed delayed growth upon treatment with peptides that specifically block Lyn kinase activity (Goldenberg-Furmanov, et al., Cancer Research, 1 Feb. 2004, 64, 1058-1064).

The Lyn and Hck Src sub-family tyrosine-kinases have both been implicated in chronic myeloid leukemia (CML). CML is caused by the BCR-Abl fusion protein that results from the t(9;22) chromosomal translocation that juxtaposes the c-Abl non-receptor tyrosine kinase gene on chromosome 9 with a breakpoint cluster region (bcr) gene on chromosome 22. The BCR-Abl fusion protein is a constitutively activated form of the Abl tyrosine kinase that drives uncontrolled growth leading to CML and many cases of adult acute lymphoblastic leukemia. Gleevec, which is an inhibitor of Abl has been successfully used to treat CML. However, Gleevec does not help patients in blast crisis because they carry mutant forms of BCR-Abl that no longer bind Gleevec. Such Gleevec resistant CML cells are sensitive to a dual src/BCR-Abl inhibitor that binds and inhibits the mutant BCR-Abl and members of the src family (Shah, et al., Science, 16 Jul. 2004, Vol 305, 399-401). There are also other ways that CML cells can become resistant to treatment with the tyrosine kinase Abl inhibitor Gleevec. For example, CML K562 cells that become resistant to Gleevec minimize reliance on the BCR-Abl translocation for growth and instead upregulate the Lyn and Hck kinases. This was demonstrated by expressing antisense Lyn in these cells, which reduced their rate of proliferation (Donato, et al., Blood, 15 Jan. 2003, 101(2)). c-Src and other Src family members are also involved in cellular adhesion, invasion and motility of tumor cells. Thus, small molecule inhibitors of the Src kinase family could offer new therapeutic opportunities for both leukemias and solid tumors.

U.S. Pat. Nos. 6,232,320 and 6,579,882 and U.S. Patent Application Publication Nos. 20010020030 and 2003220365 describe compounds for treating inflammation.

SUMMARY OF THE INVENTION

A first aspect of the present invention is directed to novel compounds of Formula (I).

A second aspect of the present invention is directed to pharmaceutical compositions comprising at least one compound of Formula (I), or a pharmaceutically acceptable form thereof and one or more pharmaceutically acceptable excipients.

A third aspect of the present invention is directed to a method of inhibiting the activity of a protein kinase, comprising contacting the protein kinase domain with one or more compounds of Formula (I).

A fourth aspect of the invention is directed to a method of inhibiting unregulated kinase activity comprising administering to an animal a composition comprising a pharmaceutically effective amount of at least one compound of Formula (I), or a pharmaceutically acceptable form thereof and one or more pharmaceutically-acceptable excipients.

A fifth aspect of the present invention is directed to a method of inhibiting increased or unregulated kinase expression or signaling comprising administering to an animal a pharmaceutically effective amount of at least one compound of Formula (I), or a pharmaceutically acceptable form thereof and one or more pharmaceutically-acceptable excipients.

A sixth aspect of the present invention is directed to a method of treating diseases or conditions caused by increased kinase expression or signaling leading to unregulated cell proliferation comprising administering to an animal a pharmaceutically effective amount of at least one compound of Formula (I), or a pharmaceutically acceptable form thereof and one or more pharmaceutically-acceptable excipients.

A seventh aspect of the present invention is directed to a method of treating cancer comprising administering to an animal a pharmaceutically effective amount of at least one compound of Formula (I), or a pharmaceutically acceptable form thereof and one or more pharmaceutically-acceptable excipients.

An eighth aspect of the present invention is directed to describing thiazolopyridine derivatives as inhibitors of a tyrosine-kinase selected from EGFR, HER-2, c-Src, Lyn, Abl and the like.

A ninth aspect of the present invention is to describe thiazolopyridine derivatives that are useful at low dosages as inhibitors of protein kinase-induced mitogenesis. This therefore leads to a further aspect of compounds having extremely low cytotoxicity.

A tenth aspect of the present invention is to describe thiazolopyridine derivatives that are useful in suppressing tumors, especially tumors such as non-small-cell lung cancers, colon cancers, breast cancers and the like where mitogenesis is heavily driven by protein kinases such as EGFR, HER-2, c-Src, Lyn and the like.

An eleventh aspect of the present invention is to describe thiazolopyridine derivatives that have utility as chronic therapeutic agents for inhibiting protein kinase-induced responses. This therefore leads to a further aspect of such therapeutic agents being used as a long-term therapy for inducing cancer remission.

A twelfth aspect of the present invention is to describe thiazolopyridine derivatives that have utility as therapeutic agents against chronic or acute diseases characterized by uncontrolled cell proliferation and which may result in metastatic cancer cell invasion and migration.

A thirteenth aspect of the present invention is to describe thiazolopyridine derivatives that have utility as therapeutic agents against EGFR protein kinase mediated cytomegalovirus (CMV) infection.

A fourteenth aspect of the present invention is to describe thiazolopyridine derivatives that have utility as therapeutic agents against chronic or acute kinase mediated diseases or for use as a contraceptive agent.

A fifteenth aspect of the present invention is directed to methods of synthesizing compounds of Formula (I).

These and other aspects and advantages of the invention, which will become apparent in light of the detailed description below, are achieved through use of the compounds of this invention.

DETAILED DESCRIPTION OF THE INVENTION

The present invention provides a substituted thiazolopyridine compound of Formula (I)

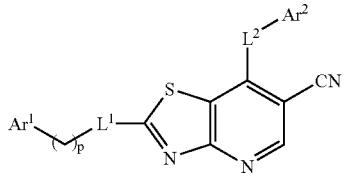

Formula (I)

and pharmaceutically acceptable forms thereof, wherein
L$^1$ is selected from the group consisting of S(C$_{1-4}$alkyl), a bond, N(R$_1$), N(R$_1$)C(O) and C(O)N(R$_1$), wherein R$_1$ is selected from the group consisting of hydrogen, C$_{1-8}$alkyl and C$_{1-8}$alkyl(C$_{1-8}$alkoxy);
p is 0, 1, 2, 3 or 4;
L$^2$ is selected from the group consisting of O, S, N(R$_1$) and a bond;
Ar$^1$ is selected from the group consisting of aryl, heteroaryl, benzofused heteroaryl, heterocyclyl and benzofused heterocyclyl optionally substituted with from one to three substituents independently selected from the group consisting of
(1) C$_{1-8}$alkyl,
(2) C$_{2-8}$alkenyl,
(3) C$_{2-8}$alkynyl,
(4) C$_{1-8}$alkoxy,
  wherein (1), (2), (3) and (4) are optionally substituted with one to three substituents independently selected from the group consisting of
  (i) C$_{3-8}$cycloalkyl,
  (ii) aryl,
  (iii) heteroaryl,
  (iv) heterocyclyl,
    wherein (i), (ii), (iii) and (iv) are optionally substituted with from one to three substituents independently selected from the group consisting of
    (a) C$_{1-8}$alkyl,
    (b) C$_{1-8}$alkoxy,
    (c) C$_{1-8}$alkyl(C$_{1-8}$alkoxy),
    (d) C$_{1-8}$alkyl(halogen)$_{1-3}$,
    (e) C$_{1-8}$alkyl(hydroxy)$_{1-3}$,
    (f) CO$_2$(C$_{1-8}$alkyl),
    (g) amino optionally mono or disubstituted with C$_{1-8}$alkyl,
    (h) cyano,
    (i) halogen,
    (j) hydroxy,
    (k) C$_{1-8}$alkyl(amino) optionally mono or disubstituted on amino with C$_{1-8}$alkyl,
    (l) C$_{3-8}$cycloalkyl,
    (m) C$_{1-8}$alkyl(C$_{3-8}$cycloalkyl),
    (n) heterocyclyl optionally substituted with one or two C$_{1-8}$alkyl substituents, and
    (o) C$_{1-8}$alkyl(heterocyclyl) optionally substituted on heterocyclyl with one or two C$_{1-8}$alkyl substituents, and
  (v) amino optionally mono or disubstituted with a substituent independently selected from the group consisting of
    (a) C$_{1-8}$alkyl,
    (b) C$_{1-8}$alkyl(C$_{1-8}$alkoxy),
    (c) C$_{1-8}$alkyl(hydroxy)$_{1-3}$,
    (d) C$_{3-8}$cycloalkyl,
    (e) heterocyclyl optionally substituted with one or two C$_{1-8}$alkyl substituents, and
    (f) C$_{1-8}$alkyl(heterocyclyl) optionally substituted on heterocyclyl with one or two C$_{1-8}$alkyl substituents,
(5) amino optionally mono or disubstituted with a substituent independently selected from the group consisting of
  (i) C$_{1-8}$alkyl,
  (ii) C$_{1-8}$alkyl(C$_{1-8}$alkoxy),
  (iii) C$_{1-8}$alkyl(amino) optionally mono or disubstituted on amino with C$_{1-8}$alkyl,
  (iv) C$_{1-8}$alkyl(hydroxy)$_{1-3}$,
  (v) C$_{3-8}$cycloalkyl,
  (vi) heterocyclyl optionally substituted with one or two C$_{1-8}$alkyl substituents, and
  (vii) C$_{1-8}$alkyl(heterocyclyl) optionally substituted on heterocyclyl with one or two C$_{1-8}$alkyl substituents,
(6) cyano,
(7) halogen,
(8) hydroxy,
(9) C$_{3-8}$cycloalkyl,
(10) aryl,
(11) heteroaryl,
(12) heterocyclyl,
(13) oxy substituted with a substituent selected from the group consisting of
  (i) CF$_3$,
  (ii) C$_{3-8}$cycloalkyl,
  (iii) aryl,
  (iv) heteroaryl, and
  (v) heterocyclyl,
(14) SO$_2$(heterocyclyl) optionally substituted on heterocyclyl with one or two C$_{1-8}$alkyl substituents,
(15) C(O) substituted with a substituent selected from the group consisting of
  (i) hydrogen,
  (ii) hydroxy,
  (iii) C$_{1-8}$alkyl,
  (iv) C$_{1-8}$alkoxy, and
  (v) amino optionally mono or disubstituted with a substituent independently selected from the group consisting of
    (a) C$_{1-8}$alkyl,
    (b) C$_{1-8}$alkyl(C$_{1-8}$alkoxy),
    (c) C$_{1-8}$alkyl(amino) optionally mono or disubstituted on amino with C$_{1-8}$alkyl,
    (d) C$_{1-8}$alkyl(hydroxy)$_{1-3}$,
    (e) C$_{1-8}$alkyl(heterocyclyl) optionally substituted on heterocyclyl with one or two C$_{1-8}$alkyl substituents,
    (f) C$_{3-8}$cycloalkyl, and
    (g) aryl; and
(16) SO$_2$(amino), wherein amino is optionally mono or disubstituted with a substituent independently selected from the group consisting of
  (i) C$_{1-8}$alkyl,
  (ii) C$_{1-8}$alkyl(C$_{1-8}$alkoxy),
  (iii) C$_{1-8}$alkyl(amino) optionally mono or disubstituted on amino with C$_{1-8}$alkyl,
  (iv) C$_{1-8}$alkyl(hydroxy)$_{1-3}$,
  (v) C$_{1-8}$alkyl(heterocyclyl) optionally substituted on heterocyclyl with one or two C$_{1-8}$alkyl substituents,
  (vi) C$_{3-8}$cycloalkyl, and
  (vii) aryl; and
Ar$^2$ is selected from the group consisting of aryl, heteroaryl, benzofused heteroaryl, heterocyclyl and benzofused heterocyclyl optionally substituted with from one to three substituents independently selected from the group consisting of (1) $C_{1-8}$alkyl,
(2) $C_{2-8}$alkenyl,
(3) $C_{2-8}$alkynyl,
(4) $C_{1-8}$alkoxy,
  wherein (1), (2), (3) and (4) are optionally substituted with from one to three substituents independently selected from the group consisting of
  (i) $C_{1-8}$alkoxy,
  (ii) cyano,
  (iii) halogen,
  (iv) hydroxy,
  (v) $C_{3-8}$cycloalkyl,
  (vi) aryl,
  (vii) heteroaryl,
  (viii) heterocyclyl,
    wherein (v), (vi), (vii) and (viii) are optionally substituted with from one to three substituents independently selected from the group consisting of
    (a) $C_{1-8}$alkyl,
    (b) $C_{1-8}$alkoxy,
    (c) $C_{1-8}$alkyl($C_{1-8}$alkoxy),
    (d) amino optionally mono or disubstituted with $C_{1-8}$alkyl,
    (e) cyano,
    (f) halogen,
    (g) $C_{1-8}$alkyl(halogen)$_{1-3}$,
    (h) hydroxy,
    (i) $C_{1-8}$alkyl(hydroxy)$_{1-3}$,
    (j) $C_{3-8}$cycloalkyl, and
    (k) heterocyclyl optionally substituted with one or two $C_{1-8}$alkyl substituents,
  (ix) amino optionally mono or disubstituted with a substituent independently selected from the group consisting of
    (a) $C_{1-8}$alkyl,
    (b) $C_{1-8}$alkyl($C_{1-8}$alkoxy),
    (c) $C_{1-8}$alkyl(hydroxy)$_{1-3}$,
    (d) $C_{3-8}$cycloalkyl,
    (e) heterocyclyl optionally substituted with one or two $C_{1-8}$alkyl substituents, and
    (f) $C_{1-8}$alkyl(heterocyclyl) optionally substituted on heterocyclyl with one or two $C_{1-8}$alkyl substituents, and
  (x) C(O)amino optionally mono or disubstituted with a substituent independently selected from the group consisting of
    (a) $C_{1-8}$alkyl,
    (b) $C_{1-8}$alkyl($C_{1-8}$alkoxy),
    (c) $C_{1-8}$alkyl(hydroxy)$_{1-3}$,
    (d) $C_{3-8}$cycloalkyl,
    (e) aryl optionally substituted with one to three halogen substituents,
    (f) heterocyclyl optionally substituted with one or two $C_{1-8}$alkyl substituents, and
    (g) $C_{1-8}$alkyl(heterocyclyl) optionally substituted on heterocyclyl with one or two $C_{1-8}$alkyl substituents,
(5) amino optionally mono or disubstituted with a substituent independently selected from the group consisting of
  (i) $C_{1-8}$alkyl,
  (ii) $C_{1-8}$alkyl($C_{1-8}$alkoxy),
  (iii) $C_{1-8}$alkyl(amino) optionally mono or disubstituted on amino with $C_{1-8}$alkyl,
  (iv) $C_{1-8}$alkyl(hydroxy)$_{1-3}$,
  (v) $C_{3-8}$cycloalkyl,
  (vi) heterocyclyl optionally substituted with one or two $C_{1-8}$alkyl substituents, and
  (vii) $C_{1-8}$alkyl(heterocyclyl) optionally substituted on heterocyclyl with one or two $C_{1-8}$alkyl substituents,
(6) oxy substituted with a substituent selected from the group consisting of
  (i) $C_{3-8}$cycloalkyl,
  (ii) aryl,
  (iii) heteroaryl, and
  (iv) heterocyclyl,
    wherein (i), (ii), (iii) and (iv) are optionally substituted with from one to three substituents independently selected from the group consisting of
    (a) $C_{1-8}$alkyl,
    (b) $C_{1-8}$alkoxy,
    (c) $C_{1-8}$alkyl($C_{1-8}$alkoxy),
    (d) amino optionally mono or disubstituted with $C_{1-8}$alkyl, and
    (e) halogen,
(7) C(O) substituted with a substituent independently selected from the group consisting of
  (i) hydrogen,
  (ii) $C_{1-8}$alkyl optionally substituted with from one to three substituents independently selected from the group consisting of
    (a) cyano,
    (b) halogen, and
    (c) hydroxy,
  (iii) $C_{1-8}$alkoxy,
  (iv) hydroxyl, and
  (v) $C_{1-8}$alkoxy($C_{1-8}$alkoxy),
(8) cyano,
(9) halogen,
(10) hydroxy,
(11) nitro,
(12) $C_{3-8}$cycloalkyl,
(13) aryl,
(14) heteroaryl,
(15) benzofused heteroaryl,
(16) heterocyclyl, and
(17) benzofused heterocyclyl;
  wherein (12)-(17) are optionally substituted with one or two substituents independently selected from the group consisting of
  (i) $C_{3-8}$cycloalkyl,
  (ii) $C_{1-8}$alkyl($C_{3-8}$cycloalkyl),
  (iii) aryl,
  (iv) $C_{1-8}$alkyl(aryl),
  (v) heteroaryl,
  (vi) $C_{1-8}$alkyl(heteroaryl),
  (vii) heterocyclyl, and
  (viii) $C_{1-8}$alkyl(heterocyclyl).

An example of a compound of Formula (I) is a compound wherein $L^1$ is selected from the group consisting of $N(R_1)$, wherein $R_1$ is selected from the group consisting of hydrogen, $C_{1-8}$alkyl and $C_{1-8}$alkyl($C_{1-8}$alkoxy).

An example of a compound of Formula (I) is a compound wherein $L^1$ is NH.

An example of a compound of Formula (I) is a compound wherein p is 0, 1, 2 or 3.

An example of a compound of Formula (I) is a compound wherein $L^2$ is selected from the group consisting of O, S and $N(R_1)$.

An example of a compound of Formula (I) is a compound wherein $L^2$ is selected from the group consisting of O, S and NH.

An example of a compound of Formula (I) is a compound wherein $Ar^1$ is selected from the group consisting of aryl, heteroaryl and heterocyclyl, each optionally substituted with from one to three substituents independently selected from the group consisting of (1) $C_{1-8}$alkyl,
(2) $C_{1-8}$alkoxy,
   wherein (1) and (2) are optionally substituted with one to three substituents independently selected from the group consisting of
   (i) $C_{3-8}$cycloalkyl,
   (ii) aryl,
   (iii) heteroaryl,
   (iv) heterocyclyl,
      wherein (i), (ii), (iii) and (iv) are optionally substituted with from one to three substituents independently selected from the group consisting of
      (a) $C_{1-8}$alkyl,
      (b) $C_{1-8}$alkoxy,
      (c) $C_{1-8}$alkyl($C_{1-8}$alkoxy),
      (d) $C_{1-8}$alkyl(halogen)$_{1-3}$,
      (e) $C_{1-8}$alkyl(hydroxy)$_{1-3}$,
      (f) amino optionally mono or disubstituted with $C_{1-8}$alkyl,
      (g) cyano,
      (h) halogen,
      (i) hydroxy, and
      (j) $C_{1-8}$alkyl(amino) optionally mono or disubstituted on amino with $C_{1-8}$alkyl, and
   (v) amino optionally mono or disubstituted with a substituent independently selected from the group consisting of
      (a) $C_{1-8}$alkyl,
      (b) $C_{1-8}$alkyl($C_{1-8}$alkoxy),
      (c) heterocyclyl optionally substituted with one or two $C_{1-8}$alkyl substituents, and
      (d) $C_{1-8}$alkyl(heterocyclyl) optionally substituted on heterocyclyl with one or two $C_{1-8}$alkyl substituents,
(3) amino optionally mono or disubstituted with a substituent independently selected from the group consisting of
   (i) $C_{1-8}$alkyl,
   (ii) $C_{1-8}$alkyl(amino) optionally mono or disubstituted on amino with $C_{1-8}$alkyl,
   (iii) heterocyclyl optionally substituted with one or two $C_{1-8}$alkyl substituents, and
   (iv) $C_{1-8}$alkyl(heterocyclyl) optionally substituted on heterocyclyl with one or two $C_{1-8}$alkyl substituents,
(4) halogen,
(5) hydroxy,
(6) $C_{3-8}$cycloalkyl,
(7) aryl,
(8) heteroaryl,
(9) heterocyclyl, and
(10) SO$_2$(amino), wherein amino is optionally mono or disubstituted with a substituent independently selected from the group consisting of
   (i) $C_{1-8}$alkyl,
   (ii) $C_{1-8}$alkyl($C_{1-8}$alkoxy),
   (iii) $C_{1-8}$alkyl(amino) optionally mono or disubstituted on amino with $C_{1-8}$alkyl,
   (iv) $C_{1-8}$alkyl(hydroxy)$_{1-3}$, and
   (v) $C_{1-8}$alkyl(heterocyclyl) optionally substituted on heterocyclyl with one or two $C_{1-8}$alkyl substituents.

An example of a compound of Formula (I) is a compound wherein Ar$^1$ is selected from the group consisting of aryl, heteroaryl and heterocyclyl, each optionally substituted with from one to three substituents independently selected from the group consisting of
(1) $C_{1-8}$alkyl,
(2) $C_{1-8}$alkoxy,
   wherein (1) and (2) are optionally substituted with one to three substituents independently selected from the group consisting of
   (i) heteroaryl, and
   (ii) heterocyclyl,
      wherein (i) and (ii) are optionally substituted with from one to three substituents independently selected from the group consisting of
      (a) $C_{1-8}$alkyl,
      (b) $C_{1-8}$alkyl(hydroxy), and
      (c) amino, and
   (iii) amino optionally mono or disubstituted with a substituent independently selected from the group consisting of
      (a) $C_{1-8}$alkyl,
      (b) $C_{1-8}$alkyl($C_{1-8}$alkoxy),
      (c) heterocyclyl, and
      (d) $C_{1-8}$alkyl(heterocyclyl),
(3) amino optionally mono or disubstituted with a substituent independently selected from the group consisting of
   (i) $C_{1-8}$alkyl(amino), and
   (ii) $C_{1-8}$alkyl(heterocyclyl),
(4) halogen,
(5) hydroxy,
(6) heterocyclyl, and
(7) SO$_2$(amino), wherein amino is optionally mono or disubstituted with a substituent independently selected from the group consisting of
   (i) $C_{1-8}$alkyl($C_{1-8}$alkoxy),
   (ii) $C_{1-8}$alkyl(amino) optionally mono or disubstituted on amino with $C_{1-8}$alkyl, and
   (iii) $C_{1-8}$alkyl(heterocyclyl), An example of a compound of Formula (I) is a compound wherein Ar$^2$ is selected from the group consisting of aryl and heterocyclyl, each optionally substituted with from one to three substituents independently selected from the group consisting of
(1) $C_{1-8}$alkyl,
(2) $C_{2-8}$alkenyl,
(3) $C_{2-8}$alkynyl,
(4) $C_{1-8}$alkoxy,
   wherein (1), (2), (3) and (4) are optionally substituted with from one to three substituents independently selected from the group consisting of
   (i) $C_{1-8}$alkoxy,
   (ii) halogen,
   (iii) hydroxy,
   (iv) aryl optionally substituted with from one to three substituents independently selected from the group consisting of
      (a) $C_{1-8}$alkyl,
      (b) $C_{1-8}$alkoxy,
      (c) $C_{1-8}$alkyl($C_{1-8}$alkoxy),
      (d) amino optionally mono or disubstituted with $C_{1-8}$alkyl,
      (e) halogen,
      (f) $C_{1-8}$alkyl(halogen)$_{1-3}$,
      (g) hydroxy, and
      (h) $C_{1-8}$alkyl(hydroxy)$_{1-3}$, and
   (v) amino optionally mono or disubstituted with $C_{1-8}$alkyl,
(5) amino optionally mono or disubstituted with a substituent independently selected from the group consisting of
   (i) $C_{1-8}$alkyl, and
   (ii) $C_{1-8}$alkyl(amino) optionally mono or disubstituted on amino with $C_{1-8}$alkyl,
(6) oxy substituted with a substituent selected from the group consisting of
   (i) $C_{3-8}$cycloalkyl,
   (ii) aryl, (iii) heteroaryl, and
(iv) heterocyclyl,
wherein (i), (ii), (iii) and (iv) are optionally substituted with from one to three substituents independently selected from the group consisting of
(a) $C_{1-8}$alkyl,
(b) $C_{1-8}$alkoxy,
(c) amino optionally mono or disubstituted with $C_{1-8}$alkyl, and
(d) halogen,
7) cyano,
8) halogen, and
9) hydroxy.

An example of a compound of Formula (I) is a compound wherein $Ar^2$ is selected from the group consisting of aryl and heterocyclyl, each optionally substituted with from one to three substituents independently selected from the group consisting of
1) $C_{2-8}$alkynyl,
(2) $C_{1-8}$alkoxy optionally substituted with from one to three substituents independently selected from the group consisting of
(i) halogen, and
(ii) aryl optionally substituted with from one to three halogen substituents,
(3) oxyaryl optionally substituted with from one to three substituents independently selected from the group consisting of
(i) $C_{1-8}$alkyl,
(ii) $C_{1-8}$alkoxy,
(iii) amino optionally mono or disubstituted with $C_{1-8}$alkyl, and
(iv) halogen, and
(4) halogen.

An example of a compound of Formula (I) is a compound wherein
$L^1$ is NH;
p is 0, 1, 2 or 3;
$L^2$ is selected from the group consisting of O, S and NH;
$Ar^1$ is selected from the group consisting of aryl, heteroaryl and heterocyclyl, each optionally substituted with from one to three substituents independently selected from the group consisting of
(1) $C_{1-8}$alkyl,
(2) $C_{1-8}$alkoxy,
wherein (1) and (2) are optionally substituted with one to three substituents independently selected from the group consisting of
(i) heteroaryl, and
(ii) heterocyclyl,
wherein (i) and (ii) are optionally substituted with from one to three substituents independently selected from the group consisting of
(a) $C_{1-8}$alkyl,
(b) $C_{1-8}$alkyl(hydroxy), and
(c) amino, and
(iii) amino optionally mono or disubstituted with a substituent independently selected from the group consisting of
(a) $C_{1-8}$alkyl,
(b) $C_{1-8}$alkyl($C_{1-8}$alkoxy),
(c) heterocyclyl, and
(d) $C_{1-8}$alkyl(heterocyclyl),
(3) amino optionally mono or disubstituted with a substituent independently selected from the group consisting of
(i) $C_{1-8}$alkyl(amino), and
(ii) $C_{1-8}$alkyl(heterocyclyl),
(4) halogen,
(5) hydroxy,
(6) heterocyclyl, and
(7) $SO_2$(amino), wherein amino is optionally mono or disubstituted with a substituent independently selected from the group consisting of
(i) $C_{1-8}$alkyl($C_{1-8}$alkoxy),
(ii) $C_{1-8}$alkyl(amino) optionally mono or disubstituted on amino with $C_{1-8}$alkyl, and
(iii) $C_{1-8}$alkyl(heterocyclyl); and
$Ar^2$ is selected from the group consisting of aryl and heterocyclyl, each optionally substituted with from one to three substituents independently selected from the group consisting of
(1) $C_{2-8}$alkynyl,
(2) $C_{1-8}$alkoxy optionally substituted with from one to three substituents independently selected from the group consisting of
(i) halogen, and
(ii) aryl optionally substituted with from one to three halogen substituents, and
(3) oxyaryl optionally substituted with from one to three substituents independently selected from the group consisting of
(i) $C_{1-8}$alkyl,
(ii) $C_{1-8}$alkoxy,
(iii) amino optionally mono or disubstituted with $C_{1-8}$alkyl, and
(iv) halogen, and
(4) halogen.

An example of a compound of Formula (I) is a compound wherein $L^1$-$(CH_2)_p$—$Ar^1$ and $L^2$-$Ar^2$ are dependently selected from:

| Cpd | $L^1$-$(CH_2)_p$—$Ar^1$ | $L^2$-$Ar^2$ |
|---|---|---|
| 1 | NH-[4-$CH_2$-(2-$CH_2CH_3$-imidazol-1-yl)]-phenyl | NH-3-Cl-4-F-phenyl |
| 2 | NH-(4-$CH_2$-morpholin-4-yl)-phenyl | NH-3-Cl-4-F-phenyl |
| 3 | NH-[4-$CH_2$N($CH_3$)$_2$]-phenyl | NH-3-Cl-4-F-phenyl |
| 4 | NH-{4-$CH_2$N[($CH_2$)$_2$O$CH_3$]$_2$}-phenyl | NH-3-Cl-4-F-phenyl |
| 5 | NH-{4-$SO_2$N[($CH_2$)$_2$O$CH_3$]$_2$}-phenyl | NH-3-Cl-4-F-phenyl |
| 6 | NH-{4-$CH_2$-[(2S)-2-$CH_2$OH-pyrrolidin-1-yl]}-phenyl | NH-3-Cl-4-F-phenyl |
| 7 | NH-[4-$SO_2$NH($CH_2$)$_2$-morpholin-4-yl]-phenyl | NH-3-Cl-4-F-phenyl |
| 8 | NH-($CH_2$)$_3$-morpholin-4-yl | NH-3-Cl-4-F-phenyl |
| 9 | NH-($CH_2$)$_3$-morpholin-4-yl | NH-3-C≡CH-phenyl |
| 10 | NH-[4-$CH_2$N($CH_3$)$_2$]-phenyl | NH-3-C≡CH-phenyl |
| 11 | NH-{4-$CH_2$-[(2S)-2-$CH_2$OH-pyrrolidin-1-yl]}-phenyl | NH-3-C≡CH-phenyl |

-continued

| Cpd | L$^1$-(CH$_2$)$_p$—Ar$^1$ | L$^2$-Ar$^2$ |
|---|---|---|
| 12 | NH-(CH$_2$)$_2$-morpholin-4-yl | NH-3-Cl-phenyl |
| 13 | NH-(CH$_2$)$_2$-morpholin-4-yl | NH-3-C≡CH-phenyl |
| 14 | NH-{4-CH$_2$N(CH$_3$)CH$_2$-[(2R)-tetrahydro-furan-2-yl]}-phenyl | NH-3-Cl-4-F-phenyl |
| 15 | NH-{4-CH$_2$N(CH$_3$)CH$_2$-[(2S)-tetrahydro-furan-2-yl]}-phenyl | NH-3-Cl-4-F-phenyl |
| 16 | NH-[4-CH$_2$N(CH$_3$)-tetrahydro-pyran-4-yl]-phenyl | NH-3-Cl-4-F-phenyl |
| 17 | NH-(4-CH$_2$-pyrrolidin-1-yl)-phenyl | NH-3-Cl-4-F-phenyl |
| 18 | NH-[3-Cl-4-CH$_2$N(CH$_3$)$_2$]-phenyl | NH-3-Cl-4-F-phenyl |
| 19 | NH-(4-CH$_2$-morpholin-4-yl)-phenyl | NH-3-Cl-phenyl |
| 20 | NH-(4-CH$_2$-morpholin-4-yl)-phenyl | NH-5-Cl-benzo[1,3]dioxol-4-yl |
| 21 | NH-{4-CH$_2$NHCH$_2$-[(2R)-tetrahydro-furan-2-yl]}-phenyl | NH-3-Cl-4-F-phenyl |
| 22 | NH-(4-CH$_2$-morpholin-4-yl)-phenyl | NH-3-Cl-4-F-phenyl |
| 23 | NH-[4-SO$_2$NH(CH$_2$)$_3$N(CH$_3$)$_2$]-phenyl | NH-3-C≡CH-phenyl |
| 24 | NH-(4-CH$_2$-pyrrolidin-1-yl)-phenyl | NH-{3-Cl-4-[OCH$_2$-(3-F-phenyl)]}-phenyl |
| 25 | NH-[4-CH$_2$N(CH$_3$)$_2$]-phenyl | NH-2,2-F$_2$-benzo[1,3]dioxol-4-yl |
| 26 | NH-6-OCH$_3$-pyridin-3-yl | NH-3-Cl-4-F-phenyl |
| 27 | NH-6-OH-pyridin-3-yl | NH-3-Cl-4-F-phenyl |
| 28 | NH-6-Cl-pyridin-3-yl | NH-3-Cl-4-F-phenyl |
| 29 | NH-[6-NH(CH$_2$)$_3$-morpholin-4-yl]-pyridin-3-yl | NH-3-Cl-4-F-phenyl |
| 30 | NH-6-NH(CH$_2$)$_2$NH$_2$-pyridin-3-yl | NH-3-Cl-4-F-phenyl |
| 31 | NH-(4-CH$_2$-(4-NH$_2$-piperidin-1-yl)]-phenyl | NH-3-Cl-4-F-phenyl |
| 32 | NH-(4-CH$_2$-morpholin-4-yl)-phenyl | NH-6-Br-benzo[1,3]dioxol-4-yl |
| 33 | NH-(4-CH$_3$)-phenyl | NH-5-Cl-benzo[1,3]dioxol-4-yl |
| 34 | NH-(4-CH$_2$-morpholin-4-yl)-phenyl | NH-2,4-Cl$_2$-phenyl |
| 35 | NH-[4-OCH$_2$-(1-CH$_3$-piperidin-3-yl)]-phenyl | NH-2-Cl-5-OCH$_3$-phenyl |
| 36 | NH-[4-OCH$_2$-(1-CH$_3$-piperidin-3-yl)]-phenyl | 2,4-Cl$_2$-phenoxy |
| 37 | NH-[4-OCH$_2$-(1-CH$_3$-piperidin-3-yl)]-phenyl | 3-OCF$_3$-phenoxy |
| 38 | NH-[4-OCH$_2$-(1-CH$_3$-piperidin-3-yl)]-phenyl | S-3-Br-phenyl |
| 39 | NH-[4-OCH$_2$-(1-CH$_3$-piperidin-3-yl)]-phenyl | S-2-Cl-4-F-phenyl |
| 40 | NH-[4-OCH$_2$-(1-CH$_3$-piperidin-3-yl)]-phenyl | NH-5-Cl-benzo[1,3]dioxol-4-yl |
| 41 | NH-(4-CH$_2$-piperidin-1-yl)-phenyl | NH-5-Cl-benzo[1,3]dioxol-4-yl |
| 42 | NH-{3-OCH$_3$-4-[O(CH$_2$)$_2$-morpholin-4-yl]}-phenyl | NH-5-Cl-benzo[1,3]dioxol-4-yl |
| 43 | NH-[3-OCH$_3$-4-(OCH$_2$-tetrahydro-pyran-2-yl)]-phenyl | NH-5-Cl-benzo[1,3]dioxol-4-yl |
| 44 | NH-{4-CH$_2$NHCH$_2$-[(2R)-tetrahydro-furan-2-yl]}-phenyl | NH-5-Cl-benzo[1,3]dioxol-4-yl |
| 45 | NH-(4-CH$_2$-pyrrolidin-1-yl)-phenyl | NH-5-Cl-benzo[1,3]dioxol-4-yl |
| 46 | NH-[4-CH$_2$-(4-CH$_3$-piperazin-1-yl)]-phenyl | NH-5-Cl-benzo[1,3]dioxol-4-yl |
| 47 | NH-(4-CH$_2$-morpholin-4-yl)-phenyl | NH-2,4-Cl$_2$-5-OCH$_3$-phenyl |
| 48 | NH-(4-CH$_2$-morpholin-4-yl)-phenyl | NH-3-Br-phenyl |
| 49 | NH-[4-(CH$_2$)$_2$-morpholin-4-yl]-phenyl | NH-5-Cl-benzo[1,3]dioxol-4-yl |
| 50 | NH-[4-(CH$_2$)$_2$-piperidin-1-yl]-phenyl | NH-5-Cl-benzo[1,3]dioxol-4-yl |
| 51 | NH-[4-CH$_2$-(4-CH$_3$-piperazin-1-yl)]-phenyl | NH-(4-phenoxy)-phenyl |

An example of a compound of Formula (I) includes a compound selected from the group consisting of:

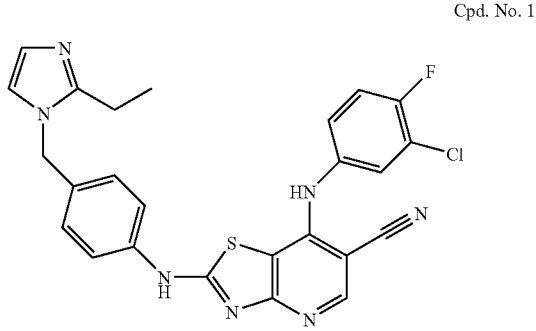

Cpd. No. 1

-continued

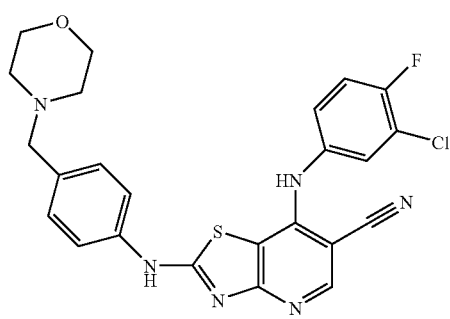

Cpd. No. 2

-continued

Cpd. No. 3

Cpd. No. 4

Cpd. No. 5

Cpd. No. 6

-continued

Cpd. No. 7

Cpd. No. 8

Cpd. No. 9

Cpd. No. 10

Cpd. No. 11

-continued
Cpd. No. 12
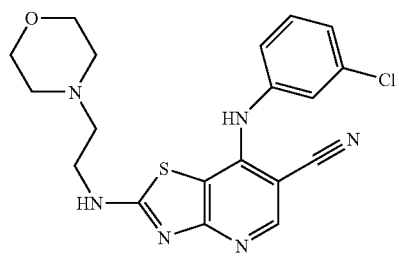
Cpd. No. 13
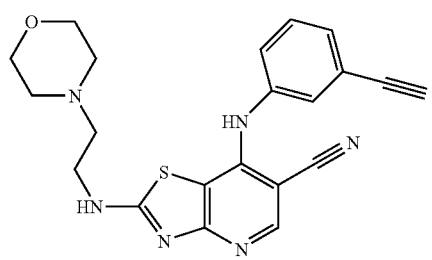
Cpd. No. 14
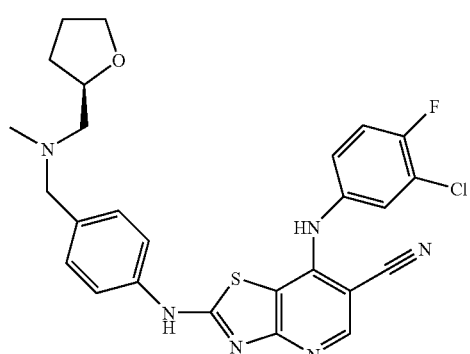
Cpd. No. 15
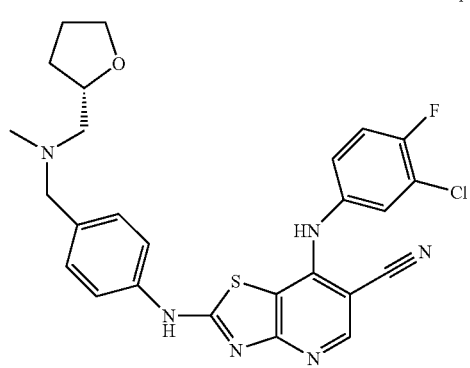
Cpd. No. 16
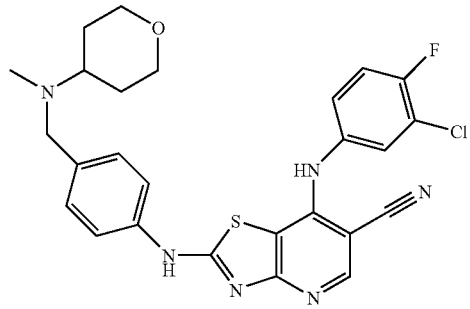
-continued
Cpd. No. 17
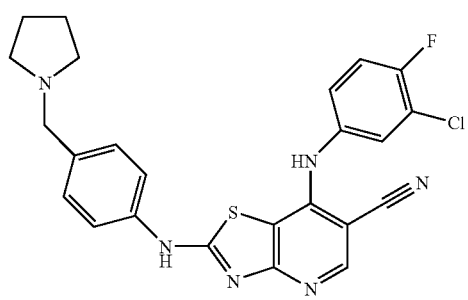
Cpd. No. 18
Cpd. No. 19
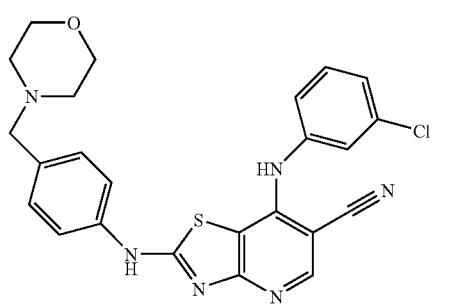
Cpd. No. 20
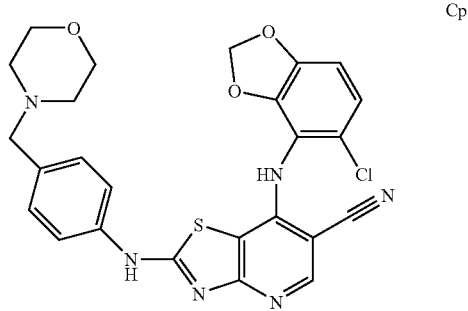
Cpd. No. 21
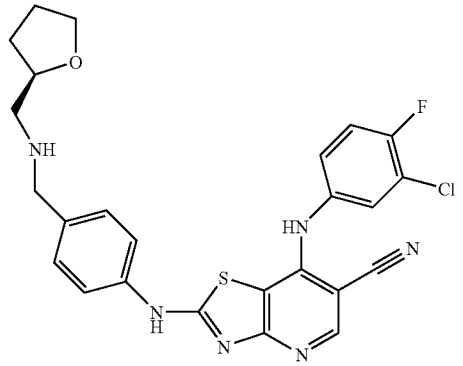

-continued
Cpd. No. 22
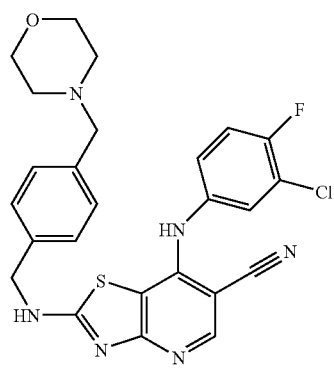
Cpd. No. 23
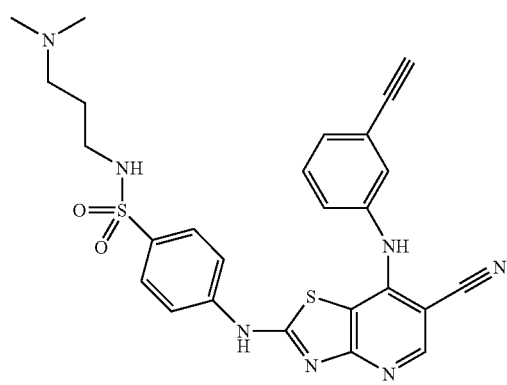
Cpd. No. 24
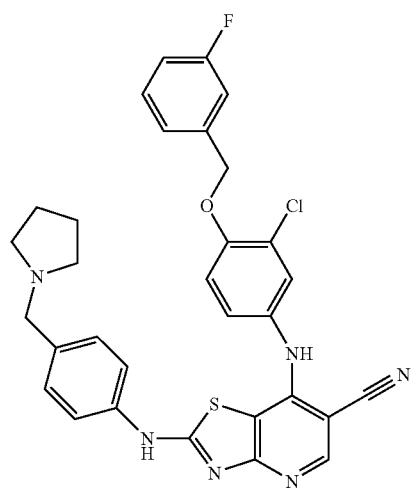
Cpd. No. 25
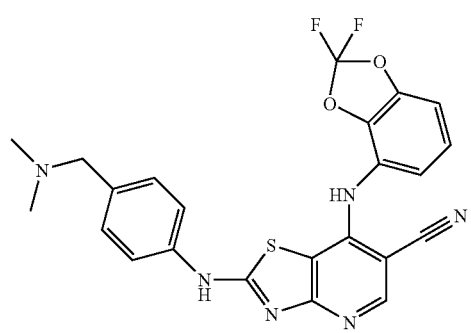
-continued
Cpd. No. 26
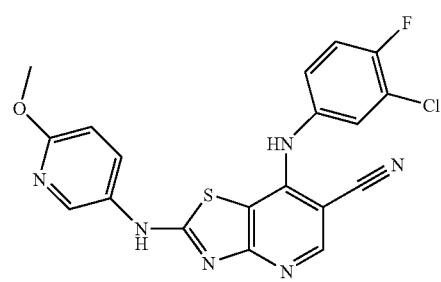
Cpd. No. 27
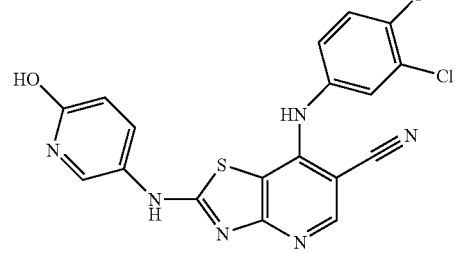
Cpd. No. 28
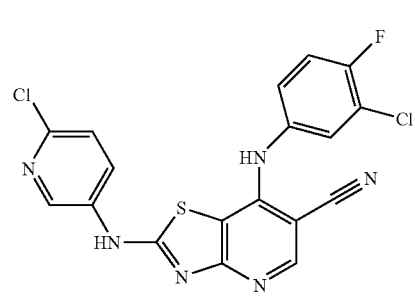
Cpd. No. 29
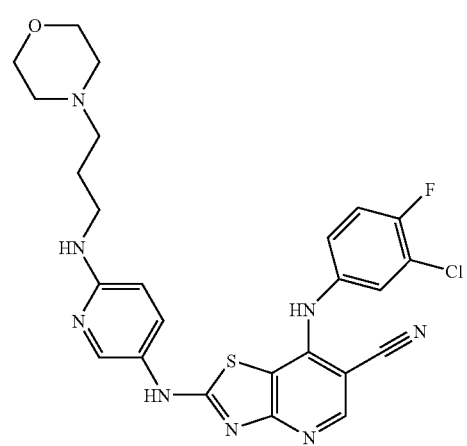

-continued
Cpd. No. 30
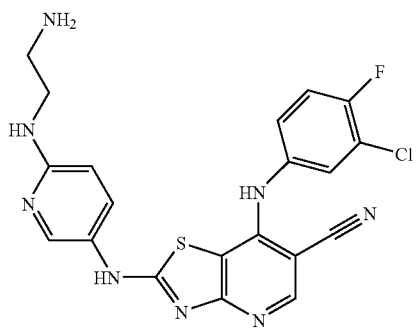
Cpd. No. 31
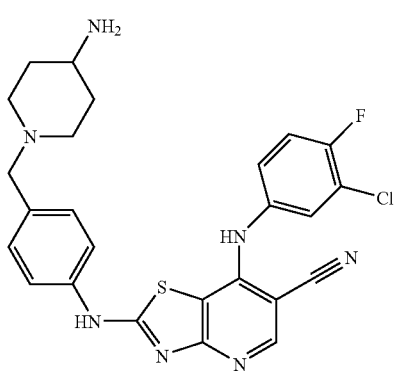
Cpd. No. 32
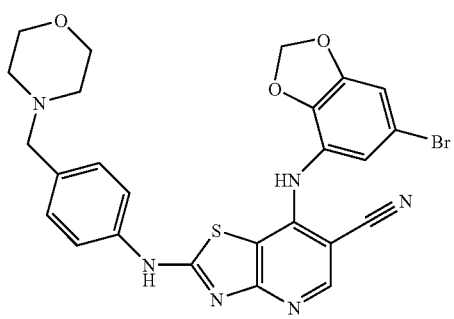
Cpd. No. 33
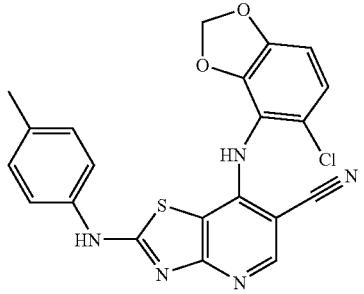
-continued
Cpd. No. 34
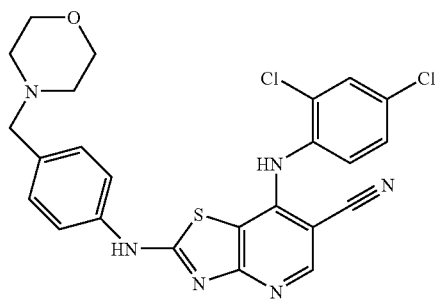
Cpd. No. 35
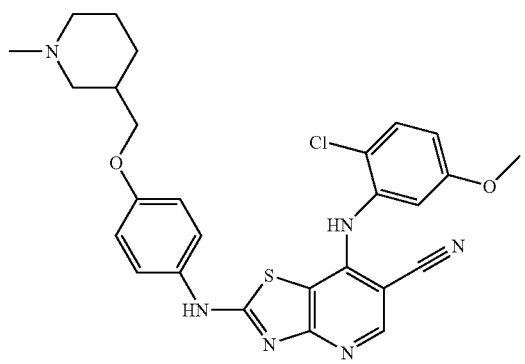
Cpd. No. 36
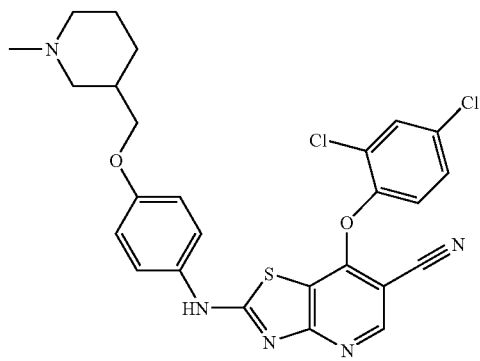
Cpd. No. 37
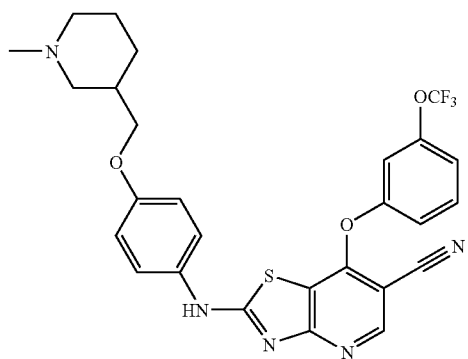

Cpd. No. 38

Cpd. No. 39

Cpd. No. 40

Cpd. No. 41

Cpd. No. 42

Cpd. No. 43

Cpd. No. 44

Cpd. No. 45

-continued

Cpd. No. 46
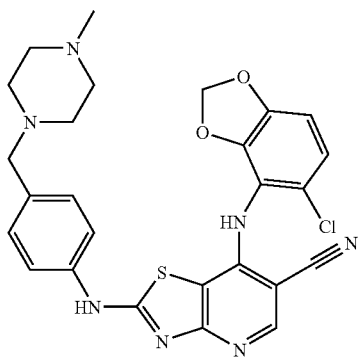

Cpd. No. 47
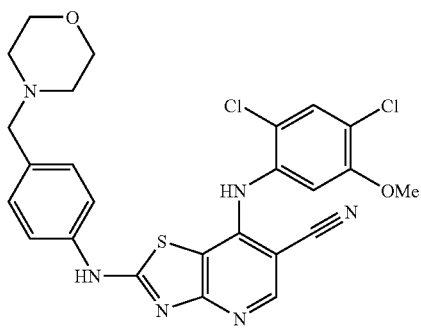

Cpd. No. 48
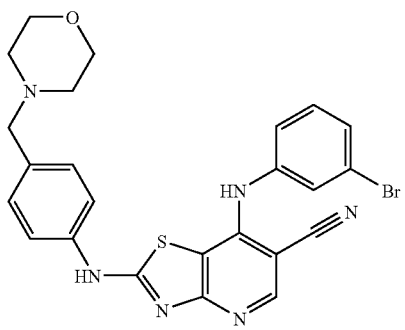

Cpd. No. 49
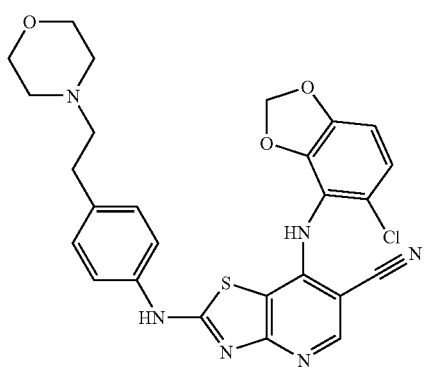

-continued

Cpd. No. 50
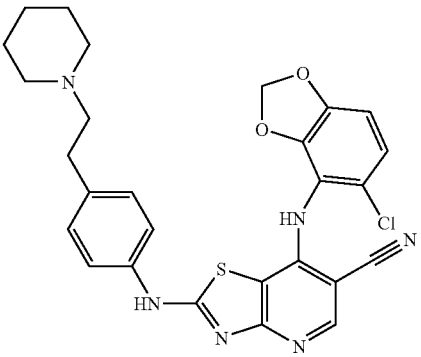

Cpd. No. 51
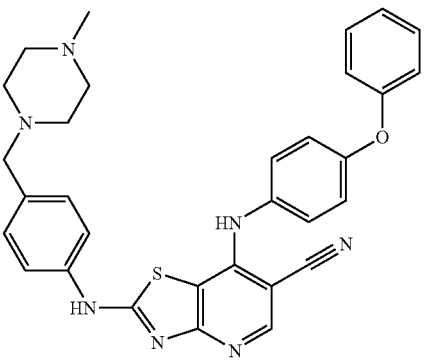

Pharmaceutically Acceptable Forms

Certain compounds of the Formula (I) may exist in various stereoisomeric or tautomeric forms. The present invention encompasses all such kinase inhibiting compounds. These compounds include active compounds in the form of enantiomers or diastereomers. These enantiomers or diastereomers include pure or essentially pure compounds. These compounds also encompass mixtures of enantiomers or mixtures of diasteomers. When enantiomers are present in equimolar amounts, the resulting mixtures are referred to as racemic mixtures. Some of the compounds include tautomers, or a mixture of tautomers.

The compounds of the present invention may be present in the form of pharmaceutically acceptable salts. For use in medicines, the "pharmaceutically acceptable salts" of the compounds of this invention refer to non-toxic acidic/anionic or basic/cationic salts.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Thus, representative pharmaceutically acceptable salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Pharmaceutically acceptable basic/cationic salts include, and are not limited to salts formed with aluminum, 2-amino-2-hydroxymethyl-propane-1,3-diol, ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine or zinc.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3rd Edition, John Wiley & Sons, 1999. The protecting groups may be removed at a convenient subsequent stage using methods known in the art.

The present invention contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" refers to isomers of identical constitution that differ in the arrangement of their atoms in space. Enantiomers and diastereomers are stereoisomers wherein an asymmetrically substituted atom acts as a chiral center. The term "chiral" refers to a molecule that is not superimposable on its mirror image. The term "enantiomer" refers to one of a pair of molecular species that are mirror images of each other and are not superimposable. The term "diastereomer" refers to stereoisomers that are not related as mirror images. The symbols "R" and "S" represent the configuration of substituents around a chiral atom(s). The symbols "R*" and "S*" denote the relative configurations of substituents around a chiral atom(s).

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than H) attached to a cycloalkyl ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "S*," "R*," "E," "Z," "cis," "trans," "exo" and "endo" are used as described herein for indicating atom configuration(s) relative to a core molecule and are intended to be used as defined in the literature (IUPAC Recommendations for Fundamental Stereochemistry (Section E), Pure Appl. Chem., 1976, 45:13-30).

The term "tautomer" is used for isomers that are the result of tautomerism that in turn designates a rapid and reversible interconversion of isomers associated with the actual movement of electrons as well as one or more hydrogen atoms. Each tautomer is capable of independent existence and potential isolation. An art-known example of tautomerism is keto-enol tautomerism.

The compounds of the present invention may be prepared as individual isomers by either isomer-specific synthesis or resolved from an isomeric mixture. Conventional resolution techniques include combining the free base (or free acid) of each isomer of an isomeric pair with an optically active acid (or base) to form an optically active salt (followed by fractional crystallization and regeneration of the free base or acid), forming an ester or amide of each of the isomers of an isomeric pair by reaction with an appropriate chiral auxiliary (followed by fractional crystallization or chromatographic separation and removal of the chiral auxiliary) or resolving an isomeric mixture of either a starting material or a final product using chiral preparative TLC (thin layer chromatography) or a chiral HPLC column.

Furthermore, the compounds of the present invention may have one or more polymorph or amorphous crystalline forms and as such are intended to be included in the scope of the invention. In addition, some of the compounds may form solvates with water (i.e., hydrates) or common organic solvents, and as such are also intended to be encompassed within the scope of this invention.

Chemical Definitions

When any variable (e.g., aryl, heterocyclyl, $R_1$, $R_2$, etc.) occurs more than once in a substituent list, its definition on each occurrence is independent of any other occurrence.

Bond lines drawn into a ring system from a substituent variable (such as $R_6$, $R_9$, etc.) indicate that the substituent may be attached to any of the substitutable ring carbon atoms or heteroatoms. If the ring system is polycyclic, the substituent may be attached to any of the suitable carbon atoms or heteroatoms on the ring into which the bond line is drawn.

As used herein, the following terms are intended to have the following definitions. Additional definitions are provided throughout the specification as needed.

The term "$C_{1-8}$ alkyl," whether used alone or as part of a substituent group, refers to a saturated aliphatic branched or straight-chain monovalent hydrocarbon radical or alkyldiyl linking group having a specified number of carbon atoms, wherein the radical is derived by the removal of one hydrogen atom from a carbon atom and the alkyldiyl linking group is derived by the removal of one hydrogen atom from each of two carbon atoms in the chain. The term "$C_{1-8}$alkyl" refers to a radical having from 1-8 carbon atoms in a linear or branched arrangement. For example, "$C_{1-8}$alkyl" specifically includes the radicals methyl, ethyl, 1-propyl, 2-propyl, 1-butyl, 2-butyl, tert-butyl, 1-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{1-4}$alkyl," whether used alone or as part of a substituent group, refers to a saturated aliphatic branched or straight-chain monovalent hydrocarbon radical or alkyldiyl linking group having a specified number of carbon atoms, wherein the radical is derived by the removal of one hydrogen atom from a carbon atom and the alkyldiyl linking group is derived by the removal of one hydrogen atom from each of two carbon atoms in the chain. The term "$C_{1-8}$alkyl" refers to a radical having from 1-4 carbon atoms in a linear or branched arrangement. For example, "$C_{1-4}$alkyl" specifically includes the radicals methyl, ethyl, 1-propyl, 2-propyl, 1-butyl, 2-butyl, tert-butyl, 1-butyl, and the like. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{1-8}$ alkyl(halogen)$_{1-3}$" refers to a $C_{1-8}$ alkyl radical as defined above wherein one, two or three hydrogen atoms are replaced by a halogen atom. Examples of $C_{1-8}$ alkyl(halogen)$_{1-3}$ are for instance, trifluoromethyl, monochoromethane, and the like.

The term "$C_{1-8}$ alkyl(hydroxy)$_{1-3}$" refers to a $C_{1-8}$ alkyl radical as defined above wherein one, two or three hydrogen atoms are replaced by a hydroxyl group. Hydroxy groups are preferably on different carbon atoms, although it is possible that in certain cases two hydroxyl groups will be on the same carbon atom. Examples of "$C_{1-8}$ alkyl(hydroxy)$_{1-3}$" are for instance hydroxymethyl, hydroxyethyl and the like.

The term "$C_{2-8}$ alkenyl," whether used alone or as part of a substituent group, refers to an alkyl or alkyldiyl radical containing at least one carbon to carbon double bond. Typically, one carbon-carbon double bond is present; and, optionally, any number of double bonds may be present whereby a stable compound results. The radical may be in either the Z or E conformation about the double bond(s).

The term "$C_{2-6}$alkenyl" refers to an alkenyl radical having from 2-6 carbon atoms. For example, "$C_{2-4}$alkenyl" specifically includes the radicals ethenyl, propenyl, allyl (2-propenyl), butenyl, pentenyl, hexenyl and the like. As described above, an alkenyl radical may be similarly attached to a core molecule and further substituted where indicated.

The term "$C_{2-8}$ alkynyl," whether used alone or as part of a substituent group, refers to an alkyl or alkyldiyl radical containing at least one carbon to carbon triple bond. Typically, one carbon-carbon triple bond is present; and, optionally, any number of triple bonds may be present whereby a stable compound results.

The term "$C_{2-6}$alkynyl" refers to an alkynyl radical having from 2-6 carbon atoms. For example, "$C_{2-4}$alkynyl" specifically includes the radicals ethynyl, propynyl, butynyl, pentynyl, hexynyl and the like. As described above, an alkynyl radical may be similarly attached to a core molecule and further substituted where indicated.

The term "$C_{1-8}$ alkoxy," whether used alone or as part of a substituent group, refers to an alkyl or alkyldiyl radical attached through an oxygen linking atom. For example, "$C_{1-4}$alkoxy" specifically includes the radicals methoxy, ethoxy, propoxy, butoxy, pentoxy, hexoxy, heptoxy, octoxy and the like. As described above, an alkoxy radical may be similarly attached to a core molecule and further substituted where indicated.

The term "$C_{3-8}$ cycloalkyl," whether used alone or as part of a substituent group, refers to a saturated or partially unsaturated, monocyclic or fused alkyl ring system radical. Examples of cycloalkyl ring systems include, but are not limited to, cyclopropyl, cyclobutyl, cyclopentyl, cyclohexyl, cycloheptyl, cyclooctyl, adamantanyl or indanyl and the like. For example, "$C_{3-8}$cycloalkyl" specifically includes cyclopropyl, cyclobutyl, cyclopentyl, cyclohexyl, cycloheptyl and cyclooctyl. As described above, a cycloalkyl radical may be similarly attached to a core molecule and further substituted where indicated.

The term "aryl," whether used alone or as part of a substituent group, refers to an aromatic monocyclic or fused ring system radical. Examples of aryl ring systems include, but are not limited to, phenyl, naphthalenyl, fluorenyl, indenyl, azulenyl, anthracenyl, naphthalenyl, fluorenyl, indenyl or anthracenyl and the like. As described above, an aryl radical may be similarly attached to a core molecule and further substituted where indicated.

The term "aromatic" refers to a cycloalkyl or heterocyclyl ring system having a fully unsaturated, conjugated π electron system; i.e. an aryl or heteroaryl ring system.

The term "heterocyclyl," whether used alone or as part of a substituent group, refers to a saturated or partially saturated, monocyclic or fused heterocycloalkyl ring system radical. Partially saturated systems include rings such as those named with dihydro, trihydro, tetrahydro, hexahydro and the like. Examples of heterocyclyl radicals include, and are not limited to, 2H-pyrrole (including 2-pyrrolinyl or 3-pyrrolinyl), pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolinyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl, 1,3-benzodioxolyl or 2,3-dihydro-1,4-benzodioxinyl and the like. As described above, a heterocyclyl radical may be similarly attached to a core molecule and further substituted where indicated.

The term "hetero," when used as a prefix for a ring system, refers to the replacement of at least one carbon atom member in a cycloalkyl or aryl ring system with a heteroatom selected from N, S, O or P. Where chemically stable and allowed by the amount of ring atoms, a ring may have 1, 2, 3 or 4 nitrogen atom members; alternatively, a ring may have 0, 1, 2 or 3 nitrogen atom members and 1 oxygen or sulfur atom member. When allowed by available valences, up to four adjacent ring members may be nitrogen atoms (e.g. tetrazole); and, up to two adjacent ring members may be heteroatoms, where one heteroatom is nitrogen and the other is one selected from N, S or O.

The term "heteroaryl," whether used alone or as part of a substituent group, refers to a heteroaromatic monocyclic or fused ring system radical. Examples of heteroaryl rings include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, azaindolyl, isoindolyl, benzo[b]furyl, benzo[b]thienyl, indazolyl, azaindazolyl, benzimidazolyl, benzthiazolyl, benzoxazolyl, benzisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, naphthyridinyl, pteridinyl and the like.

The term "benzo-fused" refers to a bicyclic fused ring system radical formed by a monocyclic radical fused with a benzene ring; the benzo-fused radical may be attached to a core molecule via either ring of the bicyclic system.

The term "benzo-fused cycloalkyl" refers to a bicyclic ring system radical wherein a monocyclic cycloalkyl radical is fused to a benzene ring. Typical benzo-fused cycloalkyl radicals include indanyl, 1,2,3,4-tetrahydro-naphthalenyl, 5,6,7,8-tetrahydro-naphthalenyl, 6,7,8,9,-tetrahydro-5H-benzocycloheptenyl, 5,6,7,8,9,10-hexahydro-benzocyclooctenyl and the like. A benzo-fused cycloalkyl ring system is a subset of the cycloalkyl group.

The term "benzo-fused heterocyclyl" refers to a bicyclic ring system radical wherein a monocyclic heterocyclyl radical is fused to a benzene ring. Typical benzo-fused heterocyclyl radicals include 1,3-benzodioxolyl (also known as 1,3-methylenedioxyphenyl), indolinyl, 2,3-dihydro-1,4-benzodioxinyl (also known as 1,4-ethylenedioxyphenyl), benzo-dihydro-furyl, benzo-tetrahydro-pyranyl, benzo-dihydro-thienyl and the like. A benzo-fused heterocyclyl ring system is a subset of the heterocyclyl group.

The term "benzo-fused heteroaryl" refers to a bicyclic ring system radical wherein a monocyclic heteroaryl radical is fused to a benzene ring. Typical benzo-fused heteroaryl radicals include indolyl, isoindolyl, benzo[b]furyl, benzo[b]thienyl, indazolyl, benzthiazolyl, quinolinyl, isoquinolinyl, cinnolinyl, phthalazinyl, quinazolinyl, pteridinyl and the like. A benzo-fused heteroaryl ring is a subset of the heteroaryl group.

The term "fused" refers to ring systems fused on adjacent ring atoms, those fused on a single ring atom and those fused on nonadjacent ring atoms. The types and amount of rings formed are limited by available ring valences, starting materials or synthetic methods. In any case, all such fused ring systems are intended to be included in the scope of the present compounds and associated synthetic methods.

Monocyclic rings forming bicyclic, tricyclic and the like ring systems are fused on adjacent ring atoms, wherein each monocyclic ring shares two ring atoms, whereby the common ring atoms are the points of attachment for the two rings, and wherein the common atoms may be a carbon or nitrogen atom. Bicyclic, tricyclic and the like ring system radicals are derived by the removal of one hydrogen atom from a single ring carbon atom of the ring system.

Monocyclic rings forming spirocyclic ring systems are fused on a single ring atom, wherein each monocyclic ring shares one ring atom, whereby the common ring atom is the point of attachment for the two rings, and wherein the common atom is a carbon atom. Spirocyclyl radicals are derived by the removal of one hydrogen atom from a single ring carbon atom of the ring system. Typical spirocyclyl radicals include spiro[1.4]dioxolanyl, spiro[5.5]undecyl, 3-oxa-1-aza-spiro[4.4]nonenyl and the like.

Monocyclic ring systems fused on nonadjacent ring atoms are those that form a variety of bridged bicyclic ring systems. Bridged bicyclic radicals are derived by the removal of one hydrogen atom from a single ring carbon atom of the ring system. Typical bridged bicyclic radicals include bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl and the like.

Polycyclic bridged and nonbridged ring systems are those ring systems which are further fused on nonadjacent ring atoms to form a variety of common polycyclic ring systems. Polycyclyl radicals are derived by the removal of one hydrogen atom from a single ring carbon atom of the ring system. Typical polycyclyl radicals include adamantanyl, quinuclidinyl, octahydro-4,7-methano-1H-indenyl, octahydro-2,5-methano-pentalenyl and the like.

The term "C(O)" refers to a carbonyl linking group moiety.

The term "substituted," refers to a core molecule in which one or more hydrogen atoms have been replaced with that amount of substituents allowed by available valences. Substitution is not limited to the core molecule, but may also occur on a substituent radical, whereby the radical becomes a linking group.

The term "independently selected" refers to two or more substituents that may be selected from a substituent variable group, wherein the selected substituents may be the same or different.

The term "dependently selected" refers to one or more substituent variables that are specified in an indicated combination for substitution in a core molecule (e.g. variables that refer to groups of substituents appearing in a tabular list of compounds).

In general, IUPAC nomenclature rules are used herein. Nomenclature for radical substituents was derived by first indicating the atom having the point of attachment, followed by the linking group atoms toward the terminal chain atom from left to right, substantially as in:

—(C$_{1-6}$)alkyl-C(O)NH—(C$_{1-6}$)alkyl-Ph.

Pharmaceutical Preparations & Methods of Use

The present invention includes a first method for inhibiting unregulated protein kinase activity comprising contacting the protein kinase domain with one or more compounds of Formula (I).

The first method also includes inhibiting increased or unregulated protein kinase expression or signaling leading to unregulated cell proliferation comprising contacting a protein kinase receptor with one or more compounds of Formula (I).

The first method further comprises inhibiting the unregulated expression of a protein kinase such as EGFR, HER-2, c-Src, Lyn, Abl and the like.

The present invention includes a second method for use of a compound of Formula (I) as a therapeutic agent for treating or preventing a chronic or acute kinase mediated disease in a subject in need thereof comprising administering to the subject an effective amount of a compound of Formula (I) or composition thereof.

The second method includes administering to the subject an effective amount of a compound of Formula (I) or composition thereof in the form of a medicament.

The second method includes a chronic or acute disease mediated by a tyrosine-kinase selected from EGFR, HER-2, c-Src or Lyn.

The present invention includes a third method for use of a compound of Formula (I) as a therapeutic agent for inhibiting the effects of unregulated kinase activity in a subject in need thereof comprising administering to the subject an effective amount of a compound of Formula (I) or composition or medicament thereof.

The third method includes inhibiting the effects of unregulated activity of a tyrosine-kinase selected from EGFR, HER-2, c-Src or Lyn.

The present invention includes a fourth method for use of a compound of Formula (I) as a therapeutic agent for treating or preventing a chronic or acute kinase mediated cancer in a subject in need thereof comprising administering to the subject an effective amount of a compound of Formula (I) or composition thereof.

The fourth method includes suppressing a chronic or acute tumor associated with non-small-cell lung cancers, colon cancers, breast cancers and the like wherein the cancer is mediated by a tyrosine-kinase selected from EGFR, HER-2, c-Src or Lyn.

The fourth method also includes treating or preventing chronic unregulated cell proliferation whereby cancer remission is induced in the subject.

The present invention includes a fifth method for use of a compound of Formula (I) as a therapeutic agent for treating or preventing chronic or acute kinase mediated diseases characterized by unregulated cell proliferation or metastatic cancer cell invasion and migration.

The present invention includes a sixth method for use of a compound of Formula (I) as a therapeutic agent for treating or preventing viral infection by an EGFR kinase mediated cytomegalovirus.

The present invention encompasses the compounds of Formula (I) for use as a medicine.

The present invention further encompasses the use of the compounds of Formula (I) for the manufacture of a medicament for treating any of the conditions mentioned above.

The term "chronic or acute kinase mediated disorder" as used herein, includes, and is not limited to disorders and diseases associated with unregulated kinase activity and conditions that accompany such activity.

The term "unregulated kinase activity" refers to 1) increased or unregulated kinase expression or signaling, 2) increased kinase expression leading to unregulated cell proliferation, 3) increased kinase signalling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor. may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that the compounds of the present invention are therapeutically useful for treating, preventing or ameliorating diseases disorders or conditions such as, without limitation, osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus), heart disease (such as atherosclerosis, neointima formation or transplantation-induced vasculopathies (such as restenosis and the like), lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like).

The term "administering . . . an effective amount of a compound . . . " with respect to the methods of the present invention, refers to a means for treating, ameliorating or preventing a disease, disorder or syndrome as described herein with a compound specifically disclosed or a compound or prodrug thereof, which would obviously be included within the scope of the invention albeit not specifically disclosed for certain of the instant compounds.

Such methods include therapeutically administering an effective amount of one or more compounds of Formula (I) or a composition or medicament thereof at different times during the course of a therapy or concurrently in a combination form. Such methods further include therapeutically administering an effective amount of one or more compounds of Formula (I) with one or more therapeutic agents at different times during the course of a therapy or concurrently in a combination form.

The term "prodrug" refers to a metabolic precursor of a compound of Formula (I) or pharmaceutically acceptable form thereof. In general, a prodrug is a functional derivative of a compound which may be inactive when administered to a subject but is readily convertible in vivo into an active metabolite compound.

The term "active metabolite" refers to a metabolic product of a compound that is pharmaceutically acceptable and effective. Conventional procedures for the selection and preparation of suitable prodrug derivatives are described, for example, in "Design of Prodrugs", ed. H. Bundgaard, Elsevier, 1985.

The term "subject" as used herein, refers to an animal, preferably a mammal, most preferably a human, who has been the object of treatment, observation or experiment and is at risk of (or susceptible to) developing a disease or disorder or having a disease or disorder related to unregulated kinase activity.

The term "effective amount" refers to that amount of active compound or pharmaceutical agent that elicits the biological or medicinal response (such as inhibiting activation of unregulated kinase activity) in a tissue system, animal or human, that is being sought by a researcher, veterinarian, medical doctor, or other clinician, which includes alleviation of the symptoms of the disease or disorder being treated. The effective amount of a compound of Formula (I) exemplified in such a method is from about 0.001 mg/kg/day to about 300 mg/kg/day or has an $IC_{50}$ (50% inhibition concentration) of about 25 µM or less, or about 10 µM or less, preferably of about 1 µM or less, more preferably of about 0.5 µM or less, and most preferably of about 0.1 µM or less.

The term "composition" refers to a product containing a compound of the present invention (such as a product comprising the specified ingredients in the specified amounts, as well as any product which results, directly or indirectly, from such combinations of the specified ingredients in the specified amounts).

The term "medicament" refers to a product for use in treating or ameliorating a kinase mediated disorder or condition.

The term "pharmaceutically acceptable" refers to molecular entities and compositions that are of sufficient purity and quality for use in the formulation of a composition or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The term "combination therapy" refers to the use of one or more compounds of Formula (I) or composition or medicament thereof in combination with one or more therapeutic agents for the treatment of a number of different kinase mediated disorders and advantageously may facilitate the use of a reduced effective dose of the compound of Formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The terms "treating" or "preventing" refer, without limitation, to facilitating the eradication of, inhibiting the progression of or promoting stasis of a malignancy.

The term "radiation therapy" refers to a therapy that comprises exposing the subject in need thereof to radiation. The present invention includes a method for administering one or more compounds of Formula (I) or composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

An embodiment of the present invention includes a pharmaceutical composition comprising an admixture of one or more compounds of Formula (I) and/or one or more pharmaceutically acceptable forms thereof and one or more pharmaceutically acceptable excipients.

The pharmaceutically acceptable forms for a compound of Formula (I) include a pharmaceutically acceptable salt, ester, prodrug or active metabolite of a compound of Formula (I).

The present invention further includes the use of a process for making the composition or medicament comprising mixing one or more of the instant compounds and an optional pharmaceutically acceptable carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation. Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the composition or medicament contains an effective amount of the active ingredient necessary to be therapeutically or prophylactically effective as described above. The composition or medicament may contain from about 0.001 mg to about 5000 mg (preferably, from about 0.001 to about 500 mg) of the active compound or prodrug thereof and may be constituted into any form suitable for the mode of administration selected for a subject in need. A contemplated effective amount may range from about 0.001 mg to about 300 mg/kg of body weight per day. Preferably, the range is from about 0.003 to about 100 mg/kg of body weight per day. Most preferably, the range is from about 0.005 to about 15 mg/kg of body weight per day. The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

A person skilled in the art would be able to determine the correct dose given the condition of the patient.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. Except where indicated, starting materials and intermediates used in the schemes and examples are prepared by known methodologies well within the ordinary skill of persons versed in the art. No attempt has been made to optimize the yields obtained in any of the example reactions. One skilled in the art would also know how to increase such yields through routine variations in materials, solvents, reagents, reaction conditions and the like. All commercially available chemicals were obtained from commercial suppliers and used without further purification. Particular equipment components used in the examples such as reaction vessels and the like are also commercially available.

The terms used in describing the invention are commonly used and known to those skilled in the art. Chemical formulas as used herein will have their ordinary meaning know to persons skilled in the art. When used herein, the following abbreviations have the indicated meanings:

AcOH acetic acid
Cpd compound
DCM dichloromethane
DMF N,N-dimethylformamide
DMSO dimethyl sulfoxide
EtOAc ethyl acetate
hr(s)/min(s) hour(s)/min(s)
IPA isopropyl alcohol
LAH lithium aluminum hydride
MCPBA meta-chloroperoxybenzoic acid or 3-chloroperoxybenzoic acid
MeOH methanol
NMP n-methyl pyrrolidinone or 1-methyl-2-pyrrolidinone
Ph phenyl
PSI pounds per square inch
RT/rt/r.t. room temperature
sat'd saturated
TEA triethylamine
TFA trifluoroacetic acid
THF tetrahydrofuran

SCHEME A

Chloroacetyl chloride Compound A2 is reacted with a solution of t-butyl cyanoacetate Compound A1 in a base at a temperature maintained between about −20° C. and 10° C. for a period of time (about 3-8 hr) to provide Compound A3 as the product. The Compound A1 solution is formed using a base such as sodium hydride, potassium t-butoxide and the like or mixtures thereof and a solvent that is suitable for the given base such as THF, DMF, t-butanol and the like or mixtures thereof.

Compound A3 is treated with an organic acid solution and is maintained at a temperature between about −20° C. and 5° C. for a period of time (about 18 hr) to provide Compound A4. The organic acid solution is formed using a preferred acid such as TFA and the like in a preferred solvent such as methylene chloride and the like).

Compound A4 is reacted with a solution of a suitably substituted Compound A5 at a temperature between about −20° C. to 50° C. for a period of time (about 5-72 hr) to provide Compound A6. Compound A5 is a thioimido salt such as a potassium salt substituted with a suitable leaving group or nascent leaving group, $L^a$, such as —$SCH_3$ and the like. The Compound A5 solution is formed using a solvent such as acetone, THF, EtOAc and the like or mixtures thereof.

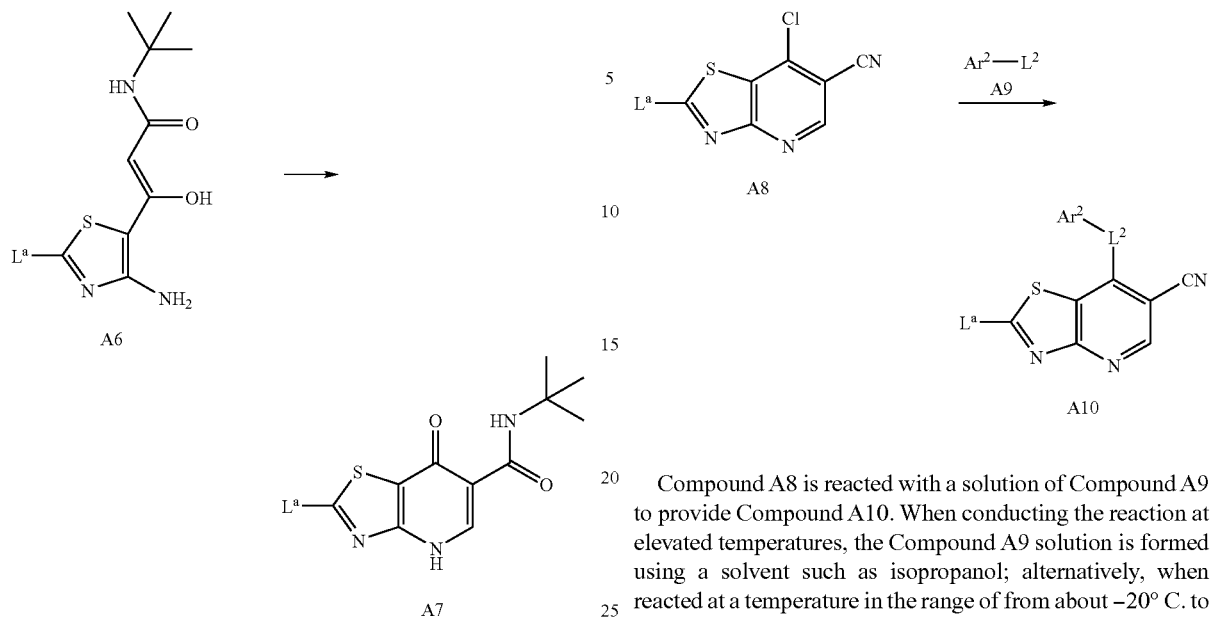

Compound A6 is reacted with a solvated reagent at a temperature between about 50° C. to 125° C. for a period of time (typically 1-2 hr) to provide Compound A7. The solvated reagent is formed using a reagent such as DMF-dimethyl acetal or trimethylorthoformate and the like or mixtures thereof in a solvent such as DMF and the like.

A solution of Compound A7 is reacted with a chlorinating agent solution at a temperature maintained between about −20° C. to 110° C. to provide Compound A8. The chlorinating agent is a neat or solvated agent such as thionyl chloride, phosphorus oxychloride, phosphorus pentachloride and the like or mixtures thereof in a solvent such as DMF and the like.

Compound A8 is reacted with a solution of Compound A9 to provide Compound A10. When conducting the reaction at elevated temperatures, the Compound A9 solution is formed using a solvent such as isopropanol; alternatively, when reacted at a temperature in the range of from about −20° C. to about 50° C., the solution is formed using a strong non-nucleophilic base such as potassium t-butoxide and the like. The $L^2$ portion of Compound A9 may be varied for reaction with a suitable $C^7$ halogen atom on Compound A8 to provide other compounds of the present invention. The $L^2$ portion is a suitably reactive heteroatom such as N, NH, $NH_2$, O or S.

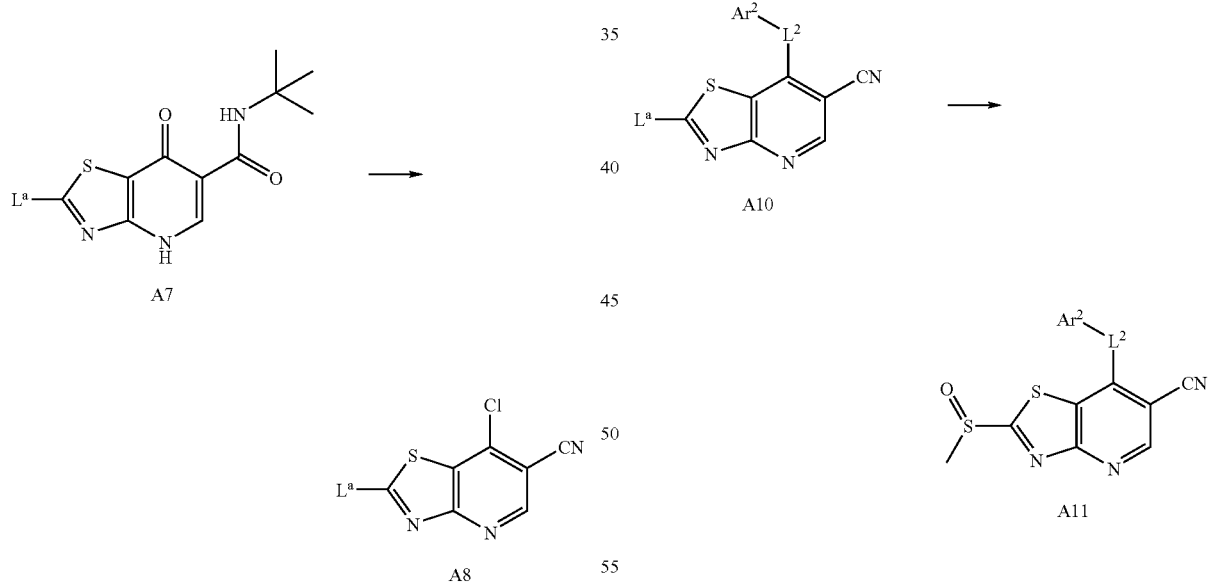

Compound A10 is reacted with an oxidizing agent solution at a temperature maintained between about −20° C. to 5° C. to provide Compound A11. The oxidizing agent is an agent such as MCPBA or hydrogen peroxide and the like or mixtures thereof and the solution is formed using a solvent such as methylene chloride, chloroform or up to 10% ethanol and the like or mixtures thereof. When the Compound A10 $L^a$ group is a moiety such as $SCH_3$, the reaction formed an "activated" group such as $S(O)CH_3$.

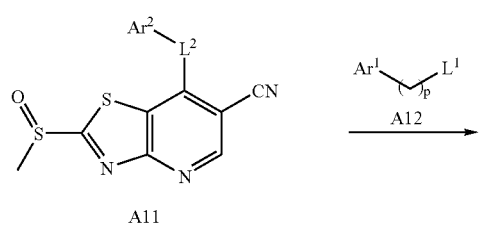

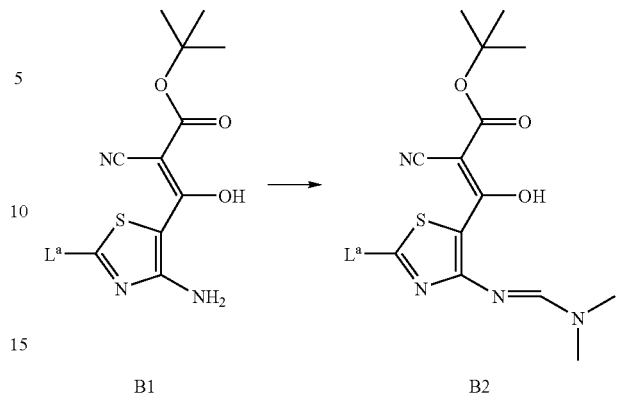

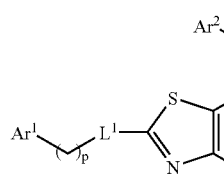

Formula (I)

Compound A11 is reacted with an acidic solution of Compound A12 at a temperature maintained between about 20° C. to 60° C. for a period of time (typically 2-24 hr) to provide a compound of Formula (I). The Compound A12 solution is formed using an acid such as acetic acid and the like.

The $L^1$ portion moiety of Compound A12 may be reacted with a suitable group activated on Compound A11 to provide other compounds of Formula (I) wherein the $L^1$ moiety is a suitably reactive heteroatom such as NH, $NH_2$, O or S.

Scheme B

Scheme B describes a procedure whereby Compound A7 may also be generated from A3 by an alternative route.

Compound B1 is reacted with a solvated reagent at a temperature between about 50° C. to 125° C. for a period of time (typically 1-2 hr) to provide Compound B2. The solvated reagent is formed using a reagent such as DMF-dimethyl acetal or trimethylorthoformate and the like or mixtures thereof in a solvent such as DMF and the like.

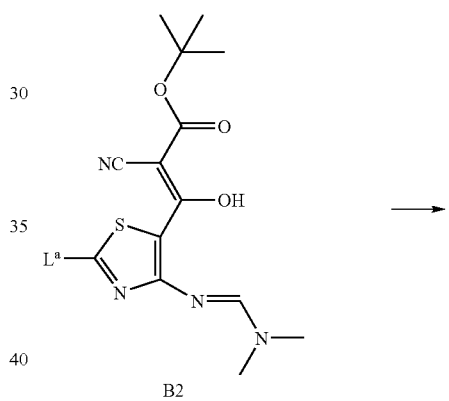

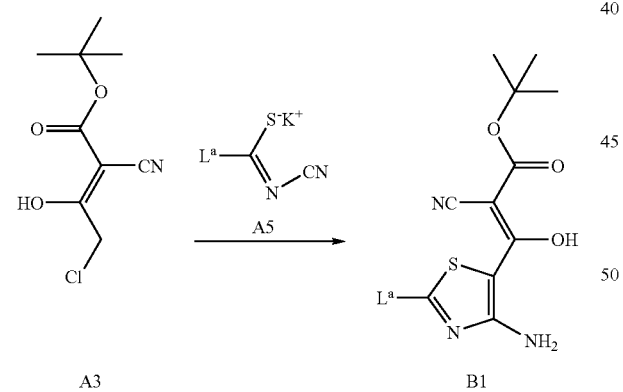

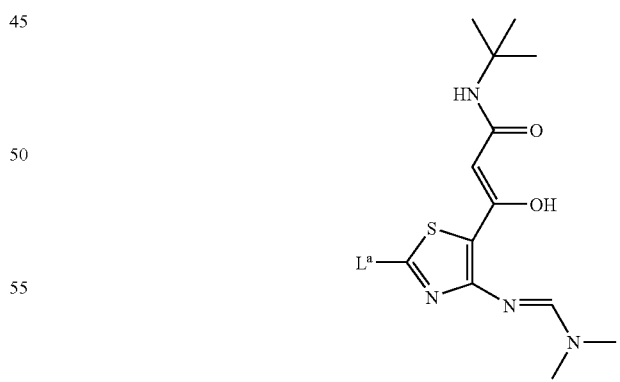

Compound A3 is reacted with a solution of a suitably substituted Compound A5 at a temperature between about −20° C. to 50° C. for a period of time (about 5-48 hr) to provide Compound B1. Compound A5 is a thioimido salt such as a potassium salt substituted with a suitable leaving group or nascent leaving group, $L^a$, such as —$SCH_3$ and the like. The Compound A5 solution is formed using a solvent such as acetone, THF, EtOAc and the like or mixtures thereof.

Compound B2 is treated with an organic acid solution and is maintained at a temperature between about −20° C. and 5° C. for a period of time (about 3 hr) to provide Compound B3. The organic acid solution is formed using a preferred acid such as TFA and the like in a preferred solvent such as methylene chloride and the like.

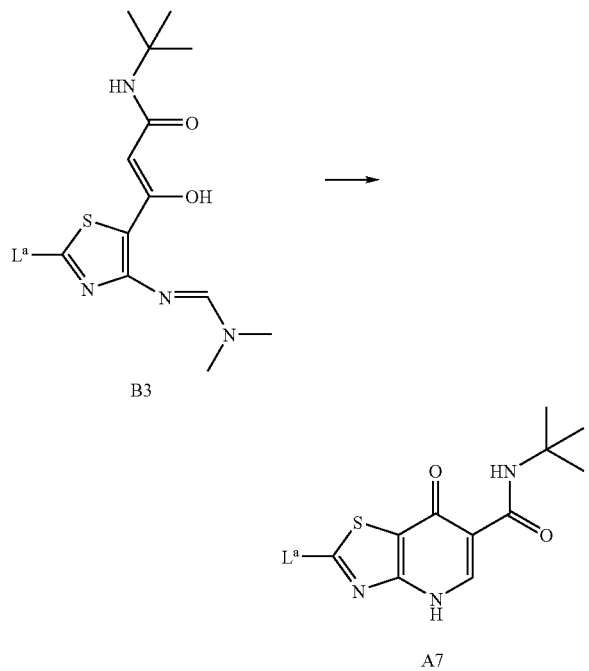

B3

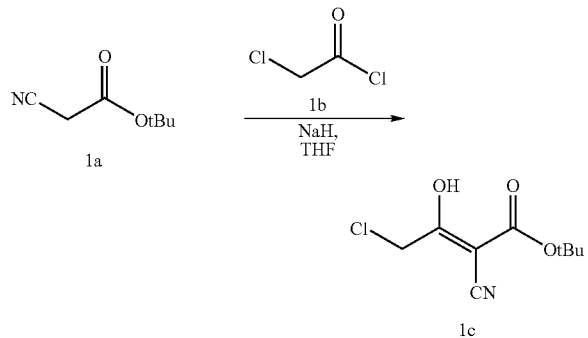

A7

Compound B3 is heated in a polar protic solvent at a temperature between about 50° C. and 100° C. for a period of time (approximately 6 hr) to provide Compound A7. The reaction is carried out in a preferred solvent such as isopropanol and the like.

EXAMPLE 1

7-(3-chloro-4-fluoro-phenylamino)-2-(4-pyrrolidin-1-ylmethyl-phenylamino)-thiazolo[4,5-b]pyridine-6-carbonitrile (Cpd 17)

A solution of t-butyl cyanoacetate Compound 1a (32.2 g, 228 mmol, 1.14 M) in THF was added dropwise to a suspension of 60% NaH (9.13 g, 228 mmol) in THF (200 mL) under nitrogen at 0° C. The mixture was stirred until hydrogen gas evolution ceased and the solution became homogeneous. A solution of chloroacetyl chloride Compound 1b (18.5 mL, 228 mmol) in THF (100 mL) was added at a rate sufficiently slow enough to maintain the temperature below 10° C. After stirring for 4 hr, the reaction was quenched at 0° C. with water (25 mL). The resulting precipitate was filtered through Celite 545. The organic solution was then evaporated down to give a residue that was partitioned between ether and 1 M NaOH. The aqueous layer was washed with ether (3×) and adjusted to pH 5 with NaH$_2$PO$_4$. The aqueous layer was extracted with EtOAc, then dried over MgSO$_4$ and evaporated to yield 4-chloro-2-cyano-3-hydroxy-but-2-enoic acid tert-butyl ester Compound 1c (26.3 g) as a light brown foam. $^1$H NMR (CDCl3) δ 4.34 (br s, 2H), 1.47 (s, 9H). MS 216 (M$^-$).

TFA (75 mL) in water (10 mL) was added dropwise to a solution of 4-chloro-2-cyano-3-hydroxy-but-2-enoic acid tert-butyl ester Compound 1c (47.8 g, 220 mmol) in DCM (200 mL) at 0° C. The mixture was then warmed to ambient temperature and stirred for 18 hr. The mixture was evaporated down under vacuum to give a residue that was partitioned between DCM and a solution of saturated sodium bicarbonate. After repeated washing, the DCM layer was dried over MgSO$_4$ and evaporated down to give a crude product N-tert-butyl-4-chloro-3-oxo-butyramide Compound 1d (23.9 g) as a dark brown viscous oil. $^1$H NMR (CDCl3) δ 6.32 (br s, 1H), 4.28 (s, 2H), 3.49 (s, 2H), 1.37 (s, 9H). MS 192, 194 (MH$^+$).

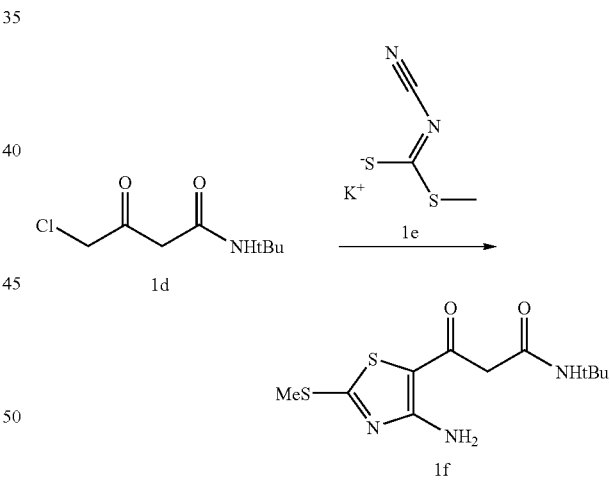

Potassium methyl N-cyanodithioimidocarbonate Compound 1e (21.3 g, 125 mmol) was added to a solution of Compound 1d (23.9 g, 125 mmol) at 0° C. in acetone (300 mL). The reaction was stirred for 1 hr at 0° C. and then at RT for 18 hrs. The solvent was removed under vacuum and the product extracted into EtOAc from water. The combined organic extracts were dried over MgSO$_4$, then filtered and evaporated to give 3-(4-amino-2-methylsulfanyl-thiazol-5-yl)-N-tert-butyl-3-oxo-propionamide Compound 1f (34.6 g) as a tan solid. The material was used in the next step without further purification. $^1$H NMR (DMSO) δ 7.73 (br s, 3H), 3.35 (s, 2H), 2.68 (s, 3H), 1.27 (s, 9H). MS 288 (MH$^+$).

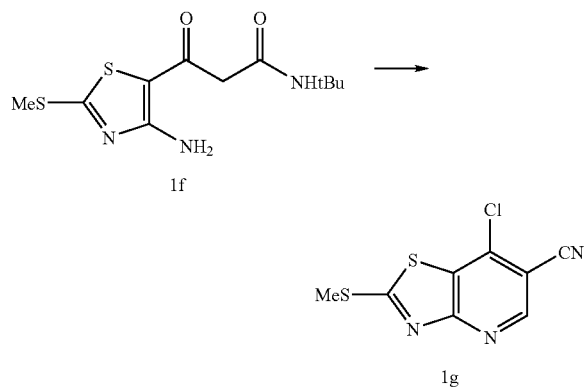

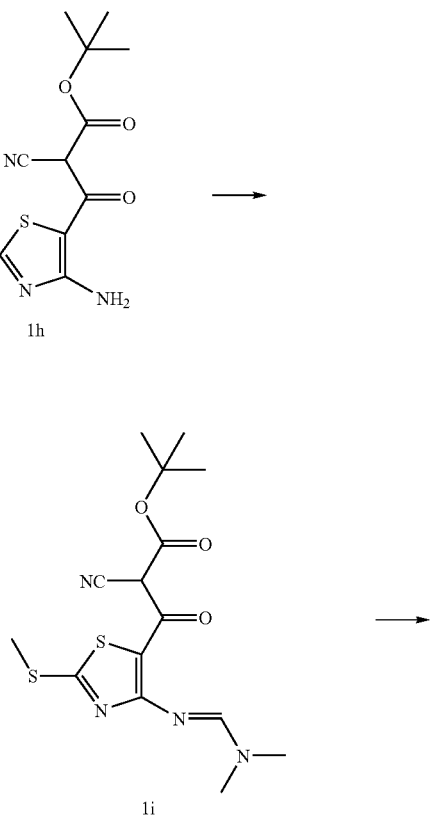

A mixture of Compound 1f (34.6 g, 120 mmol), DMF-dimethyl acetal (34.0 mL, 240 mmol, 94% purity) and DMF (200 mL) were combined and heated to 80° C. for 90 minutes. The conversion to the cyclized intermediate, 7-hydroxy-2-methylsulfanyl-thiazolo[4,5-b]pyridine-6-carbonitrile was confirmed by LCMS (MS 298, MH+). The mixture was then cooled to 0° C. and SOCl2 was added dropwise (44 mL, 600 mmol). The reaction mixture was stirred for 2 hrs at ambient temperature. The mixture was then cooled back down to 0° C. and water (approximately 300 mL) was added dropwise. The resulting brown solid was collected by filtration and subsequently washed with water and MeOH to provide 7-chloro-2-methylsulfanyl-thiazolo[4,5-b]pyridine-6-carbonitrile Compound 1g (16.1 g) as a tan solid. $^1$H NMR (CDCl3) δ 8.82 (s, 1H), 2.91 (s, 3H). MS 242, 244 (MH+), 264, 266 (MNa+).

Alternative Route to Compound 1g

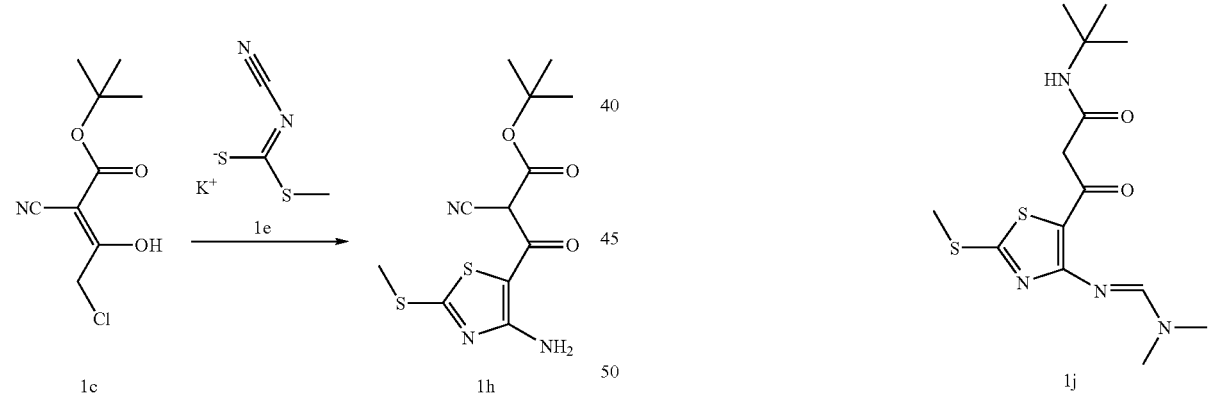

To a stirred solution of 4-chloro-2-cyano-3-hydroxy-but-2-enoic acid tert-butyl ester Compound 1c (51.3 g, 236 mmol) at 0° C. in acetone (750 mL) was added potassium methyl N-cyanodithioimidocarbonate Compound 1e (40.2 g, 236 mmol). After 1 hr the reaction was allowed to warm to RT. The reaction mixture was evaporated down after stirring for 18 hrs. The resulting residue was extracted with ethyl acetate from saturated NaHCO3. The combined organic layers were dried over MgSO4 and the solvent removed under reduced pressure to yield a tan foam, 3-(4-amino-2-methylsulfanyl-thiazol-5-yl)-2-cyano-3-oxo-propionic acid tert-butyl ester Compound 1h, 72.2 g. $^1$H NMR (CDCl3) δ 4.34 (br s, 2H), 3.14 (br s, 1H), 2.70 (br s, 3H), 1.47 (br s, 9H). MS 314 (MH+).

A mixture of 3-(4-amino-2-methylsulfanyl-thiazol-5-yl)-2-cyano-3-oxo-propionic acid tert-butyl ester Compound 1h (72.1 g, 230 mmol), N,N-dimethylformamide dimethyl acetal (65.3 mL, 460 mmol, 94% purity) and DMF (400 mL) were combined and heated to 80° C. for 2 hrs. The cooled reaction was diluted with water and extracted with ethyl acetate. The combined organic extracts were then washed with a brine solution and dried over MgSO4. The solvent was removed under reduced pressure to give a dark brown foam Compound 1i. MS 369 (MH+).The foam was dissolved in DCM (200 mL) and cooled to 0° C. for the dropwise addition of TFA (200 mL). The reaction was stirred at RT for 3 hrs and then evaporated down to provide N-tert-butyl-3-[4-(dimethylamino-methyleneamino)-2-methylsulfanyl-thiazol-5-yl]-3-oxo-propionamide Compound 1j. MS 343 (MH+).

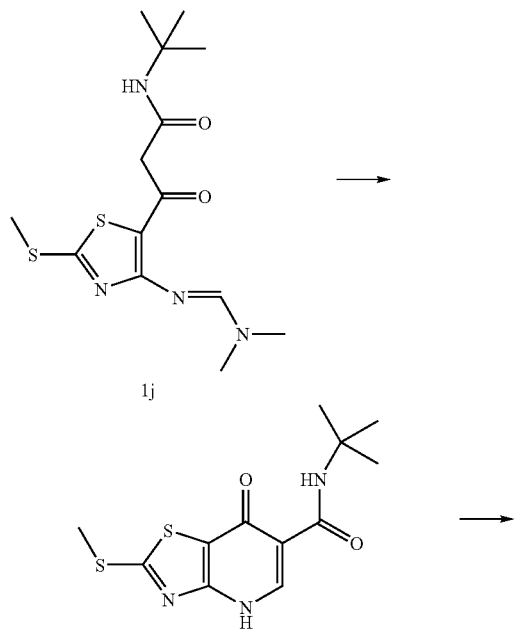

1j

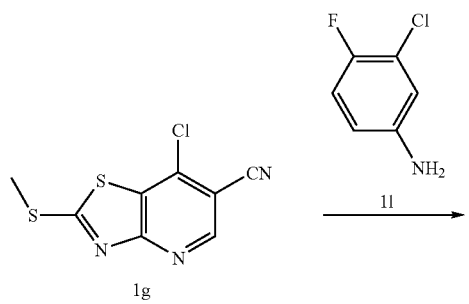

A7

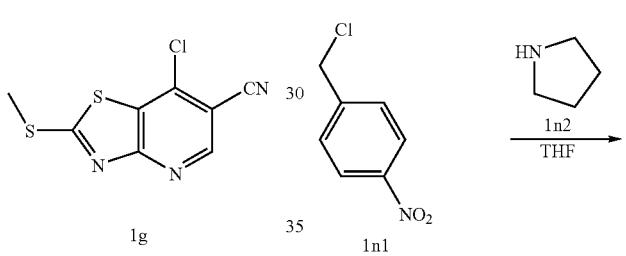

1g

The crude material, Compound 1j, was dissolved in IPA (500 mL) and refluxed for 6 hrs. The solvent was removed under reduced pressure to provide 2-methylsulfanyl-7-oxo-4,7-dihydro-thiazolo[4,5-b]pyridine-6-carboxylic acid tert-butylamide Compound 1k. MS 298 (MH+).

The crude material was dissolved up in DMF (500 mL), cooled to 0° C., and SOCl$_2$ added dropwise (84 mL, 1.15 mol). The reaction mixture was stirred for 18 hrs then diluted with water and extracted with ether. The combined organic extracts were filtered through Celite 545 and then washed with water. The filtered organic solution was then dried over MgSO$_4$ and concentrated down to 200 mL. The tan solid, Compound 1g, precipitated upon addition of MeOH was collected and washed consecutively with MeOH and hexane, 10.1 g. The spectral data was identical for both routes to form Compound 1g.

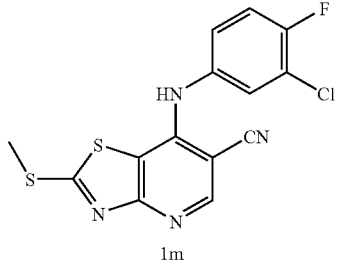

1m

Compound 1g (2.30 g, 9.54 mmol) was combined with 3-chloro-4-fluoro-phenylamine Compound 1l (1.39 g, 9.54 mmol) in IPA (15 mL) in a sealed vessel and heated for 4 h at 145° C. The precipitate formed upon cooling was collected by filtration and subsequently washed with MeOH and hexane to provide 7-(3-chloro-4-fluoro-phenylamino)-2-methylsulfanyl-thiazolo[4,5-b]pyridine-6-carbonitrile Compound 1m (2.1 g) as a tan solid. $^1$H NMR (DMSO-d6) δ 9.77 (s, 1H), 8.66 (s, 1H), 7.55 (dd, J=6.6, 2.8 Hz, 1H), 7.48 (t, J=8.9 Hz, 1H), 7.30 (ddd, J=8.9, 4.3, 2.8 Hz, 1H), 2.74 (s, 3H). MS 351, 353 (MH+).

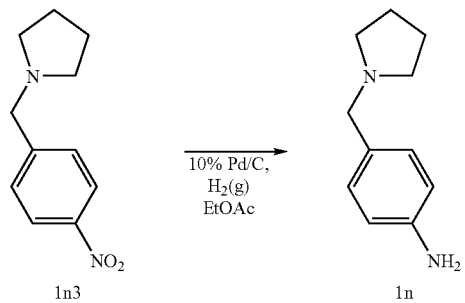

4-nitrobenzyl chloride Compound 1n1 (4.0 g, 23.3 mmol) and pyrrolidine Compound 1n2 (4.8 mL, 58.3 mmol) were combined in THF (50 mL) at ambient temperature. After 18 hr, the reaction was diluted with 10% NH$_4$Cl and extracted with EtOAc. The combined organic layers were dried over MgSO$_4$, filtered and evaporated in vacuo to provide 1-(4-nitrobenzyl)-pyrrolidine Compound 1n3 (4.7 g) as a pale yellow oil without further purification (prepared as described in Mitsuru Shiraishi, et al., *J. Med. Chem.*, 2000, 43, 2049-2063). $^1$H NMR (CDCl$_3$) δ 8.17 (d, J=8.6 Hz, 2H); 7.51 (d, J=8.6 Hz, 2H); 3.72 (s, 2H); 2.58-2.48 (m, 4H); 1.89-1.72 (m, 4H).

10% Pd/C (500 mg) was added to a solution of 1-(4-nitrobenzyl)-pyrrolidine Compound 1n3 (4.56 g, 22.1 mmol) in EtOAc (20 mL). The mixture was hydrogenated at 50 PSI for a period of 2 hrs and filtered through Celite. The filtrate was evaporated and the residue was dissolved in 10% NH$_4$Cl and washed with ethyl ether. The aqueous layer was then adjusted to pH 10 with NaOH and extracted with EtOAc. The combined organic layers were dried over MgSO₄, filtered and evaporated in vacuo to give 4-pyrrolidin-1-ylmethyl-phenylamine Compound 1n (3.05 g) as a light brown oil. ¹H NMR (CDCl₃) δ 7.10 (d, J=8.5 Hz, 2H); 6.63 (d, J=8.5 Hz, 2H); 3.60 (br s, 2H); 3.50 (s, 2H); 2.52-2.42 (m, 4H); 1.83-1.69 (m, 4H).

7.35 (ddd, J=8.8, 4.3, 2.6 Hz, 1H), 4.29 (s, 2H), 3.40-3.25 (m, 2H), 3.11-2.9 (m, 2H), 2.09-1.80 (m, 4H). MS 479, 481 (MH⁺).

EXAMPLE 2

7-(3-chloro-4-fluoro-phenylamino)-2-[4-(2-ethyl-imidazol-1-ylmethyl)-phenylamino]-thiazolo[4,5-b]pyridine-6-carbonitrile (Cpd 1)

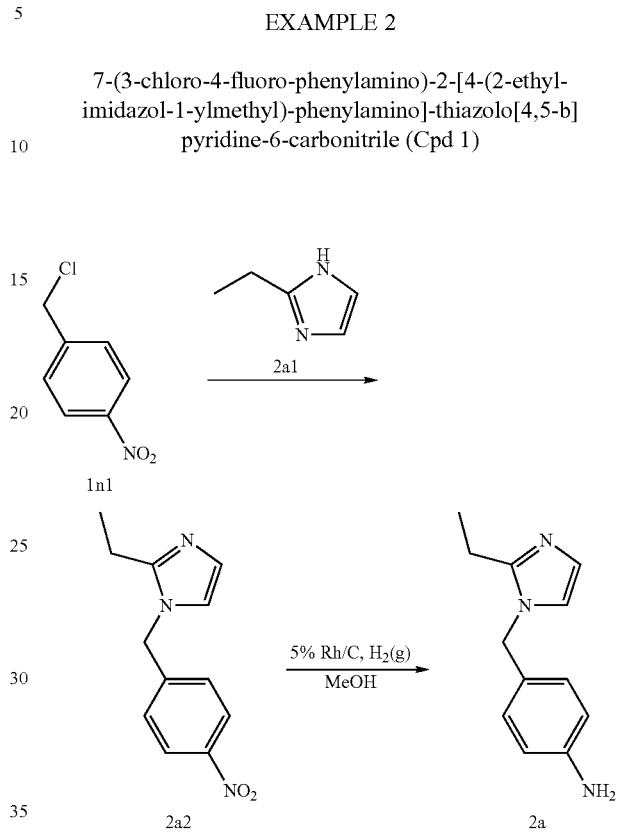

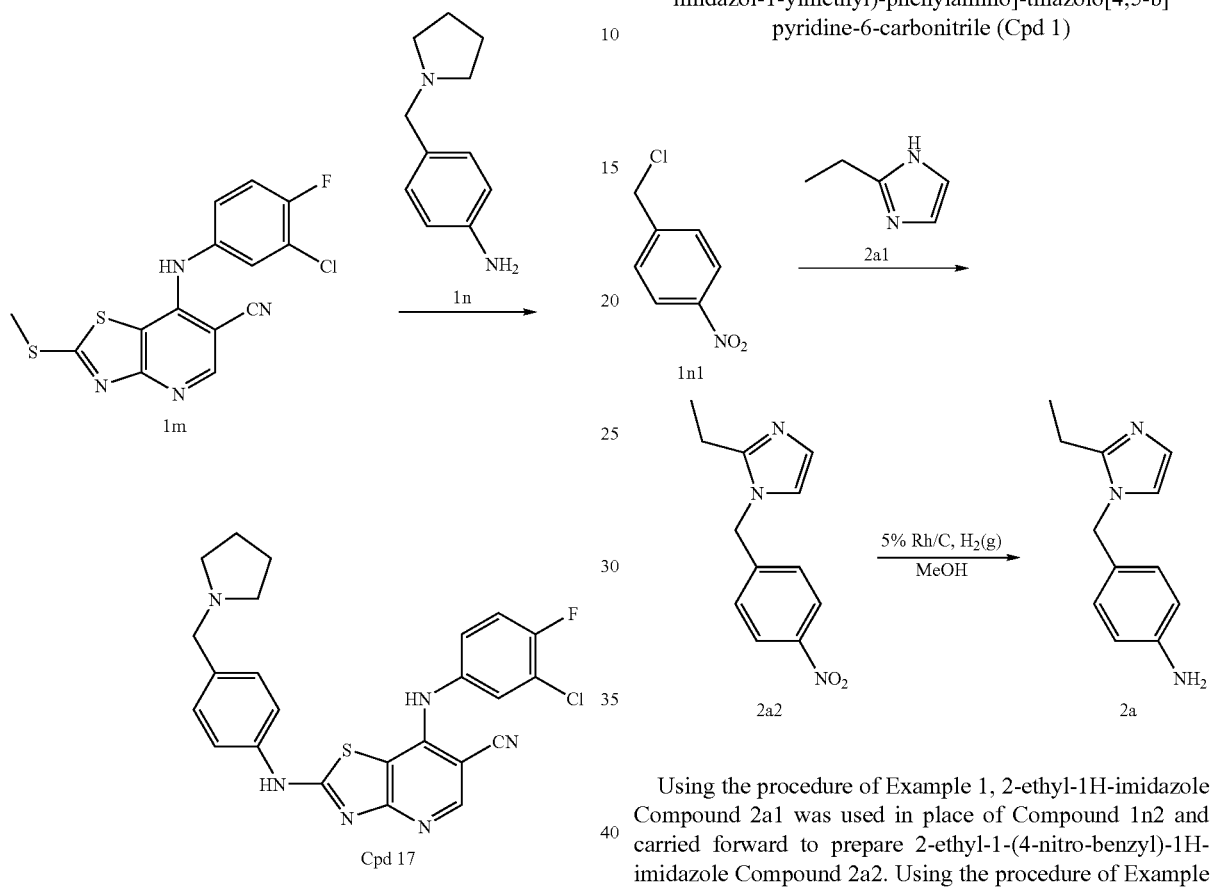

MCPBA (1.36 g, 6.06 mmol, 77% purity) was added to a solution of Compound 1m (1.06 g, 3.03 mmol) in CHCl₃ (30 mL) at 0° C. The reaction was diluted after 2 hr with a saturated solution of NaHCO₃ and extracted with DCM. The organic extracts were combined, dried over MgSO₄ and concentrated in vacuo to provide 7-(3-chloro-4-fluoro-phenylamino)-2-methanesulfinyl-thiazolo[4,5-b]pyridine-6-carbonitrile as an intermediate. MS 367 (MH⁺). AcOH (30 mL) and 4-pyrrolidin-1-ylmethyl-phenylamine Compound 1n (480 mg, 2.73 mmol) were added to the residue. The mixture was stirred for 2 hr, the solvent was evaporated and the residue was partitioned between EtOAc and saturated NaHCO₃. The mixture was extracted with EtOAc, dried (MgSO₄), filtered and concentrated in vacuo to provide a yellow solid. The solid was dissolved in MeOH, treated with an excess of a 2M HCl-ether solution and recrystallized from MeOH/ether to provide 7-(3-chloro-4-fluoro-phenylamino)-2-(4-pyrrolidin-1-ylmethyl-phenylamino)-thiazolo[4,5-b]pyridine-6-carbonitrile Compound 17 (708 mg) as a bis-hydrochloride salt. ¹H NMR (DMSO-d6) δ 11.52 (br s, 1H), 10.97 (br s, 1H), 9.99 (br s, 1H), 8.71 (s, 1H), 7.80 (d, J=8.6 Hz, 2H), 7.64 (d, J=8.6 Hz, 2H), 7.59 (dd, J=6.8, 2.6 Hz, 1H), 7.54 (t, J=8.8 Hz, 1H), Using the procedure of Example 1, 2-ethyl-1H-imidazole Compound 2a1 was used in place of Compound 1n2 and carried forward to prepare 2-ethyl-1-(4-nitro-benzyl)-1H-imidazole Compound 2a2. Using the procedure of Example 21, Compound 2a2 was used in place of Compound 21a2 and carried forward to prepare 4-(2-ethyl-imidazol-1-ylmethyl)-phenylamine Compound 2a.

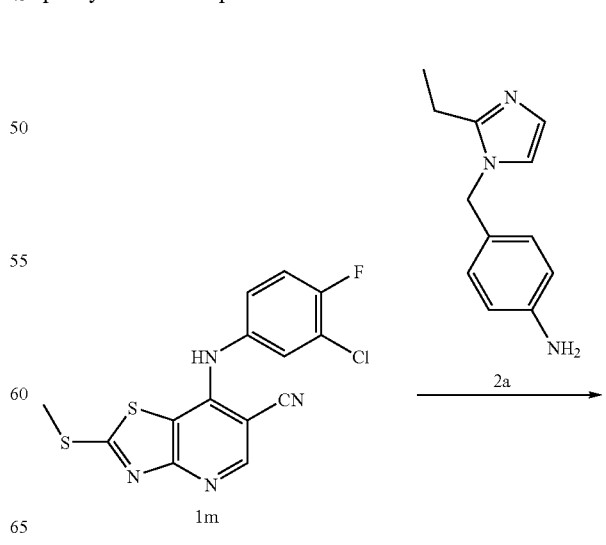

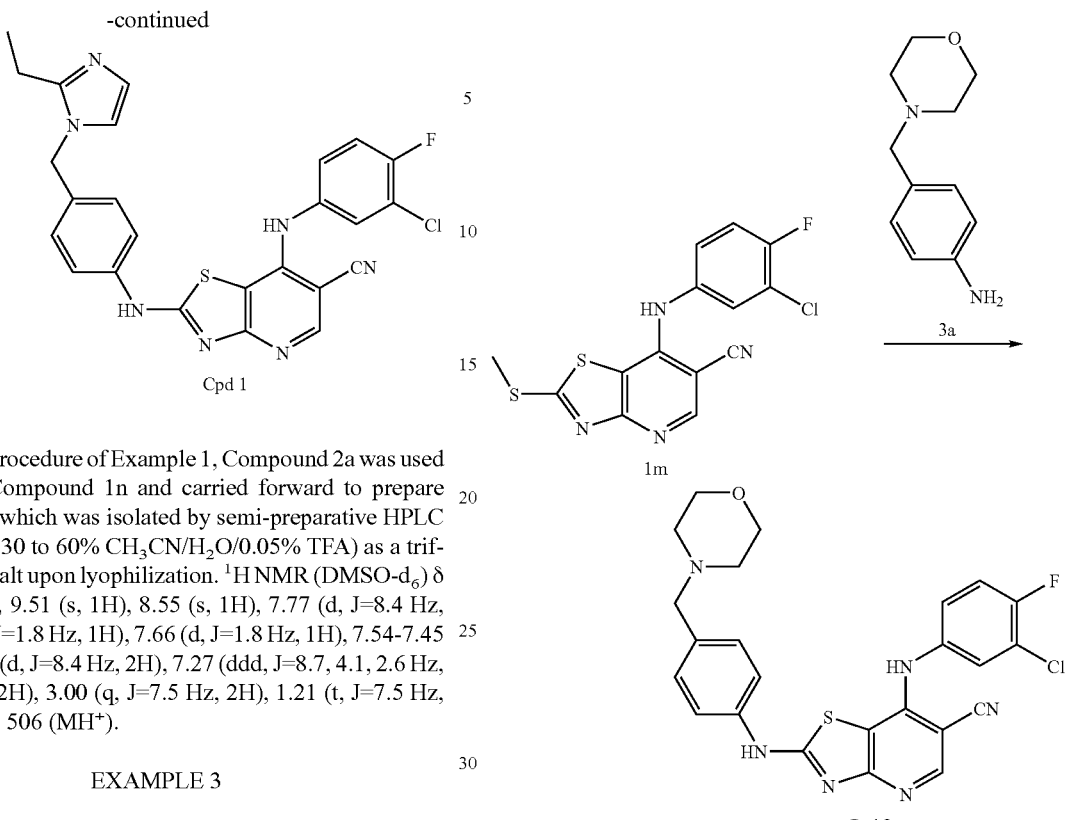

Using the procedure of Example 1, Compound 2a was used in place of Compound 1n and carried forward to prepare Compound 1 which was isolated by semi-preparative HPLC ($C^{18}$ column, 30 to 60% $CH_3CN/H_2O$/0.05% TFA) as a trifluoroacetate salt upon lyophilization. $^1$H NMR (DMSO-$d_6$) δ 10.95 (s, 1H), 9.51 (s, 1H), 8.55 (s, 1H), 7.77 (d, J=8.4 Hz, 2H), 7.70 (d, J=1.8 Hz, 1H), 7.66 (d, J=1.8 Hz, 1H), 7.54-7.45 (m, 2H), 7.37 (d, J=8.4 Hz, 2H), 7.27 (ddd, J=8.7, 4.1, 2.6 Hz, 1H), 5.38 (s, 2H), 3.00 (q, J=7.5 Hz, 2H), 1.21 (t, J=7.5 Hz, 3H). MS 504, 506 (MH$^+$).

EXAMPLE 3

7-(3-chloro-4-fluoro-phenylamino)-2-(4-morpholin-4-ylmethyl-phenylamino)-thiazolo[4,5-b]pyridine-6-carbonitrile (Cpd 2)

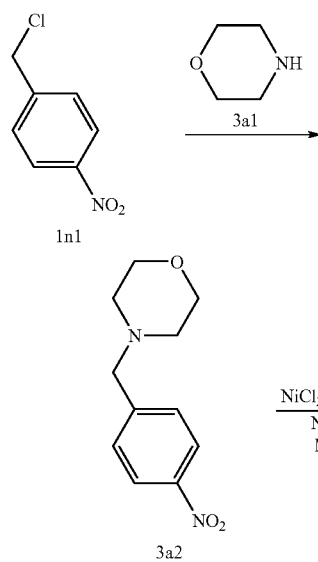

Using the procedure of Example 1, morpholine Compound 3a1 was used in place of Compound 1n2 and carried forward to prepare 4-(4-nitro-benzyl)-morpholine Compound 3a2. Using the procedure of Example 46, Compound 3a2 was used in place of Compound 46a2 and carried forward to prepare 4-morpholin-4-ylmethyl-phenylamine Compound 3a.

Using the procedure of Example 1, Compound 3a was used in place of Compound 1n and carried forward to prepare Compound 2 which was recrystallized from methanol/EtOAc as a bis-hydrochloride salt, a yellow solid. $^1$H NMR (DMSO-d6) δ 11.30 (br s, 1H), 10.93 (br s, 1H), 9.78 (br s, 1H), 8.65 (s, 1H), 7.82 (d, J=8.4 Hz, 2H), 7.61 (d, J=8.4 Hz, 2H), 7.57 (dd, J=6.2, 2.6 Hz, 1H), 7.54 (t, J=9.0 Hz, 1H), 7.36-7.31 (m, 1H), 4.31 (s, 2H), 3.95 (d, J=10.9 Hz, 2H), 3.76 (t, J=11.8 Hz, 2H), 3.22 (d, J=11.8 Hz, 2H), 3.14-3.01 (m, 2H). MS 495,497 (MH$^+$).

EXAMPLE 4

7-(3-chloro-4-fluoro-phenylamino)-2-(4-dimethylaminomethyl-phenylamino)-thiazolo[4,5-b]pyridine-6-carbonitrile (Cpd 3)

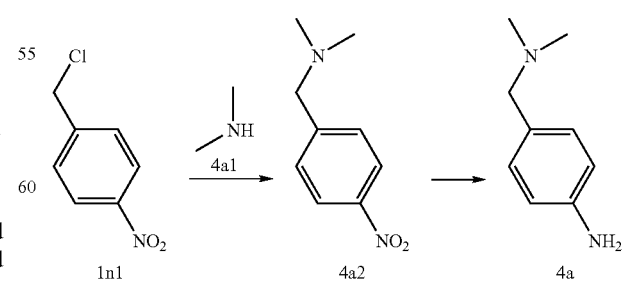

Using the procedure of Example 1, dimethylamine Compound 4a1 was used in place of Compound 1n2 and carried forward to prepare dimethyl-(4-nitrobenzyl)-amine Compound 4a2. Stannous chloride (28.1 g, 148 mmol) was added to a solution of Compound 4a2 (5.33 g, 29.6 mmol) in ethanol (200 mL) and heated to 60° C. Sodium borohydride (0.560 g, 14.8 mmol) in ethanol (80 mL) was added dropwise. Two hrs later the reaction mixture was added to ice water. The slurry was filtered through Celite 545 and the filtrate cake rinsed with ether. The collected liquors were brought to pH 11 with 1N NaOH and extracted with ether. The combined organic layers were washed with water, dried over $MgSO_4$ and filtered. The dried organic solution was then reduced in vacuo to provide 4-dimethylaminomethyl-phenylamine Compound 4a which was used in the next step without further purification. MS 207 ($MH^+$).

Using the procedure of Example 1, Compound 4a was used in place of Compound 1n and carried forward to prepare Compound 3, which was isolated as a trifluoroacetate salt. $^1$H NMR (DMSO-$d_6$) δ 11.03 (br s, 1H), 9.58 (br s, 1H), 9.54 (s, 1H), 8.57 (s, 1H), 7.83 (d, J=8.4 Hz, 2H), 7.56-7.47 (m, 4H), 7.29 (ddd, J=8.9, 4.1, 2.8 Hz, 1H), 4.25 (s, 2H), 2.73 (s, 6H). MS 453, 455 ($MH^+$).

EXAMPLE 5

2-(4-{[bis-(2-methoxy-ethyl)-amino]-methyl}-phenylamino)-7-(3-chloro-4-fluoro-phenylamino)-thiazolo[4,5-b]pyridine-6-carbonitrile (Cpd 4)

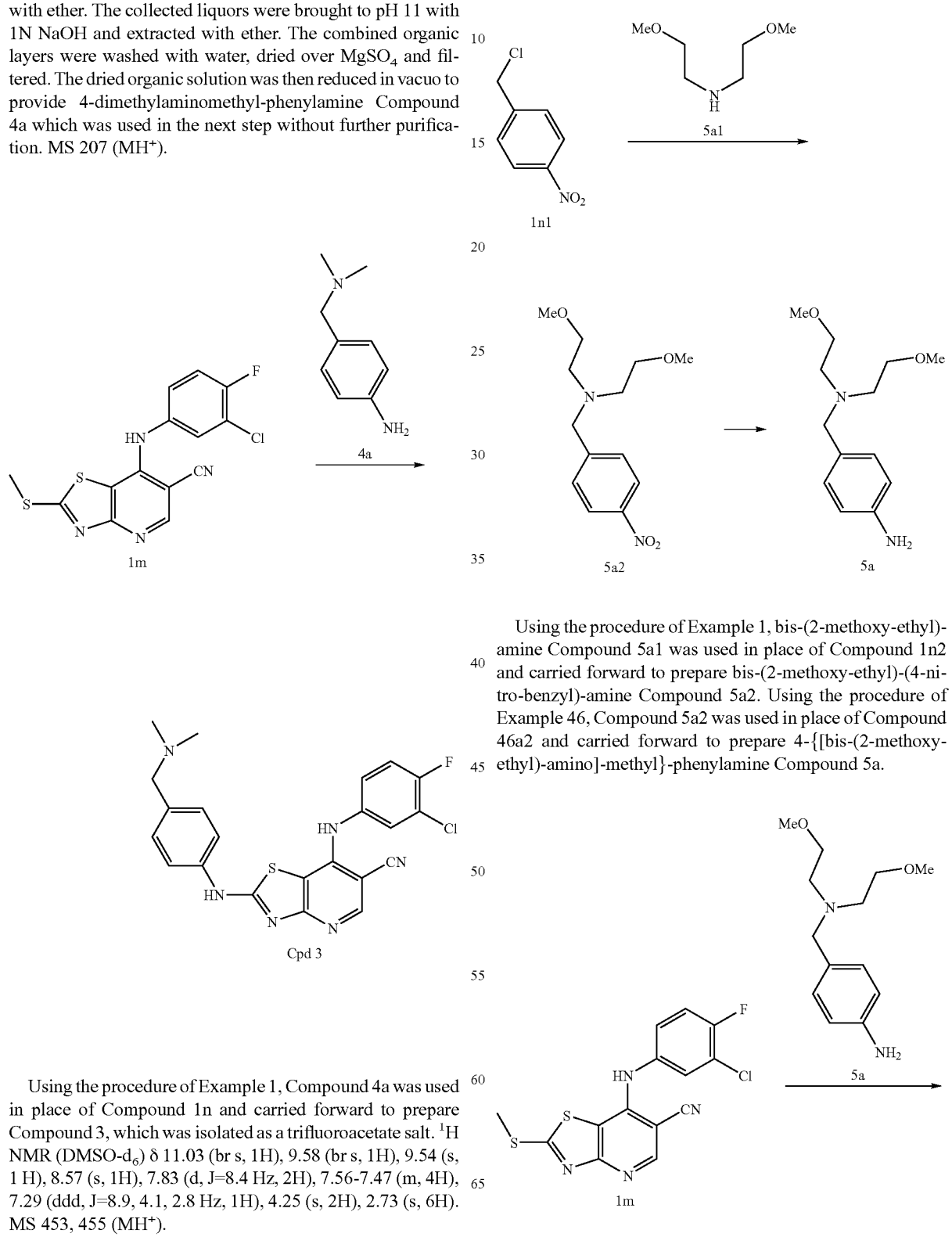

Using the procedure of Example 1, bis-(2-methoxy-ethyl)-amine Compound 5a1 was used in place of Compound 1n2 and carried forward to prepare bis-(2-methoxy-ethyl)-(4-nitro-benzyl)-amine Compound 5a2. Using the procedure of Example 46, Compound 5a2 was used in place of Compound 46a2 and carried forward to prepare 4-{[bis-(2-methoxy-ethyl)-amino]-methyl}-phenylamine Compound 5a.

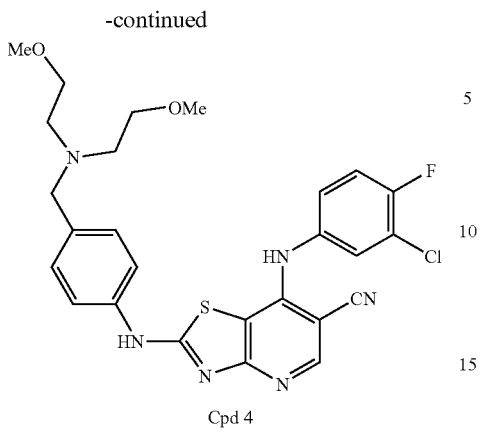

Using the procedure of Example 1, Compound 5a was used in place of Compound 1n and carried forward to prepare Compound 4, which was isolated as a trifluoroacetate salt. $^1$H NMR (DMSO-$d_6$) δ 11.02 (s, 1H), 9.53 (s, 1H), 9.47 (br s, 1H), 8.56 (s, 1H), 7.81 (d, J=8.6 Hz, 2H), 7.59-7.47 (m, 4H), 7.29 (ddd, J=8.7, 4.1, 2.7 Hz, 1H), 4.36 (s, 2H), 3.75-3.53 (m, 8H), 3.30 (s, 6H). MS 541, 534 (MH$^+$).

EXAMPLE 6

4-[7-(3-chloro-4-fluoro-phenylamino)-6-cyano-thiazolo[4,5-b]pyridin-2-ylamino]-N,N-bis-(2-methoxy-ethyl)-benzenesulfonamide (Cpd 5)

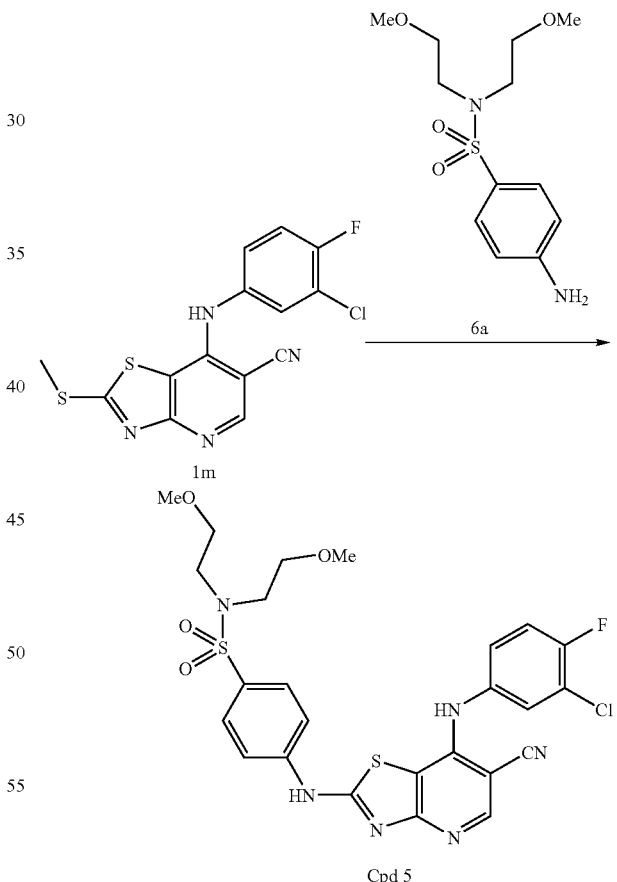

Using the procedure of Example 1, 4-nitro-benzenesulfonyl chloride Compound 6a1, used in place of Compound 1n1, and bis-(2-methoxy-ethyl)-amine Compound 5a1, used in place of Compound 1n2, were carried forward to prepare N,N-bis-(2-methoxy-ethyl)-4-nitro-benzenesulfonamide Compound 6a2. Using the procedure of Example 1, Compound 6a2 was used in place of Compound 1n3 and carried forward to prepare 4-amino-N,N-bis-(2-methoxy-ethyl)-benzenesulfonamide Compound 6a.

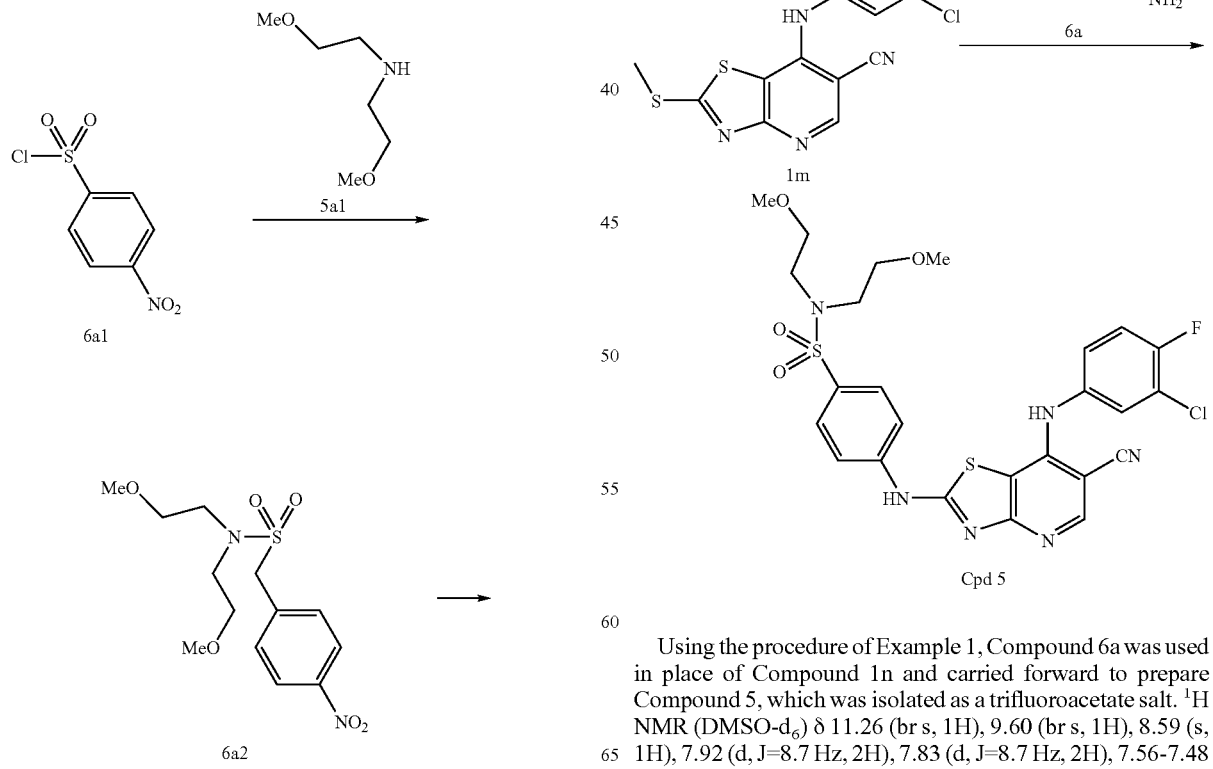

Using the procedure of Example 1, Compound 6a was used in place of Compound 1n and carried forward to prepare Compound 5, which was isolated as a trifluoroacetate salt. $^1$H NMR (DMSO-$d_6$) δ 11.26 (br s, 1H), 9.60 (br s, 1H), 8.59 (s, 1H), 7.92 (d, J=8.7 Hz, 2H), 7.83 (d, J=8.7 Hz, 2H), 7.56-7.48 (m, 2H), 7.31 (ddd, J=8.7, 4.3, 2.7 Hz, 1H), 3.41 (t, J=5.9 Hz, 4H), 3.27 (t, J=5.9 Hz, 4H), 3.20 (s, 6H). MS 591, 593 (MH$^+$).

EXAMPLE 7

4-[7-(3-chloro-4-fluoro-phenylamino)-6-cyano-thiazolo[4,5-b]pyridin-2-ylamino]-N-(2-morpholin-4-yl-ethyl)-benzenesulfonamide (Cpd 7)

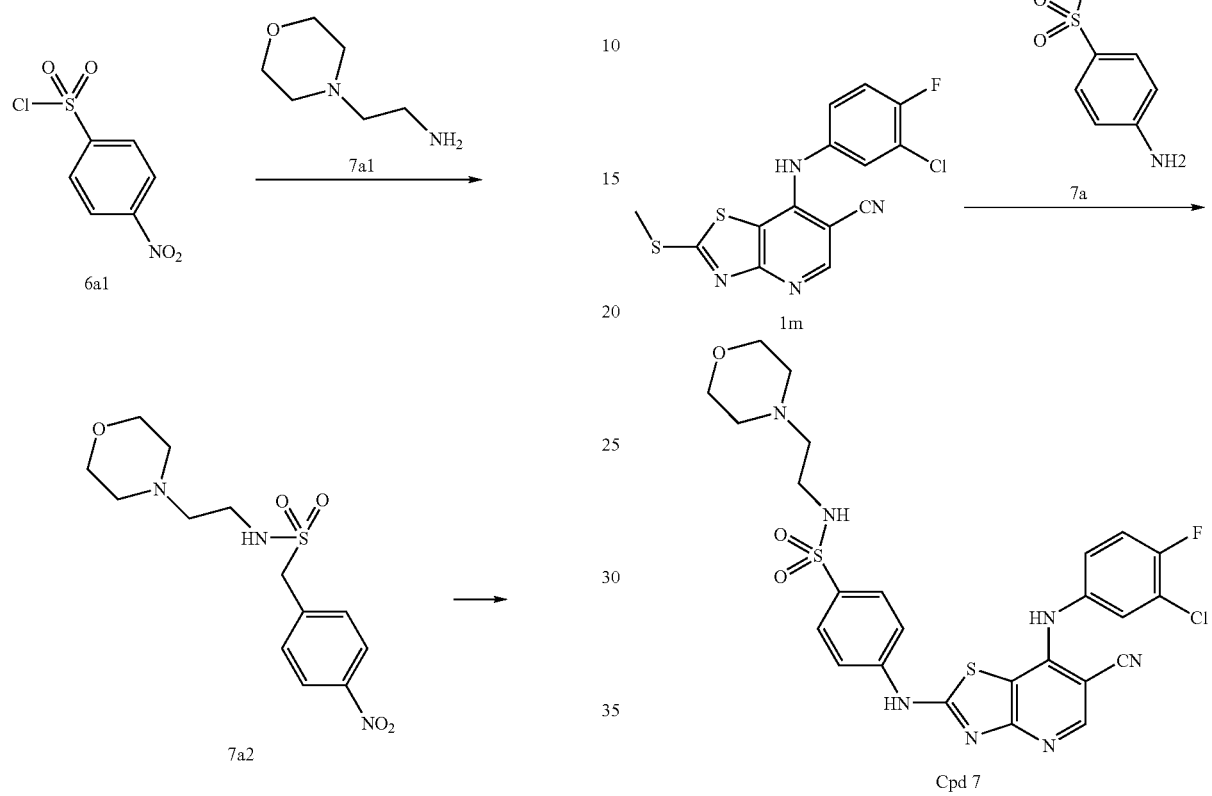

Using the procedure of Example 1, 4-nitro-benzenesulfonyl chloride Compound 6a1, used in place of Compound 1n1, and 2-morpholin-4-yl-ethylamine Compound 7a1, used in place of Compound 1n2, were carried forward to prepare N-(2-morpholin-4-yl-ethyl)-4-nitro-benzenesulfonamide Compound 7a2. Using the procedure of Example 1, Compound 7a2 was used in place of Compound 1n3 and carried forward to prepare 4-amino-N-(2-morpholin-4-yl-ethyl)-benzenesulfonamide Compound 7a.

Using the procedure of Example 1, Compound 7a was used in place of Compound 1n and carried forward to prepare Compound 7, which was isolated as a trifluoroacetate salt. $^1$H NMR (DMSO-$d_6$) δ 11.28 (s, 1H), 9.84 (br s, 1H), 9.59 (s, 1H), 8.59 (s, 1H), 8.01-7.82 (m, 4H), 7.58-748 (m, 2H), 7.31 (ddd, J=8.9, 4.2, 2.8 Hz, 1H), 4.10-3.91 (m, 4H), 3.51-3.34 (m, 2H), 3.30-3.03 (m, 6H). MS 588, 590 (MH$^+$).

EXAMPLE 8

7-(3-chloro-4-fluoro-phenylamino)-2-{4-[(2S)-2-hydroxymethyl-pyrrolidin-1-ylmethyl]-phenylamino}-thiazolo[4,5-b]pyridine-6-carbonitrile (Cpd 6)

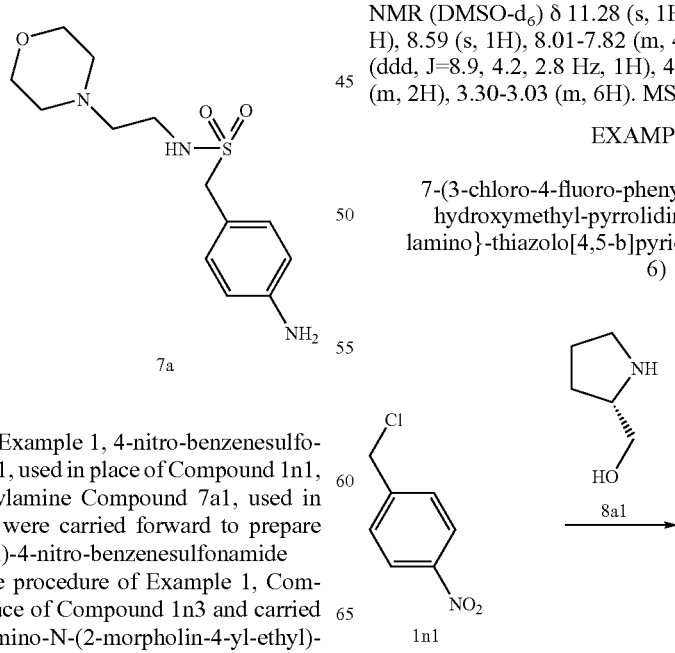

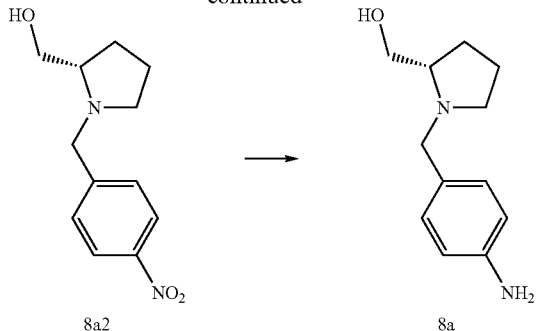

Using the procedure of Example 1, (2S)-2-hydroxymethyl-pyrrolidine Compound 8a1 was used in place of Compound 1n2 and carried forward to prepare 4-[(2S)-2-hydroxymethyl-pyrrolidin-1-ylmethyl]-phenylamine Compound 8a.

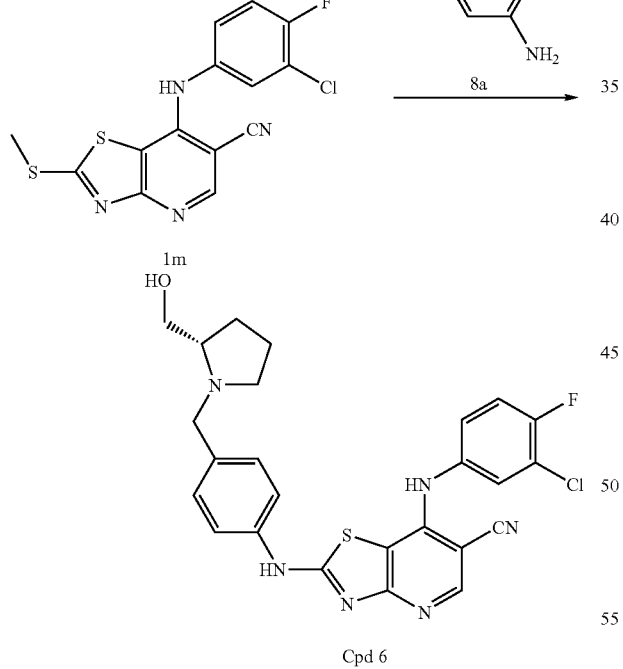

Using the procedure of Example 1, Compound 8a was used in place of Compound 1n and carried forward to prepare Compound 6, which was isolated as a trifluoroacetate salt. $^1$H NMR (DMSO-d$_6$) δ 11.03 (s, 1H), 9.54 (s, 1H), 9.40 (br s, 1 H), 8.57 (s, 1H), 7.81 (d, 8.5 Hz, 2H), 7.58-7.47 (m, 4H), 7.29 (ddd, J=8.9, 4.2, 2.7 Hz, 1H), 5.53 (br s, 1H), 4.96 (dd, J=13.0, 3.8 Hz, 1H), 4.25 (dd, J=13.0, 6.3 Hz, 1 H), 3.58 (s, 2H), 3.35-3.10 (m, 2H), 2.18-2.05 (m, 1H), 2.04-1.91 (m, 1H), 1.88-1.68 (m, 2H). MS 509, 511 (MH$^+$).

EXAMPLE 9

7-(3-chloro-4-fluoro-phenylamino)-2-(3-morpholin-4-yl-propylamino)-thiazolo[4,5-b]pyridine-6-carbonitrile (Cpd 8)

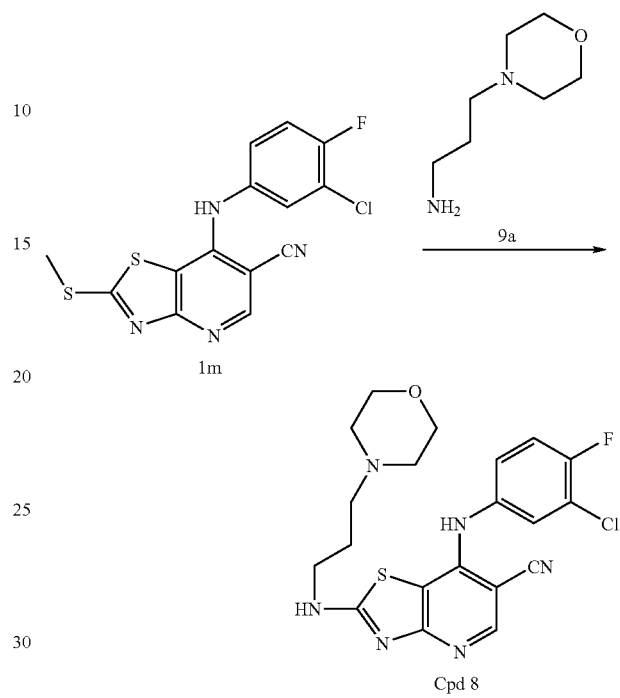

Using the procedure of Example 1, 3-morpholin-4-yl-propylamine Compound 9a was used in place of Compound 1n and carried forward to prepare Compound 8, which was isolated as a trifluoroacetate salt. $^1$H NMR (DMSO-d$_6$) δ 9.69 (br s, 1H), 9.38 (s, 1H), 8.76 (t, J=5.3 Hz, 1H), 8.48 (s, 1H), 7.48 (t, J=8.9 Hz, 1H), 7.42 (dd, J=6.5, 2.7 Hz, 1H), 7.21 (ddd, J=8.9, 4.1, 2.7 Hz, 1H), 3.99 (br d, J=12.2 Hz, 2H), 3.73-3.45 (m, 6H), 3.22-2.95 (m, 4H), 2.03-1.89 (m, 2H). MS 447, 449 (MH$^+$).

EXAMPLE 10

7-(3-chloro-4-fluoro-phenylamino)-2-[(4-{methyl-[(2R)-tetrahydro-furan-2-ylmethyl]-amino}-methyl)-phenylamino]-thiazolo[4,5-b]pyridine-6-carbonitrile (Cpd 14)

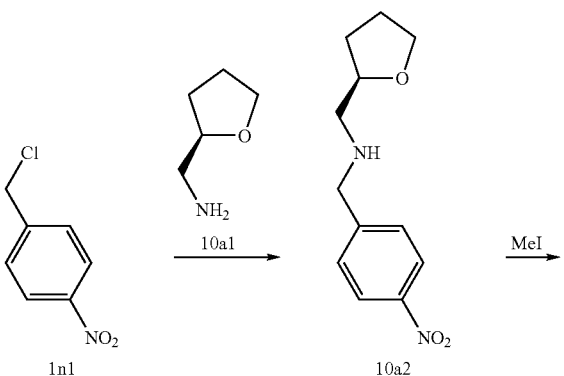

-continued

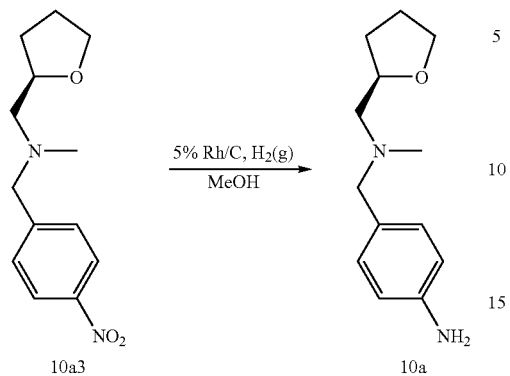

Using the procedure of Example 1, (R)-(–)-tetrahydrofurfurylamine Compound 10a1 was used in place of Compound 1n2 and carried forward to prepare (4-nitro-benzyl)-[(2R)-tetrahydro-furan-2-ylmethyl]-amine Compound 10a2.

Methyl iodide (0.728 mL, 11.7 mmol) was added to (4-nitro-benzyl)-[(2R)-tetrahydro-furan-2-ylmethyl]-amine Compound 10a2 (1.84 g, 7.80 mmol) and potassium carbonate (3.23 g, 23.4 mmol) in DMF (30 mL). After 4 hrs the reaction was diluted with water and extracted with ethyl ether. The combined extracts were washed with water, dried over $MgSO_4$, and evaporated down to give 1.43 g of methyl-(4-nitro-benzyl)-[(2R)-tetrahydro-furan-2-ylmethyl]-amine Compound 10a3. Using the procedure of Example 21, Compound 10a3 was used in place of Compound 21a2 and carried forward to prepare 4-({methyl-[(2R)-tetrahydro-furan-2-ylmethyl]-amino}-methyl)-phenylamine Compound 10a.

-continued

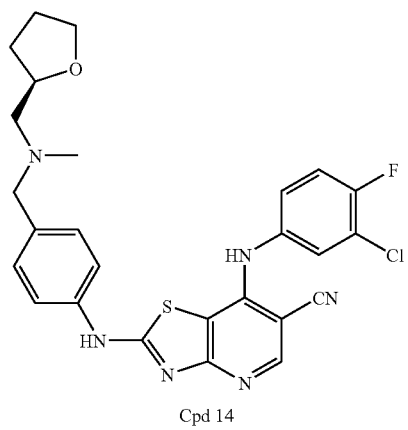

Using the procedure of Example 1, Compound 10a was used in place of Compound 1n and carried forward to prepare Compound 14, which was isolated as a trifluoroacetate salt. $^1$H NMR (DMSO-$d_6$) δ 9.38 (br s, 1H), 8.41 (s, 1H), 7.74-7.58 (m, 3H), 7.43-7.31 (m, 3H), 7.30-7.12 (m, 2H), 4.34-3.99 (m, 3H), 3.84-3.60 (m, 2H), 3.26-2.83 (m, 2H), 2.70 (s, 3H), 2.05-1.91 (m, 1H), 1.85-1.72 (m, 2H), 1.52-1.36 (m, 1H). MS 523,525 (MH$^+$).

EXAMPLE 11

7-(3-chloro-4-fluoro-phenylamino)-2-[(4-{methyl-[(2S)-tetrahydro-furan-2-ylmethyl]-amino}-methyl)-phenylamino]-thiazolo[4,5-b]pyridine-6-carbonitrile (Cpd 15)

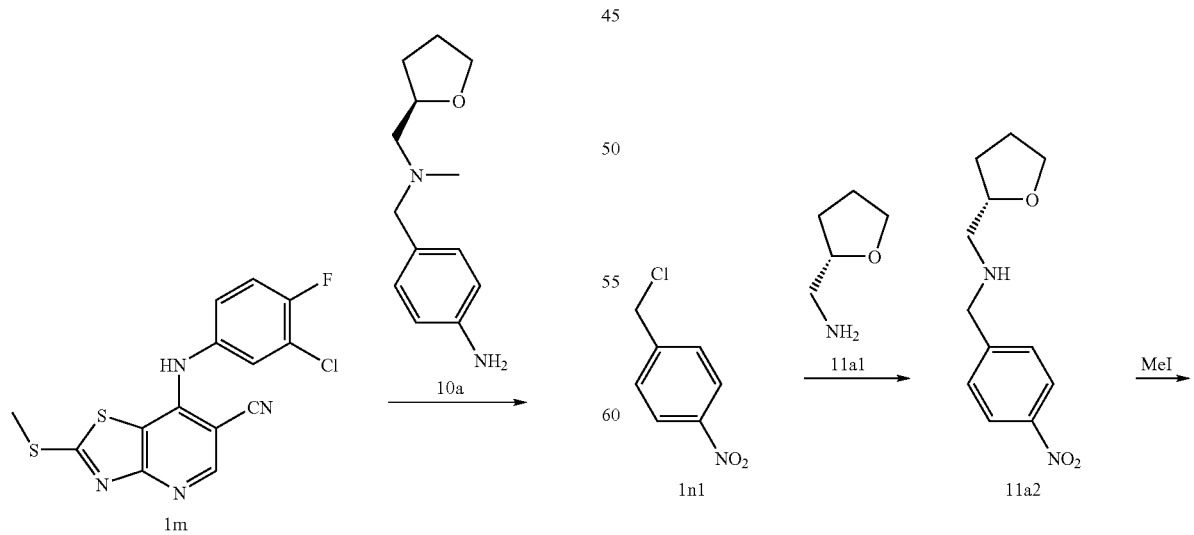

-continued

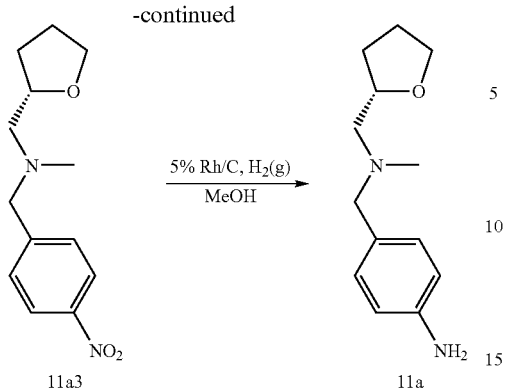

Using the procedure of Example 1, (S)-(+)-tetrahydrofurfurylamine Compound 11a1 was used in place of Compound 1j2 and carried forward to prepare (4-nitro-benzyl)-[(2S)-tetrahydro-furan-2-ylmethyl]-amine Compound 11a2. Using the procedure of Example 10, Compound 11a2, replacing Compound 10a2, was carried forward to give Compound 11a3. Using the procedure of Example 21, Compound 11a3 was used in place of Compound 21a2 and carried forward to prepare 4-({methyl-[(2S)-tetrahydro-furan-2-ylmethyl]-amino}-methyl)-phenylamine Compound 11a.

Using the procedure of Example 1, Compound 11a was used in place of Compound 1n and carried forward to prepare Compound 15, which was isolated as a trifluoroacetate salt. $^1$H NMR (DMSO-$d_6$) δ 9.40 (br s, 1H), 8.80 (br s, 1H), 8.42 (s, 1H), 7.81-7.62 (m, 3H), 7.42-7.32 (m, 3H), 7.31-7.14 (m, 2H), 4.36-3.99 (m, 3H), 3.87-3.61 (m, 2H), 3.26-2.83 (m, 2H), 2.70 (s, 3H), 2.05-1.92 (m, 1H), 1.85-1.72 (m, 2H), 1.54-1.37 (m, 1H). MS 523,525 (MH$^+$).

EXAMPLE 12

7-(3-chloro-4-fluoro-phenylamino)-2-(4-{[methyl-(tetrahydro-pyran-4-yl)-amino]-methyl}-phenylamino)-thiazolo[4,5-b]pyridine-6-carbonitrile (Cpd 16)

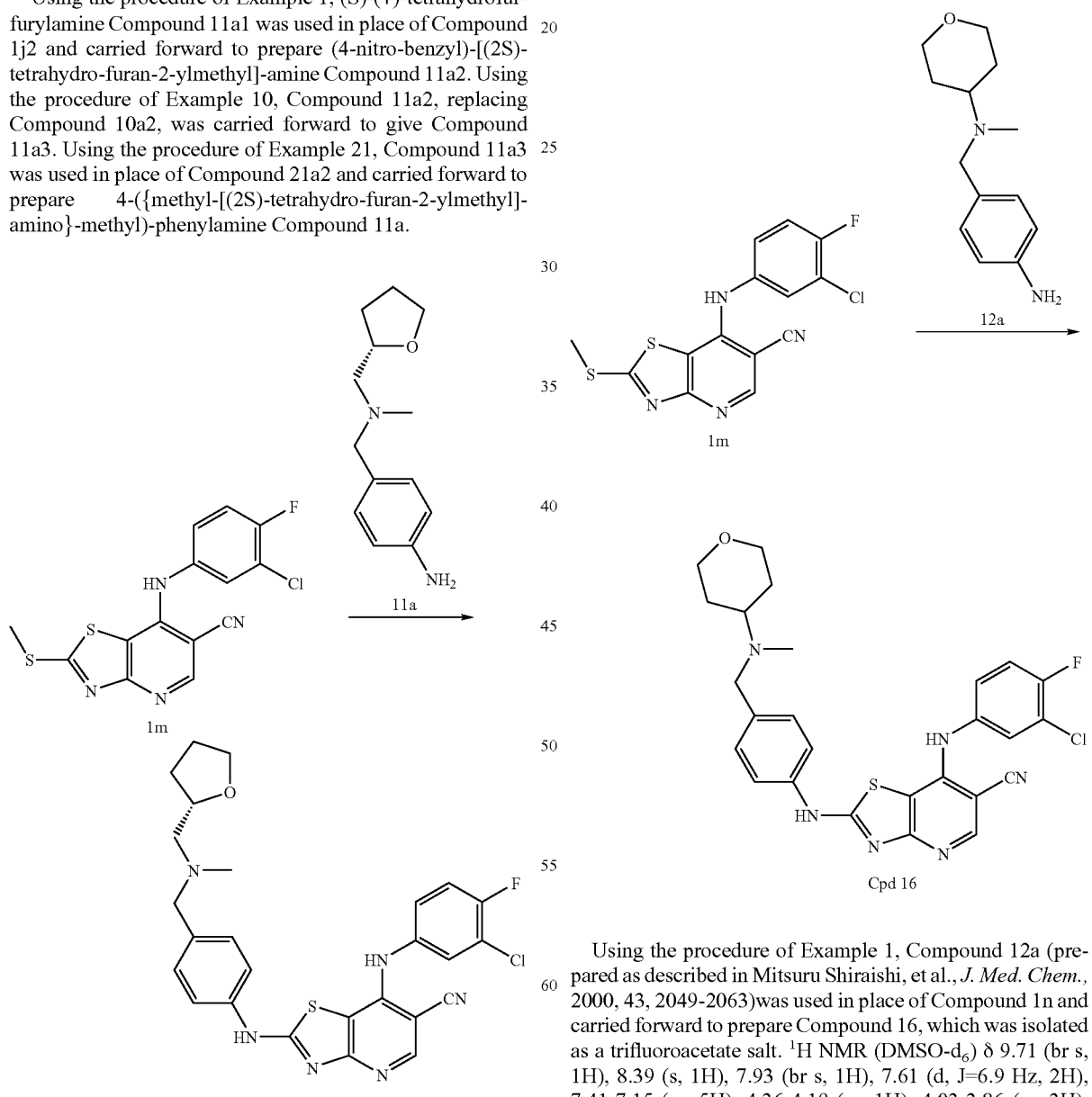

Using the procedure of Example 1, Compound 12a (prepared as described in Mitsuru Shiraishi, et al., *J. Med. Chem.*, 2000, 43, 2049-2063)was used in place of Compound 1n and carried forward to prepare Compound 16, which was isolated as a trifluoroacetate salt. $^1$H NMR (DMSO-$d_6$) δ 9.71 (br s, 1H), 8.39 (s, 1H), 7.93 (br s, 1H), 7.61 (d, J=6.9 Hz, 2H), 7.41-7.15 (m, 5H), 4.36-4.19 (m, 1H), 4.03-3.86 (m, 3H), 3.39-3.19 (m, 3H), 2.51 (s, 3H), 1.98-1.63 (m, 4H). MS 523, 525 (MH$^+$).

EXAMPLE 13

2-(3-chloro-4-dimethylaminomethyl-phenylamino)-7-(3-chloro-4-fluoro-phenylamino)-thiazolo[4,5-b]pyridine-6-carbonitrile (Cpd 18)

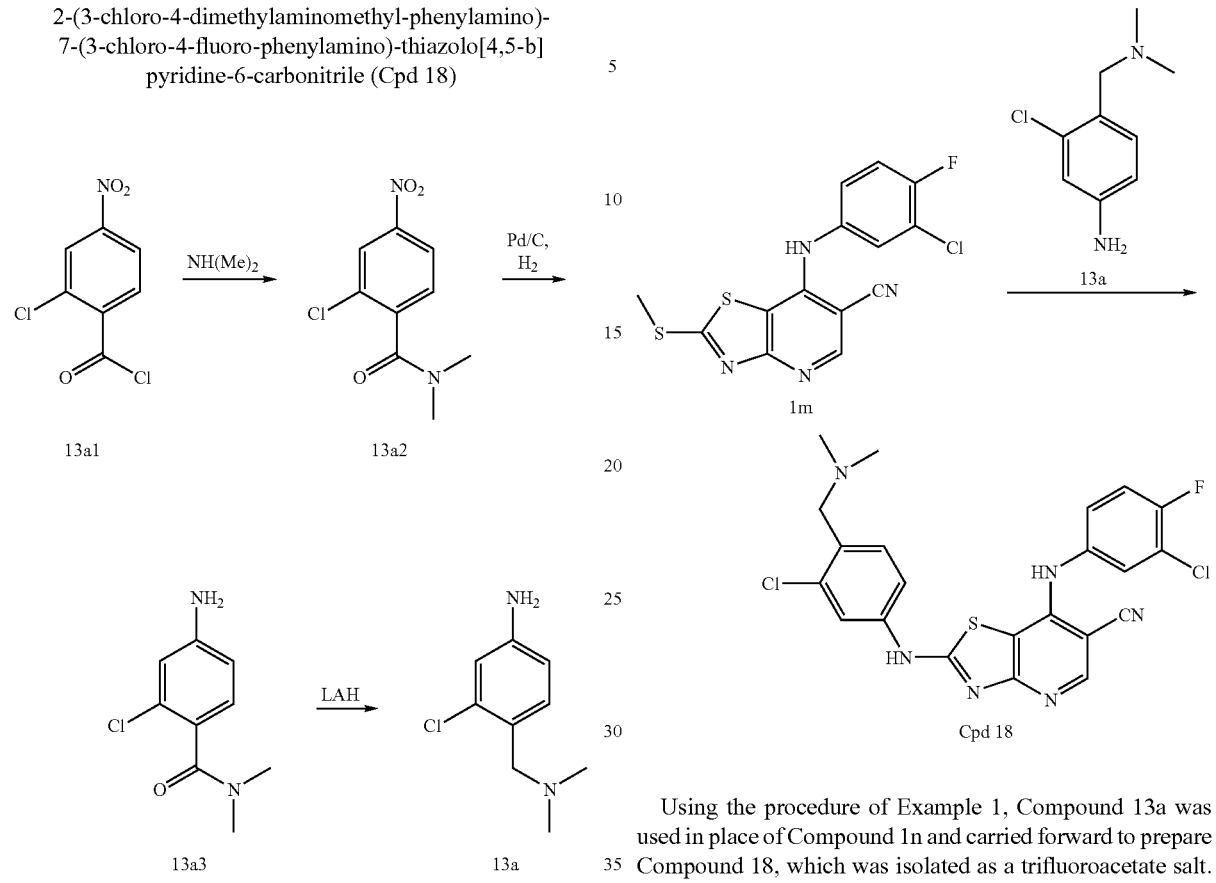

2-chloro-4-nitrobenzoyl chloride Compound 13a1 (7.08 g, 32.2 mmol) and dimethylamine hydrochloride (2.62 g, 32.2 mmol) were combined in THF (50 mL) at 0° C. TEA (8.97 mL, 64.4 mmol) was added and the mixture was heated at reflux for 18 hrs. When the reaction was complete, the mixture was diluted with 1N HCl and extracted with EtOAc. The product was isolated by flash chromatography (30-50% EtOAc/hexane gradient) to provide 2-chloro-N,N-dimethyl-4-nitro-benzamide Compound 13a2 (3.05 g) as a tan solid. MS 229 (MH$^+$).

Using the procedure of Example 1, Compound 13a2 was used in place of Compound 1j3 and carried forward to prepare 4-amino-2-chloro-N,N-dimethyl-benzamide Compound 13a3. 1M LAH (3.53 mL, 3.53 mmol) was added dropwise to a solution of Compound 13a3 (700 mg, 3.53 mmol) in THF (10 mL). After 10 minutes, the reaction was cooled to 0° C. and quenched with water. The mixture was extracted from ethyl ether with 1N HCl. The aqueous layer was adjusted to pH 10 with NaOH and the product was extracted with EtOAc. The combined organic layers were dried over MgSO$_4$ and concentrated to give 3-chloro-4-dimethylaminomethyl-phenylamine Compound 13a (150 mg) as a viscous brown oil. MS 185 (MH$^+$).

Using the procedure of Example 1, Compound 13a was used in place of Compound 1n and carried forward to prepare Compound 18, which was isolated as a trifluoroacetate salt. $^1$H NMR (DMSO-d$_6$) δ 11.23 (s, 1H), 9.69-9.56 (m, 2H), 8.60 (s, 1H), 8.19 (s, 1H), 7.68 (d, J=8.9Hz, 1H), 7.64 (d, J=8.9 Hz, 1H), 7.56 (dd, J=6.6, 2.7 Hz, 1H), 7.53 (t, J=8.9 Hz, 1H), 7.33 (ddd, J=8.9, 4.2, 2.7 Hz, 1H), 4.41 (s, 2H), 2.82 (s, 6H). MS 487, 489, 491 (MH$^+$).

EXAMPLE 14

7-(3-chloro-4-fluoro-phenylamino)-2-[4-({[(2R)-tetrahydro-furan-2-ylmethyl]-amino}-methyl)-phenylamino]-thiazolo[4,5-b]pyridine-6-carbonitrile (Cpd 21)

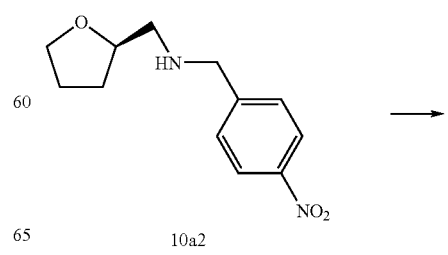

3.08-2.99 (m, 1H), 2.92-2.82 (m, 1H), 2.06-1.95 (m, 1H), 1.91-1.80 (m, 2H), 1.60-1.49 (m, 1H). MS 509, 511 (MH⁺).

EXAMPLE 15

7-(3-chloro-4-fluoro-phenylamino)-2-(4-morpholin-4-ylmethyl-benzylamino)-thiazolo[4,5-b]pyridine-6-carbonitrile (Cpd 22)

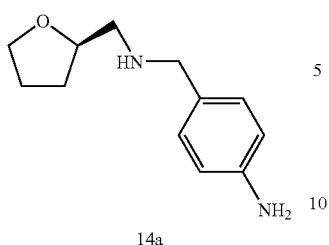

14a

Using the procedure of Example 21, Compound 10a2 (4-nitro-benzyl)-[(2R)-tetrahydro-furan-2-ylmethyl]-amine was used in place of Compound 21a2 and carried forward to prepare 4-({[(2R)-tetrahydro-furan-2-ylmethyl]-amino}-methyl)-phenylamine Compound 14a.

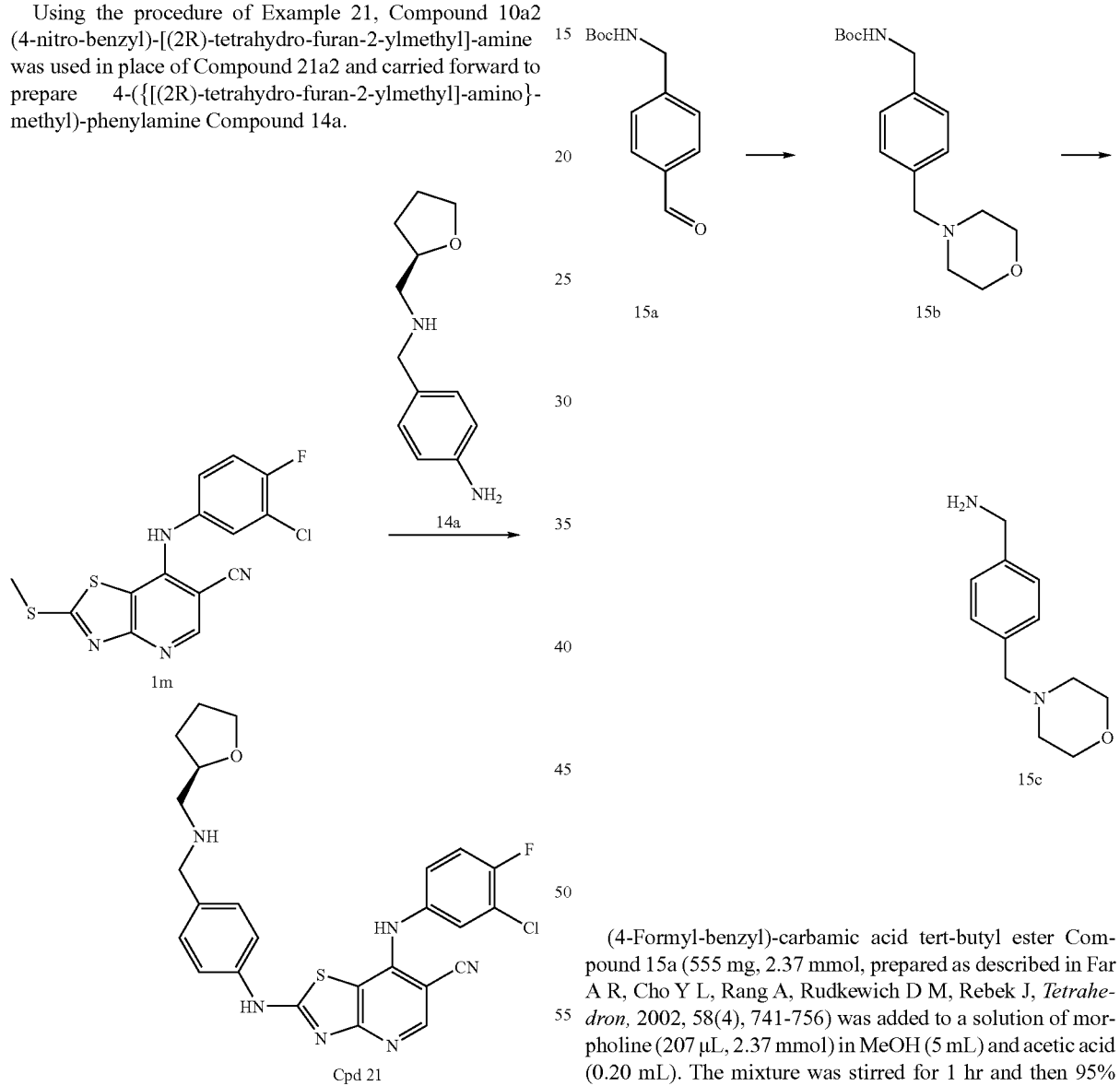

Using the procedure of Example 1, Compound 14a was used in place of Compound 1n and carried forward to prepare Compound 21, which was isolated as a trifluoroacetate salt. ¹H NMR (DMSO-d₆) δ 11.01 (s, 1H), 9.56 (s, 1H), 8.91 (br s, 1H), 8.58 (s, 1H), 7.79 (d, J=8.6 Hz, 2H), 7.55-7.49 (m, 4H), 7.30 (ddd, J=8.8, 4.1, 2.8 Hz, 1H), 4.21-4.06 (m, 3H), 3.82 (dd, J=14.8, 7.4 Hz, 1H), 3.73 (dd, J=14.0, 7.4 Hz, 1H), (4-Formyl-benzyl)-carbamic acid tert-butyl ester Compound 15a (555 mg, 2.37 mmol, prepared as described in Far A R, Cho Y L, Rang A, Rudkewich D M, Rebek J, *Tetrahedron*, 2002, 58(4), 741-756) was added to a solution of morpholine (207 µL, 2.37 mmol) in MeOH (5 mL) and acetic acid (0.20 mL). The mixture was stirred for 1 hr and then 95% NaBH₃CN (198 mg, 3.0 mmol) was added. The reaction was diluted after 2 hr with saturated NaHCO₃ and extracted with EtOAc to provide (4-morpholin-4-ylmethyl-benzyl)-carbamic acid tert-butyl ester Compound 15b (230 mg), isolated by flash chromatography as a white solid. MS 307 (MH⁺). Compound 15b (230 mg, 0.752 mmol) was deprotected with 20% TFA in DCM (10 mL) to provide 4-morpholin-4-ylmethyl-benzylamine Compound 15c (63 mg) upon work-up. MS 207 (MH⁺).

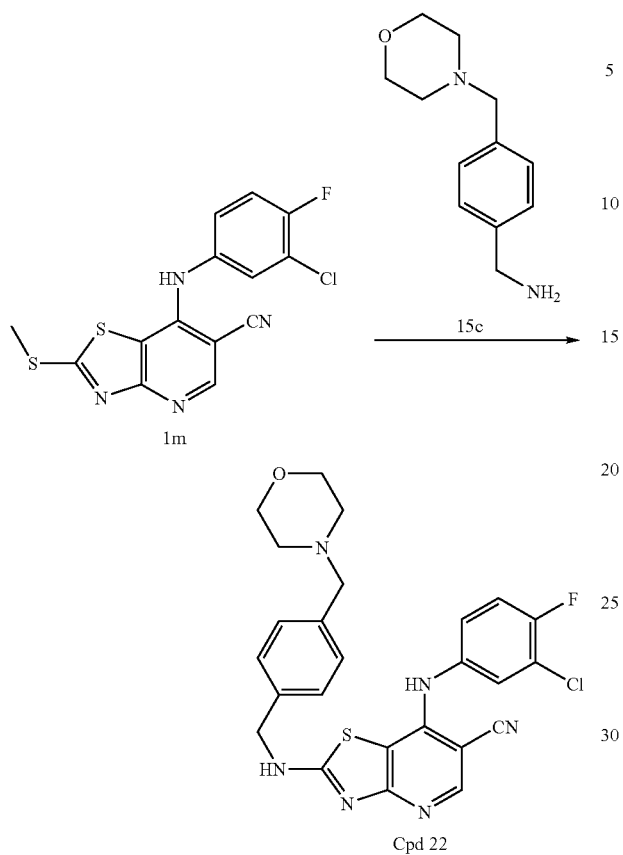

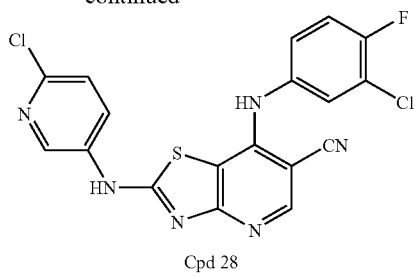

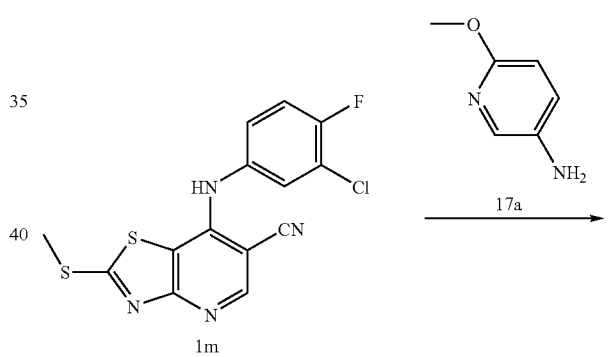

Using the procedure of Example 1, Compound 15c was used in place of Compound 1n and carried forward to prepare Compound 22, which was isolated as a trifluoroacetate salt. MS 509, 511 (MH⁺).

EXAMPLE 16

7-(3-chloro-4-fluoro-phenylamino)-2-(6-chloro-pyridin-3-ylamino)-thiazolo[4,5-b]pyridine-6-carbonitrile (Cpd 28)

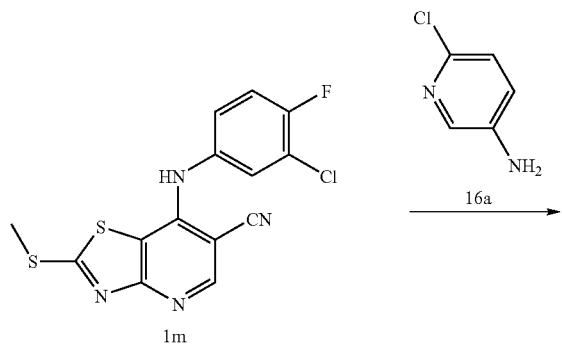

Using the procedure of Example 1, Compound 16a was used in place of Compound 1n and carried forward to prepare Compound 28, which was isolated as an acetic acid salt. $^1$H NMR (DMSO-$d_6$) δ 11.30 (br s, 1H), 9.67 (br s, 1H), 8.69 (d, J=2.9 Hz, 1H), 8.62 (s, 1H), 8.32 (dd, J=8.8, 2.9 Hz, 1H), 7.61-7.49 (m, 3H), 7.33 (ddd, J=8.8, 4.2, 2.8 Hz, 1H). MS 431, 433, 435 (MH⁺).

EXAMPLE 17

7-(3-chloro-4-fluoro-phenylamino)-2-(6-methoxy-pyridin-3-ylamino)-thiazolo[4,5-b]pyridine-6-carbonitrile (Cpd 26)

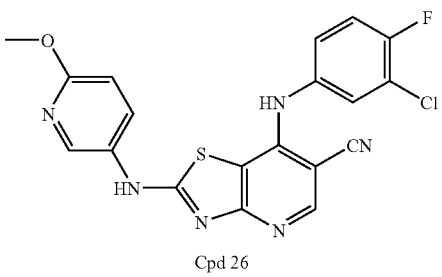

Using the procedure of Example 1, Compound 17a was used in place of Compound 1n and carried forward to prepare Compound 26. $^1$H NMR (DMSO-$d_6$) δ 10.82 (br s, 1H), 9.45 (br s, 1H), 8.52 (s, 1H); 8.44 (d, J=2.5 Hz, 1H), 8.09 (dd, J=9.0, 2.7 Hz, 1H), 7.50 (d, J=9.0, 1H), 7.50-7.45 (m, 1H), 7.26 (ddd, J=9.0, 4.3, 2.7 Hz, 1H); 6.88 (d, J=9.0 Hz, 1H); 3.84 (s, 3H). MS 427, 429 (MH⁺).

EXAMPLE 18

7-(3-chloro-4-fluoro-phenylamino)-2-(6-hydroxy-pyridin-3-ylamino)-thiazolo[4,5-b]pyridine-6-carbonitrile (Cpd 27)

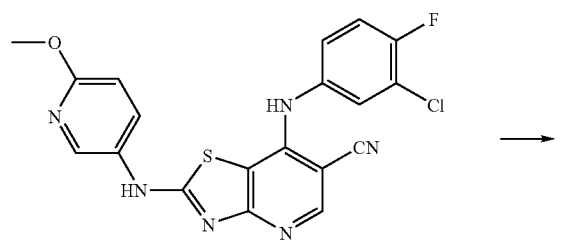

Cpd 26

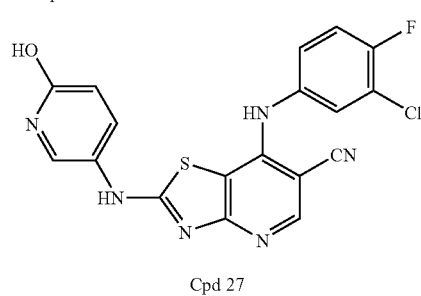

Cpd 27

Compound 26 was heated with aqueous HCl in NMP (3 mL) at 80° C. to prepare Compound 27, which was isolated as a trifluoroacetic acid salt. $^1$H NMR (DMSO-d$_6$) δ 11.52 (br s, 1H), 10.52 (br s, 1H), 9.43 (s, 1H); 8.50 (s, 1H); 8.09 (d, J=2.5 Hz, 1H), 7.52-7.42 (m, 3H), 7.24 (ddd, J=8.7, 4.1, 2.9 Hz, 1H); 6.41 (d, J=9.4 Hz, 1H). MS 413,415 (MH$^+$).

EXAMPLE 19

7-(3-chloro-4-fluoro-phenylamino)-2-[6-(3-morpholin-4-yl-propylamino)-pyridin-3-ylamino]-thiazolo[4,5-b]pyridine-6-carbonitrile (Cpd 29)

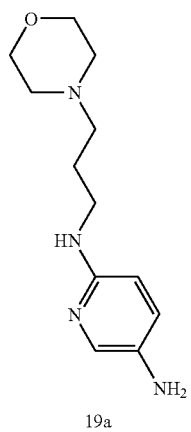

19a 2-chloro-5-nitro-pyridine Compound 16a1 (6.06 g, 38.2 mmol) and 3-morpholin-4-yl-propylamine Compound 9a (6.27 mL, 42.1 mmol) were combined in DMSO (100 mL) and heated to 50° C. After 2.5 hours the reaction mixture was diluted with 0.5 M HCl and washed with ethyl ether. The aqueous layer was adjusted to pH 11 with NaOH and extracted with EtOAc. The combined organic layers were dried over MgSO$_4$ and concentrated to provide (3-morpholin-4-yl-propyl)-(5-nitro-pyridin-2-yl)-amine Compound 19a1. Using the procedure of Example 1, Compound 19a1 was used in place of Compound 1n3 with AcOH (30 mL) replacing EtOAc as solvent. 10% Pd/C (3.1 g) was added to the solution and the reaction was carried forward to provide N$^2$-(3-morpholin-4-yl-propyl)-pyridine-2,5-diamine Compound 19a. $^1$H NMR (CDCl$_3$) δ 7.67 (d, J=3.0 Hz, 1H); 6.95 (dd, J=8.6, 3.0 Hz, 1H); 6.31 (d, J=8.6 Hz, 1H); 3.77-3.66 (m, 4H); 2.52-2.38 (m, 8H); 2.08.(p, J=6.8Hz, 2H). MS 267 (MH$^+$).

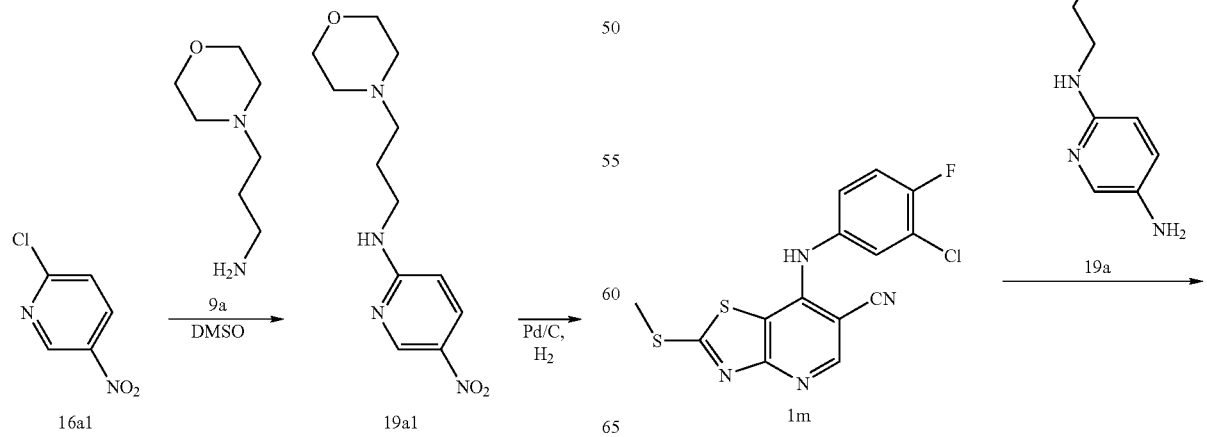

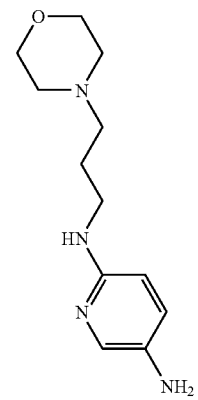

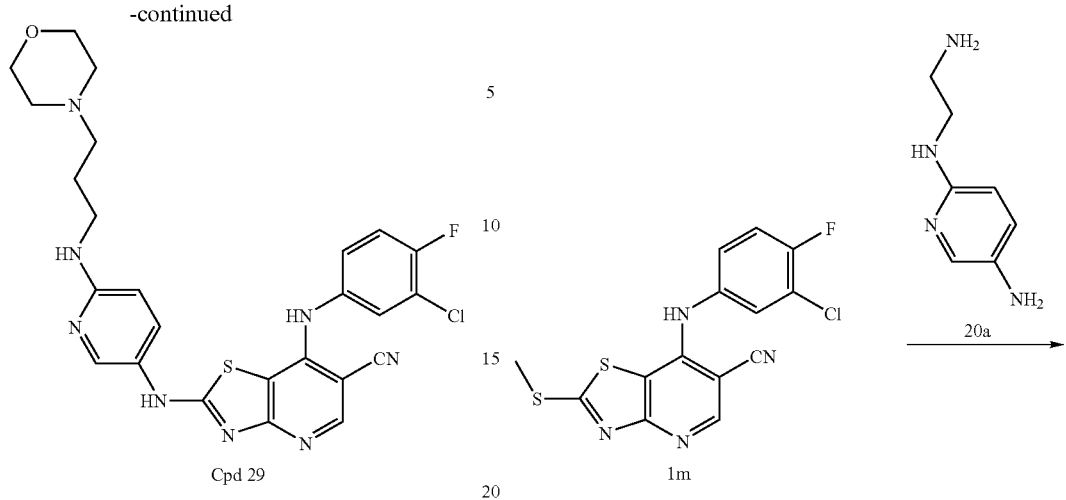

Using the procedure of Example 1, Compound 19a was used in place of Compound 1n and carried forward to prepare Compound 29, which was isolated as a trifluoroacetic acid salt. $^1$H NMR (DMSO-d$_6$) δ 10.80 (br s, 1H), 9.50 (s, 1H), 8.53 (s, 1H), 8.44 (br s, 1H), 7.79 (dd, J=9.0, 2.3 Hz, 1H), 7.53-7.44 (m, 2H), 7.25 (ddd, J=8.8, 4.2, 2.8 Hz, 1H); 6.79 (d, J=9.0 Hz, 1H); 3.89-3.74 (m, 4H); 3.34 (t, J=6.4 Hz, 2H); 3.28-3.13 (m, 6H); 2.00-1.88 (m, 2H). MS 539, 541 (MH$^+$).

EXAMPLE 20

2-[6-(2-amino-ethylamino)-pyridin-3-ylamino]-7-(3-chloro-4-fluoro-phenylamino)-thiazolo[4,5-b]pyridine-6-carbonitrile (Cpd 30)

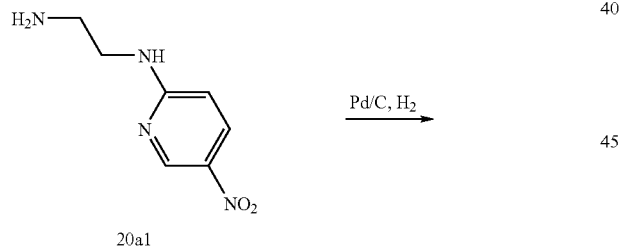

Using the procedure of Example 1, N$^1$-(5-nitro-pyridin-2-yl)-ethane-1,2-diamine Compound 20a1 was used in place of Compound 1n3 and carried forward to prepare N$^2$-(2-amino-ethyl)-pyridine-2,5-diamine Compound 20a.

Using the procedure of Example 1, Compound 20a was used in place of Compound 1n and carried forward to prepare Compound 30, which was isolated as a trifluoroacetic acid salt. $^1$H NMR (DMSO-d$_6$) δ 10.86 (br s, 1H), 9.58 (s, 1H), 8.57 (s, 1H), 8.44 (s, 1H), 7.95-7.80 (m, 3H), 7.54-7.46 (m, 2H), 7.28 (ddd, J=8.7, 4.1, 2.8 Hz, 1H); 6.80 (d, J=8.9Hz, 1H); 3.52 (t, J=5.8 Hz, 2H); 3.04 (q, J=5.8 Hz, 2H). MS 455, 457 (MH$^+$).

EXAMPLE 21

2-[4-(4-amino-piperidin-1-ylmethyl)-phenylamino]-7-(3-chloro-4-fluoro-phenylamino)-thiazolo[4,5-b]pyridine-6-carbonitrile (Cpd 31)

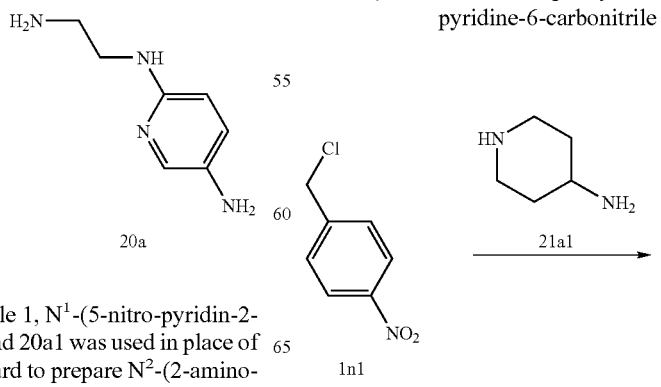

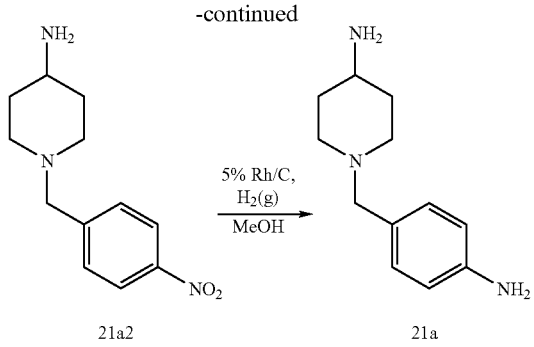

Using the procedure of Example 1, piperidin-4-ylamine Compound 21a1 was used in place of Compound 1n2 and carried forward to prepare 1-(4-nitro-benzyl)-piperidin-4-ylamine Compound 21a2. 5% Rh/C (350 mg) was added to a solution of 1-(4-nitrobenzyl)-piperidin-4-ylamine Compound 21a2 (647 mg, 2.75 mmol) in methanol (15 mL). The mixture was hydrogenated at 50 PSI for a period of 2 hrs, then filtered through Celite. The filtrate was evaporated in vacuo to give 1-(4-amino-benzyl)-piperidin-4-ylamine Compound 21a (640 mg) as a light yellow oil. $^1$H NMR (CDCl$_3$) δ 7.09 (d, J=8.2 Hz, 2H); 6.64 (d, J=8.2 Hz, 2H); 3.62 (br s, 1H); 3.41 (s, 2H); 2.88-2.80 (m, 2H); 2.70-2.58 (m, 1H); 2.07-1.95 (m, 2H); 1.84-1.74 (m, 2H); 1.57 (br s, 2H); 1.47-1.32 (m, 2H); 1.31-1.18 (m, 2H).

Using the procedure of Example 1, Compound 21a was used in place of Compound 1n and carried forward to prepare Compound 31, which was isolated as a trifluoroacetic acid salt. $^1$H NMR (DMSO-d$_6$) δ 11.07(br s, 1H), 9.88 (br s, 1H), 9.56 (s, 1H), 8.57 (s, 1H), 8.20-8.07 (m, 3H), 7.82 (d, J=8.3 Hz, 2H); 7.55-7.45 (m, 4H), 7.29 (ddd, J=8.8, 4.3, 2.7 Hz, 1H); 4.29 (s, 2H); 3.44 (d, J=11.2 Hz, 2H); 3.34-3.16 (m, 1H); 3.08-2.93 (m, 2H); 2.15-1.99 (m, 2H); 1.81-1.65 (m, 2H). MS 508, 510 (MH$^+$).

EXAMPLE 22

7-(3-ethynyl-phenylamino)-2-(3-morpholin-4-yl-propylamino)-thiazolo[4,5-b]pyridine-6-carbonitrile (Cpd 9)

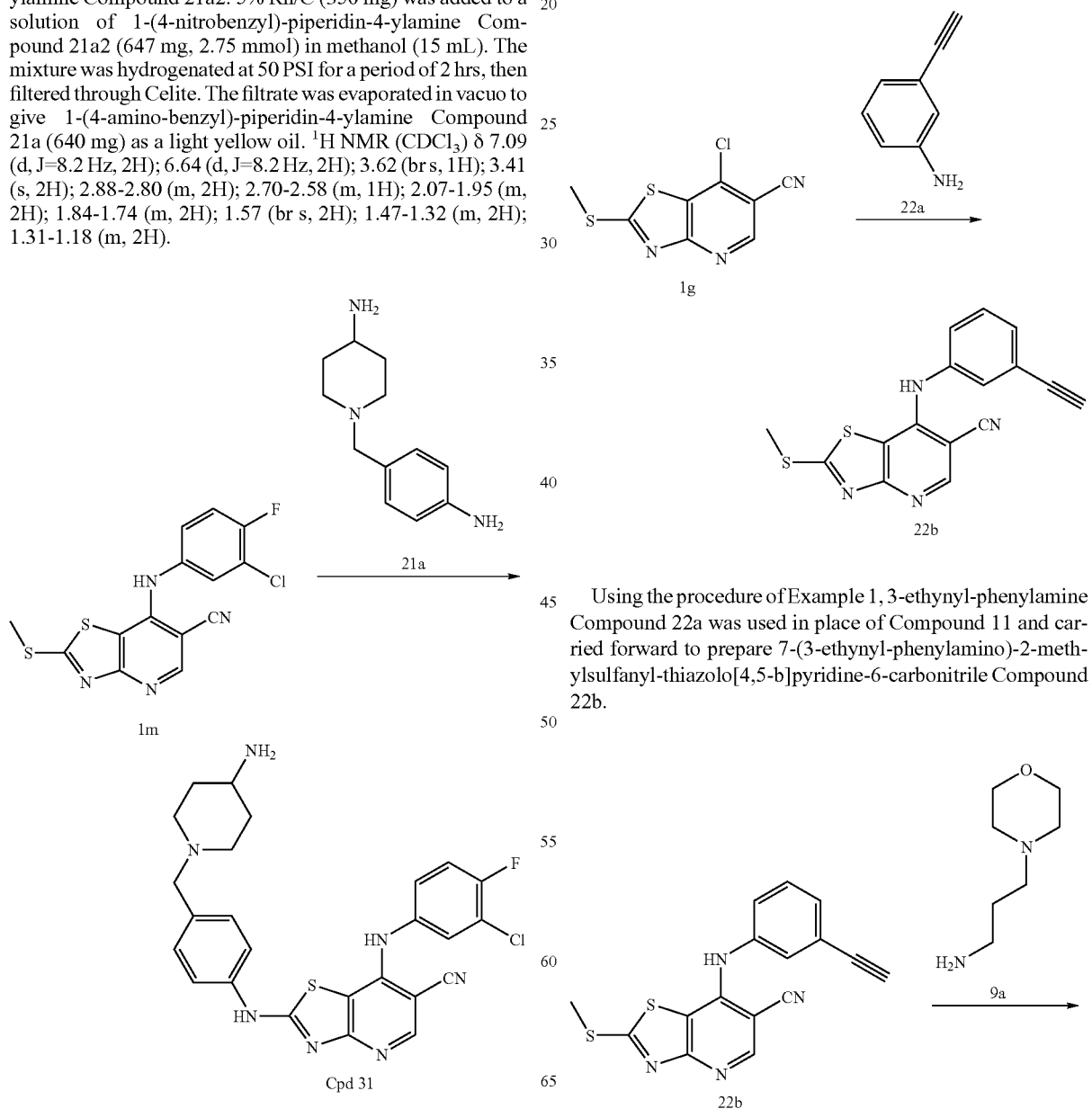

Using the procedure of Example 1, 3-ethynyl-phenylamine Compound 22a was used in place of Compound 1l and carried forward to prepare 7-(3-ethynyl-phenylamino)-2-methylsulfanyl-thiazolo[4,5-b]pyridine-6-carbonitrile Compound 22b.

-continued

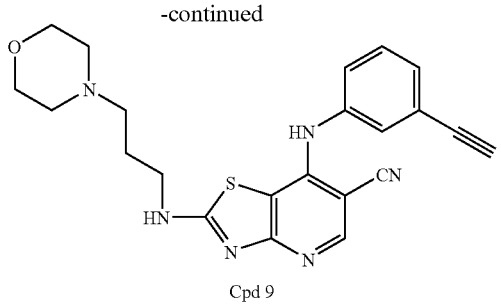
Cpd 9

Using the procedure of Example 1, Compound 22b, used in place of Compound 1m, and Compound 9a, used in place of Compound 1n, were carried forward to prepare Compound 9, which was isolated as a trifluoroacetate salt. $^1$H NMR (DMSO-d$_6$) δ 9.67 (br s, 1H), 9.47 (s, 1H), 8.82 (br s, 1H), 8.52 (s, 1H), 7.52-7.32 (m, 2H), 7.26-7.17 (m, 2H), 4.27 (s, 1H), 3.78-3.58 (m, 4H), 3.54-3.38 (m, 4H), 3.22-3.00 (m, 4H), 2.04-1.90 (m, 2H). MS 419 (MH$^+$).

EXAMPLE 23

2-(4-dimethylaminomethyl-phenylamino)-7-(3-ethynyl-phenylamino)thiazolo[4,5-b]pyridine-6-carbonitrile (Cpd 10)

Using the procedure of Example 1, Compound 22b, used in place of Compound 1m, and Compound 4a, used in place of Compound 1n, were carried forward to prepare Compound 10, which was isolated as a trifluoroacetate salt. $^1$H NMR (DMSO-d$_6$) δ 11.06 (s, 1H), 9.67 (br s, 1H), 9.57 (s, 1H), 8.59 (s, 1H), 7.82 (d, J=8.2 Hz, 2H), 7.50 (d, J=8.2 Hz, 2H), 7.46 (t, J=7.7 Hz, 1H), 7.39 (d, J=7.7 Hz, 1H), 7.30 (s, 1 H), 7.27 (d, J=7.7 Hz, 1H), 4.28 (s, 1H), 4.25 (s, 2H), 2.73 (s, 6H). MS 425 (MH$^+$).

EXAMPLE 24

7-(3-ethynyl-phenylamino)-2-{4-[(2S)2-hydroxymethyl-pyrrolidin-1-ylmethyl]-phenylamino}-thiazolo[4,5-b]pyridine-6-carbonitrile (Cpd 11)

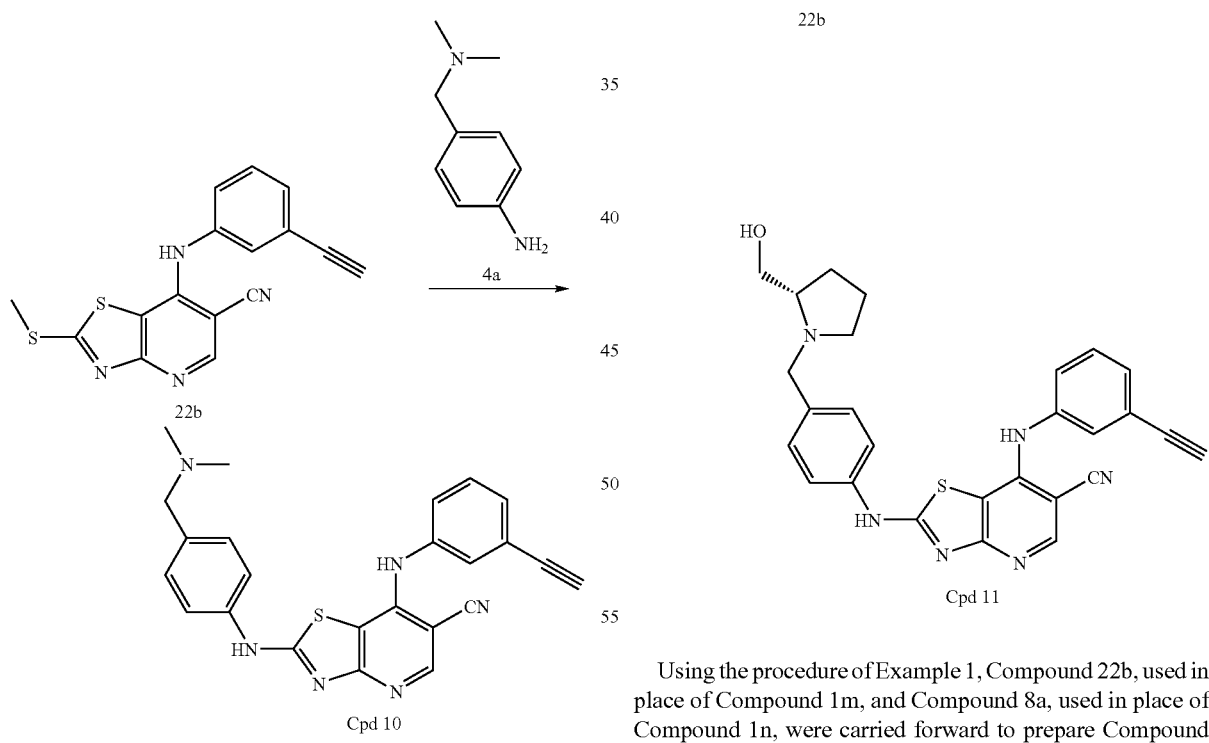
Cpd 11

Using the procedure of Example 1, Compound 22b, used in place of Compound 1m, and Compound 8a, used in place of Compound 1n, were carried forward to prepare Compound 11, which was isolated as a trifluoroacetate salt. $^1$H NMR (DMSO-d$_6$) δ 11.06 (s, 1H), 9,59 (s, 1H), 9.43 (br s, 1H), 8.59 (s, 1H), 7.80 (d, J=7.9 Hz, 2H), 7.54 (d, J=7.9 Hz, 2H), 7.45 (t, J=7.7 Hz, 1H), 7.38 (dd, J=7.7, 1.2 Hz, 1H), 7.29 (s, 1H), 7.26 (d, J=7.7 Hz, 1H), 4.53-4.21 (m, 7H), 3.33-3.23 (m, 1H), 3.22-3.12 (m, 1H), 2.17-2.05 (m, 1H), 2.02-1.91 (m, 1H), 1.88-1.69 (m, 2H). MS 481 (MH$^+$).

EXAMPLE 25

7-(3-ethynyl-phenylamino)-2-(2-morpholin-4-yl-ethylamino)-thiazolo[4,5-b]pyridine-6-carbonitrile (Cpd 13)

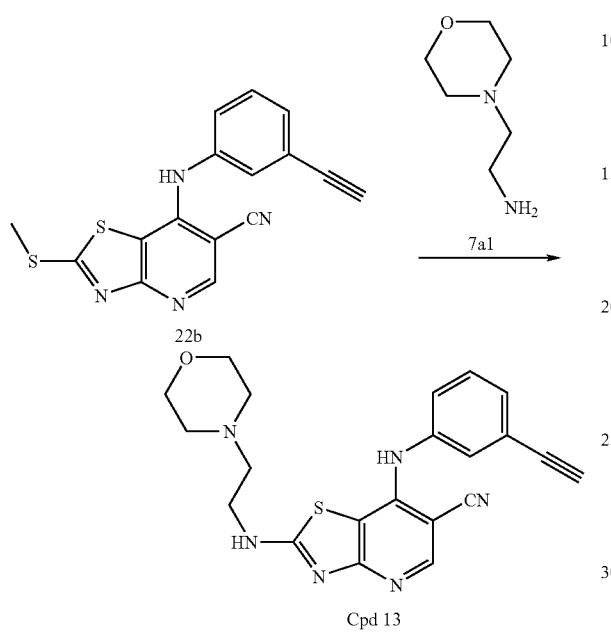

Using the procedure of Example 1, Compound 22b, used in place of Compound 1m, and Compound 7a1, used in place of Compound 1n, were carried forward to prepare Compound 13, which was isolated as a trifluoroacetate salt. $^1$H NMR (DMSO-d$_6$) δ 9.78 (br s, 1H), 9.45 (s, 1H), 8.86 (t, J=4.9 Hz, 1H), 8.53 (s, 1H), 7.43 (t, J=8.0 Hz, 1H), 7.36 (d, J=8.0 Hz, 1H), 7.22 (s, 1H), 7.21 (d, J=8.0 Hz, 1H), 4.28 (s, 1H), 4.06-3.93 (m, 2H), 3.83-3.74 (m, 2H), 3.73-3.49 (m, 4H), 3.40-3.31 (m, 2H), 3.22-3.06 (m, 2H). MS 405 (MH$^+$).

EXAMPLE 26

4-[6-cyano-7-(3-ethynyl-phenylamino)-thiazolo[4,5-b]pyridin-2-ylamino]-N-(3-dimethylamino-propyl)-benzenesulfonamide (Cpd 23)

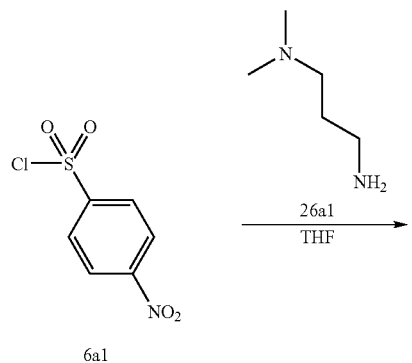

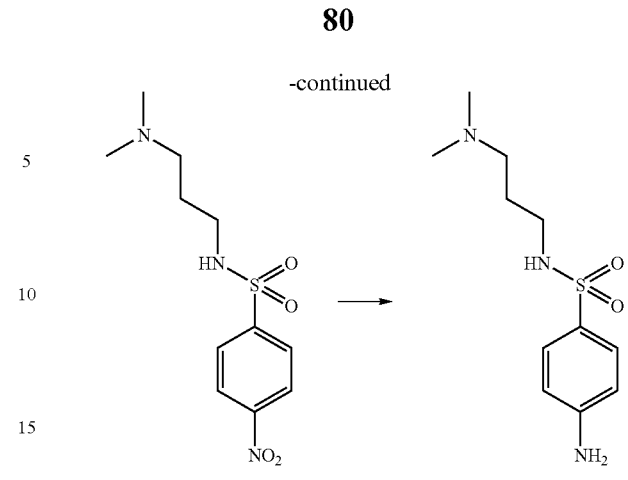

Using the procedure of Example 1, 4-nitro-benzenesulfonyl chloride Compound 6a1, used in place of Compound 1n1, and N$^1$,N$^1$-dimethyl-propane-1,3-diamine Compound 26a1, used in place of Compound 1n2, were carried forward to prepare 4-amino-N-(3-dimethylamino-propyl)-benzenesulfonamide Compound 26a.

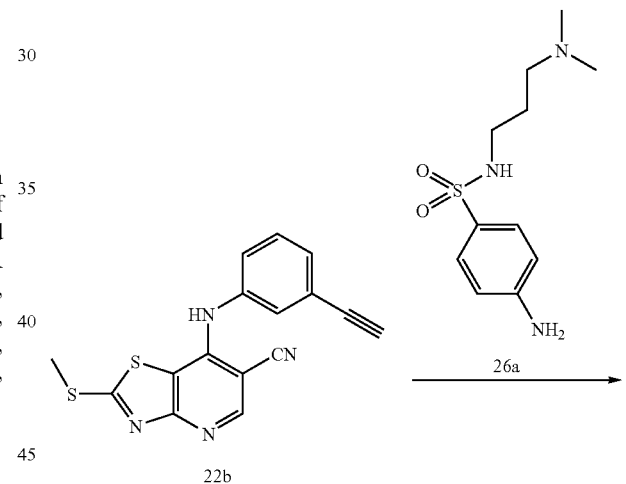

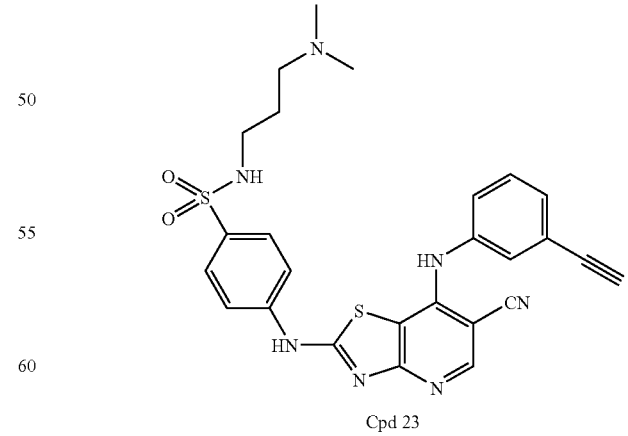

Using the procedure of Example 1, Compound 22b, used in place of Compound 1m, and Compound 26a, used in place of Compound 1n, were carried forward to prepare Compound 23, which was isolated as a trifluoroacetate salt. $^{1}$H NMR (DMSO-d$_{6}$) δ 11.28 (s, 1H), 9.61 (s, 1H), 9.37 (br s, 1H), 8.63 (s, 1H), 7.97 (d, J=8.9 Hz, 2 H), 7.84 (d, J=8.9 Hz, 2H), 7.69 (t, J=6.1 Hz, 1H), 7.53-7.40 (m, 2H), 7.36-7.28 (m, 2H), 4.30 (s, 1H), 3.14-3.03 (m, 2H), 2.89-2.75 (m, 8H), 1.85-1.73 (m, 2H). MS 532 (MH$^{+}$).

EXAMPLE 27

7-(3-chloro-phenylamino)-2-(2-morpholin-4-yl-ethylamino)-thiazolo[4,5-b]pyridine-6-carbonitrile (Cpd 12)

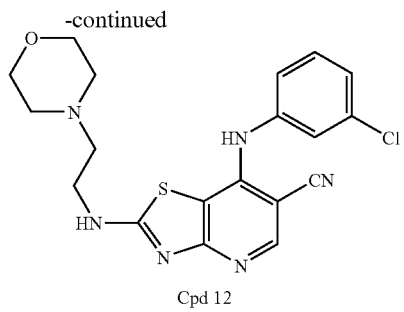

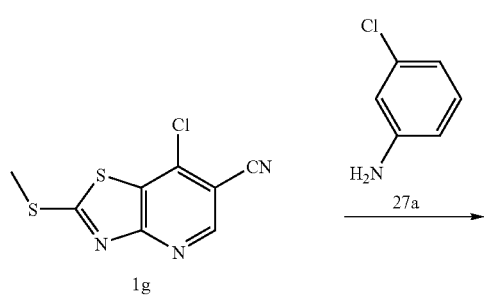

Using the procedure of Example 1, 3-chloroaniline Compound 27a was used in place of Compound 11 and carried forward to prepare 7-(3-chloro-phenylamino)-2-methylsulfanyl-thiazolo[4,5-b]pyridine-6-carbonitrile Compound 27b.

Using the procedure of Example 1, Compound 27b, used in place of Compound 1m, and Compound 7a1, used in place of Compound 1n, were carried forward to prepare Compound 12, which was isolated as a trifluoroacetate salt. $^{1}$H NMR (DMSO-d$_{6}$) δ 9.91 (br s, 1H), 9.54 (s, 1H), 8.91 (br s, 1H), 8.54 (s, 1H), 7.43 (t, J=7.8 Hz, 1 H), 7.29 (d, J=7.8 Hz, 1H), 7.20 (t, J=1.8 Hz, 1H), 7.11 (d, J=7.8 Hz, 1H), 4.08-3.90 (m, 2H), 3.84-3.74 (m, 2H), 3.71-3.33 (m, 6H), 3.23-3.05 (m, 2H). MS 415, 417 (MH$^{+}$).

EXAMPLE 28

7-(3-chloro-phenylamino)-2-(4-morpholin-4-ylmethyl-phenylamino)-thiazolo[4,5-b]pyridine-6-carbonitrile (Cpd 19)

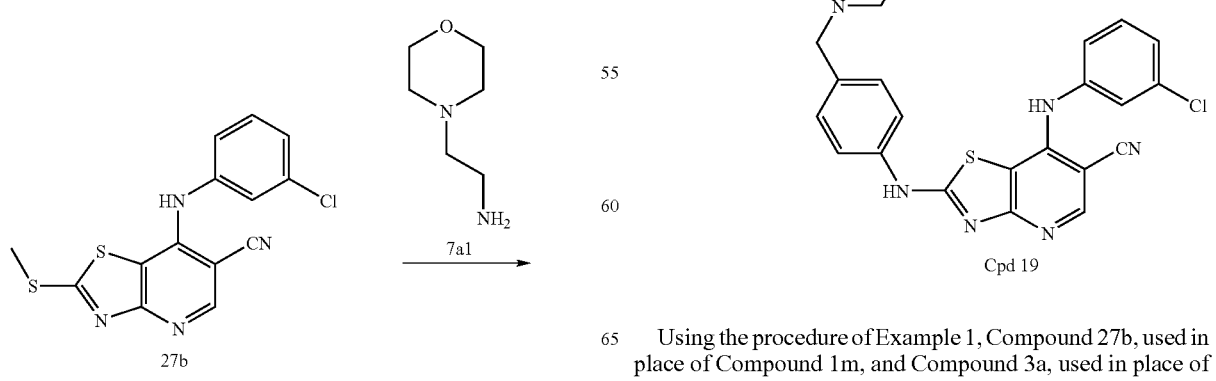

Using the procedure of Example 1, Compound 27b, used in place of Compound 1m, and Compound 3a, used in place of Compound 1n, were carried forward to prepare Compound 19, which was isolated as a trifluoroacetate salt. $^1$H NMR (DMSO-d$_6$) δ 11.11 (s, 1H), 10.03 (br s, 1H), 9.65 (s, 1H), 8.61 (s, 1H), 7.83 (d, J=7.6 Hz, 2H), 7.52 (d, J=7.6 Hz, 2H), 7.45 (t, J=8.0 Hz, 1H), 7.32 (d, J=8.0 Hz, 1H), 7.28 (s, 1 H), 7.18 (d, J=8.0 Hz, 1H), 4.33 (s, 2H), 4.04-3.92 (m, 2H), 3.73-3.57 (m, 2H), 3.33-3.22 (m, 2H), 3.18-3.04 (m, 2H). MS 477, 479 (MH$^+$).

EXAMPLE 29

7-(2,2-difluoro-benzo[1,3]dioxol-4-ylamino)-2-(4-dimethylaminomethyl-phenylamino)-thiazolo[4,5-b]pyridine-6-carbonitrile (Cpd 25)

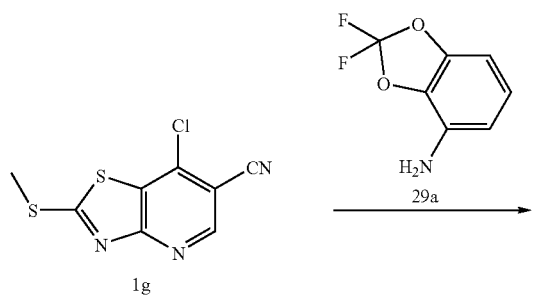

Using the procedure of Example 1, 2,2-difluoro-benzo[1,3]dioxol-4-ylamine Compound 29a was used in place of Compound 1l and carried forward to prepare 7-(2,2-difluoro-benzo[1,3]dioxol-4-ylamino)-2-methylsulfanyl-thiazolo[4,5-b]pyridine-6-carbonitrile Compound 29b.

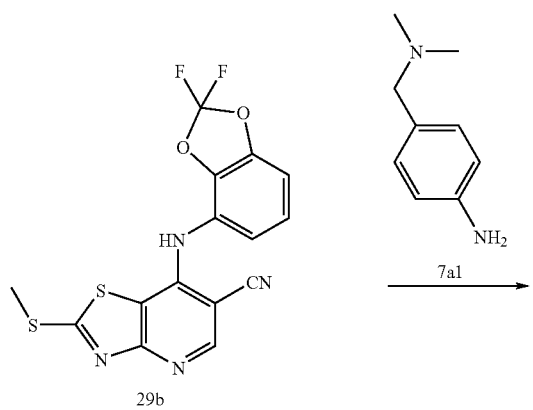

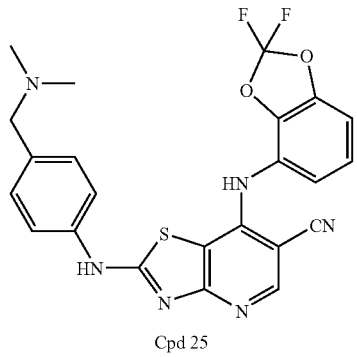

Using the procedure of Example 1, Compound 29b, used in place of Compound 1m, and Compound 7a1, used in place of Compound 1n, were carried forward to prepare Compound 25, which was isolated as a hydrochloride salt. $^1$H NMR (DMSO-d$_6$) δ 11.42 (br s, 1H), 10.46 (br s, 1H), 9.97 (br s, 1H), 8.66 (s, 1H), 7.84 (d, J=8.4 Hz, 2H), 7.58 (d, J=8.4 Hz, 2H), 7.43 (d, J=8.2 Hz, 1H), 7.32 (t, J=8.2 Hz, 1H), 7.21 (d, J=8.2 Hz, 1H), 4.25 (s, 2H), 2.70 (s, 6H). MS 481 (MH$^+$).

EXAMPLE 30

7-[3-chloro-4-(3-fluoro-benzyloxy)-phenylamino]-2-(4-pyrrolidin-1-ylmethyl-phenylamino)-thiazolo[4,5-b]pyridine-6-carbonitrile (Cpd 24)

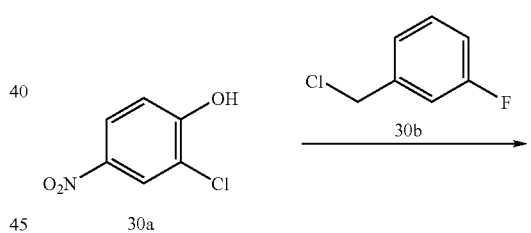

1-Fluoro-3-(4-nitro-2-chloro-phenoxymethyl)-phenyl Compound 30c was prepared according to the procedure described in Cockerill G S, Carter M C, Guntrip S B and Smith K J, Preparation of azolylquinazolines and related compounds as protein tyrosine kinase inhibitors, PCT Application WO98/02434.

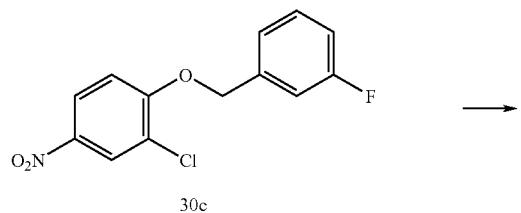

30c

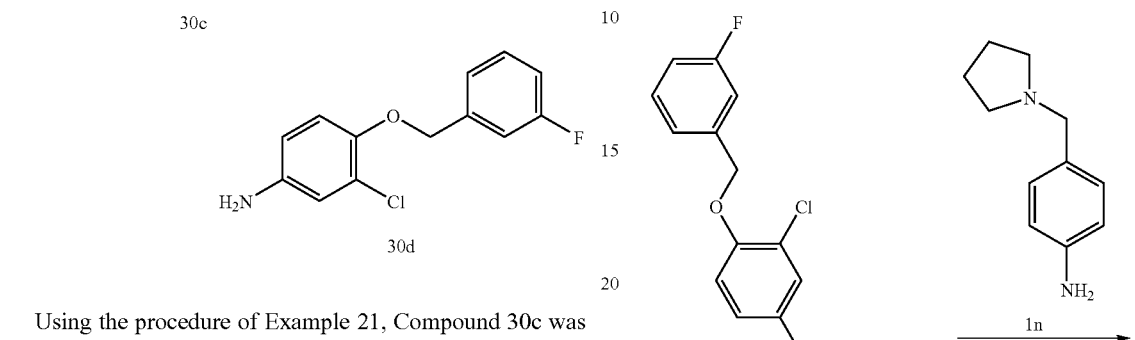

Using the procedure of Example 21, Compound 30c was used in place of Compound 21a2 and carried forward to prepare 3-chloro-4-(3-fluoro-benzyloxy)-phenylamine Compound 30d.

Using the procedure of Example 1, Compound 30d was used in place of Compound 11 and carried forward to prepare 7-[3-chloro-4-(3-fluoro-benzyloxy)-phenylamino]-2-methylsulfanyl-thiazolo[4,5-b]pyridine-6-carbonitrile Compound 30e.

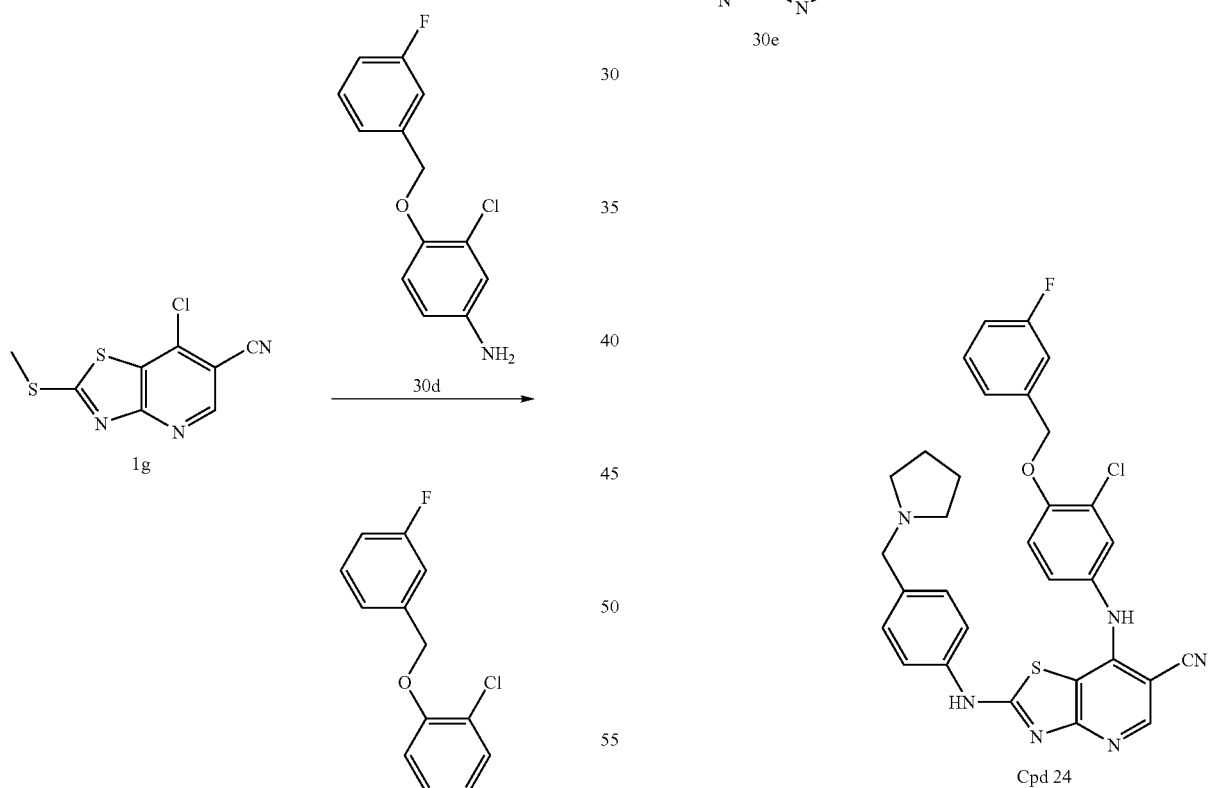

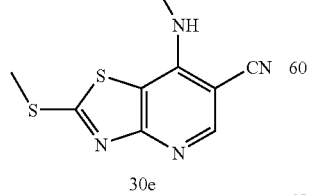

Using the procedure of Example 1, Compound 30e was used in place of Compound 1m and carried forward to prepare Compound 24, which was isolated as a trifluoroacetate salt. $^1$H NMR (DMSO-$d_6$) δ11.0 (s, 1H), 9.80 (br s, 1H), 9.38 (s, 1H), 8.54 (s, 1H), 7.82 (d, J=8.6 Hz, 2H), 7.56-7.48 (m, 3H), 7.46 (d, J=2.2 Hz, 1H), 7.41-7.19 (m, 5H), 5.31 (s, 2H), 4.33 (s, 2H), 3.46-3.31 (m, 2H), 3.18-3.03 (m, 2H), 2.12-1.78 (m, 4H). MS 585, 587 (MH$^+$).

EXAMPLE 31

7-(5-chloro-benzo[1,3]dioxol-4-ylamino)-2-(4-morpholin-4-ylmethyl-phenylamino)-thiazolo[4,5-b]pyridine-6-carbonitrile (Cpd 20)

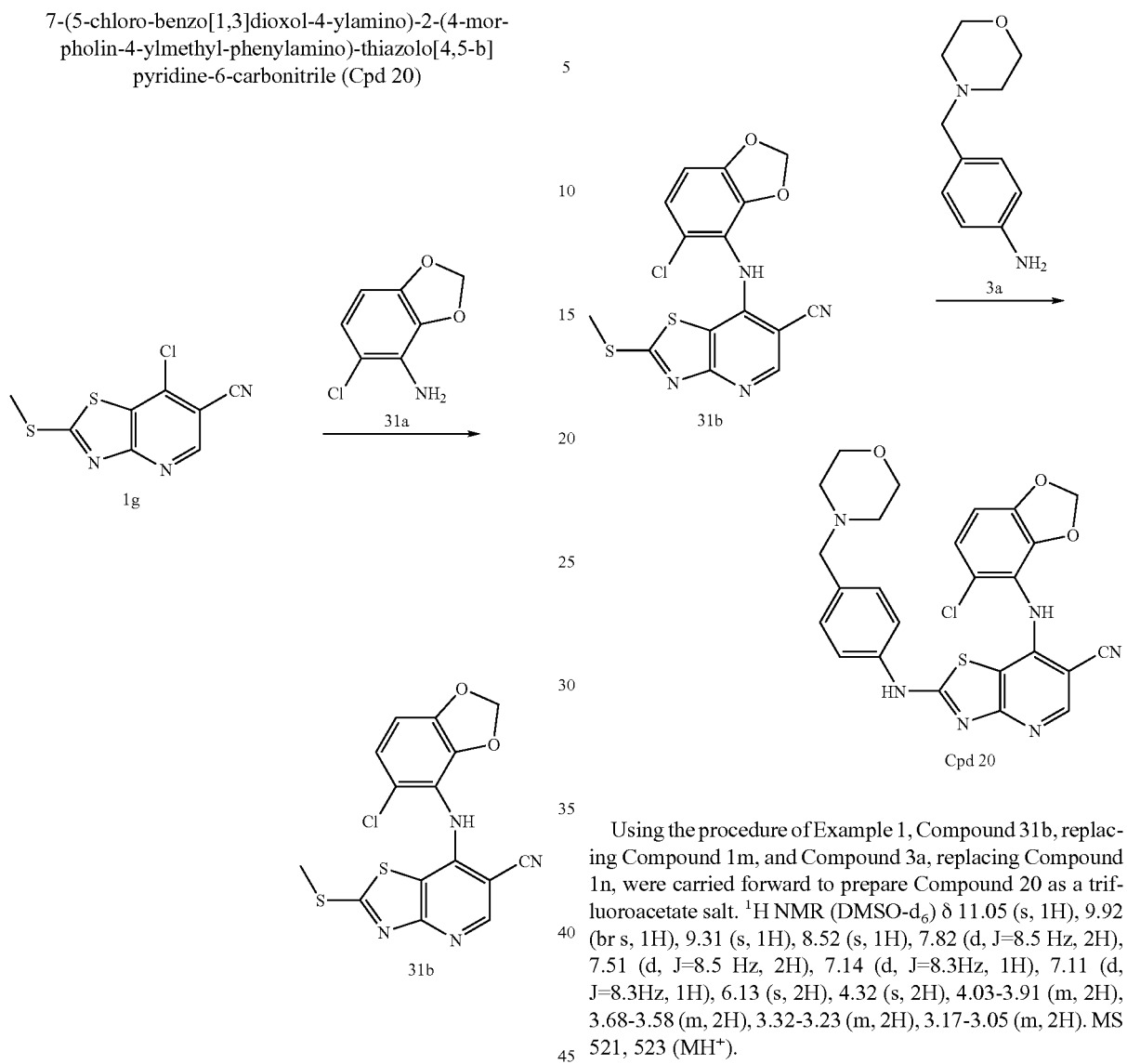

1M sodium hexamethyldisilazane in THF (1.42 mL, 1.42 mmol) was added to 5-chloro-benzo[1,3]dioxol-4-ylamine Compound 31a (as described in PCT Application WO03/008409) (221 mg, 1.29 mmol) in DMF at 0° C. and the mixture was stirred for 15 min. 7-chloro-2-methylsulfanyl-thiazolo[4,5-b]pyridine-6-carbonitrile Compound 1g (312 mg, 1.29 mmol) in DMF (1 mL) was added and the reaction mixture stirred for an additional 2 hr at ambient temperature. The mixture was then diluted with water and filtered through Celite 545 to form a plug. The celite plug was rinsed with EtOAc and the organic layer was isolated and washed with brine. The organic layer was dried over MgSO$_4$, then filtered and evaporated onto silica gel. Isolation by flash chromatography (eluted with a 20 to 40% EtOAc/hexane gradient) gave 7-(5-chloro-benzo[1,3]dioxol-4-ylamino)-2-methylsulfanyl-thiazolo[4,5-b]pyridine-6-carbonitrile Compound 31b (30 mg) as a yellow oil. MS 377, 379 (MH+).

Using the procedure of Example 1, Compound 31b, replacing Compound 1m, and Compound 3a, replacing Compound 1n, were carried forward to prepare Compound 20 as a trifluoroacetate salt. $^1$H NMR (DMSO-d$_6$) δ 11.05 (s, 1H), 9.92 (br s, 1H), 9.31 (s, 1H), 8.52 (s, 1H), 7.82 (d, J=8.5 Hz, 2H), 7.51 (d, J=8.5 Hz, 2H), 7.14 (d, J=8.3Hz, 1H), 7.11 (d, J=8.3Hz, 1H), 6.13 (s, 2H), 4.32 (s, 2H), 4.03-3.91 (m, 2H), 3.68-3.58 (m, 2H), 3.32-3.23 (m, 2H), 3.17-3.05 (m, 2H). MS 521, 523 (MH$^+$).

EXAMPLE 32

7-(6-bromo-benzo[1,3]dioxol-4-ylamino)-2-(4-morpholin-4-ylmethyl-phenylamino)-thiazolo[4,5-b]pyridine-6-carbonitrile (Cpd 32)

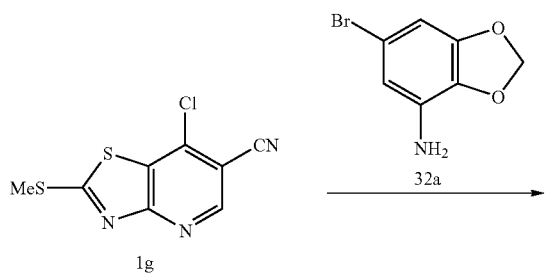

-continued

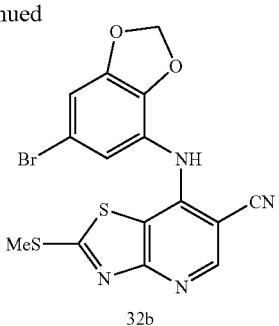

32b

Using the procedure of Example 31, 6-bromo-benzo[1,3]dioxol-4-ylamine Compound 32a (prepared as described in PCT Application WO03/008409) was used in place of Compound 31a and carried forward to prepare 7-(6-bromo-benzo[1,3]dioxol-4-ylamino)-2-methylsulfanyl-thiazolo[4,5-b]pyridine-6-carbonitrile Compound 32b.

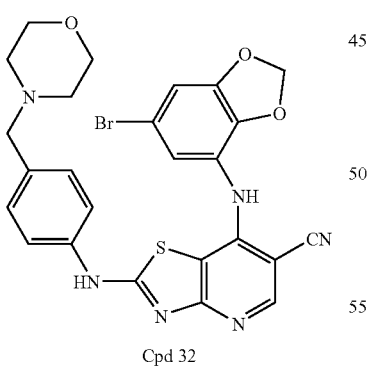

32b

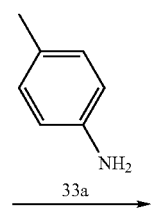

3a

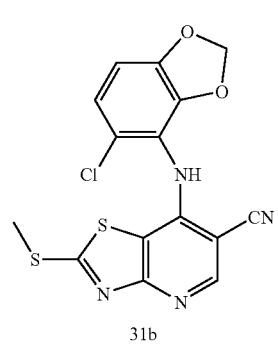

Cpd 32

Using the procedure of Example 1, Compound 32b, replacing Compound 1m, and Compound 3a, replacing Compound 1n, were carried forward to prepare Compound 32 as a trifluoroacetate salt. $^1$H NMR (DMSO-$d_6$) δ 11.08 (s, 1H), 9.84 (br s, 1H), 9.49 (s, 1H), 8.55 (s, 1H), 7.84 (d, 2H), 7.50 (d, 2H), 7.23 (d, 1H), 7.04 (d, 1H), 6.04 (s, 2H), 4.32 (s, 2H), 4.04-3.91 (m, 2H), 3.71-3.55 (m, 2H), 3.36-3.01 (m, 4H). MS 565, 567 (MH$^+$).

EXAMPLE 33

7-(5-chloro-benzo[1,3]dioxol-4-ylamino)-2-p-tolylamino-thiazolo[4,5-b]pyridine-6-carbonitrile (Cpd 33)

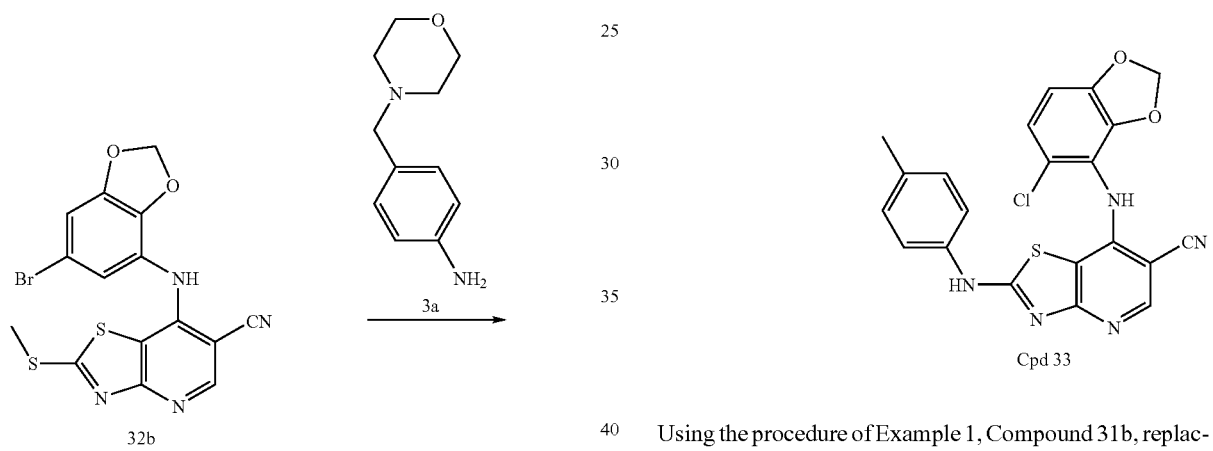

Using the procedure of Example 1, Compound 31b, replacing Compound 1m, and p-tolylamine Compound 33a, replacing Compound 1n, were carried forward to prepare Compound 33 as a trifluoroacetate salt. $^1$H NMR (DMSO-$d_6$) δ 10.75 (s, 1H), 9.18 (s, 1H), 8.44 (s, 1H), 7.59 (d, 2H), 7.17 (d, 2H), 7.11 (d, 1H), 7.08 (d, 1H), 6.11 (s, 2H), 2.29 (s, 3H). MS 436, 438 (MH$^+$).

EXAMPLE 34

7-(2,4-dichloro-phenylamino)-2-(4-morpholin-4-ylmethyl-phenylamino)-thiazolo[4,5-b]pyridine-6-carbonitrile (Cpd 34)

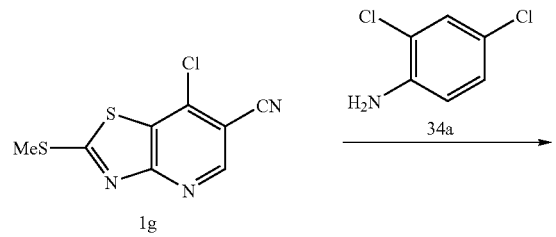

1g

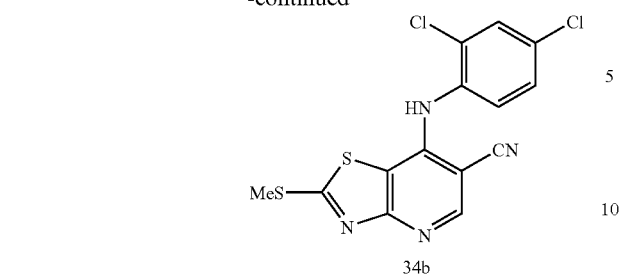

Using the procedure of Example 31, 2,4-dichloroaniline Compound 34a was used in place of Compound 31a and carried forward to prepare 7-(2,4-dichlorophenylamino)-2-methylsulfanyl-thiazolo[4,5-b]pyridine-6-carbonitrile Compound 34b.

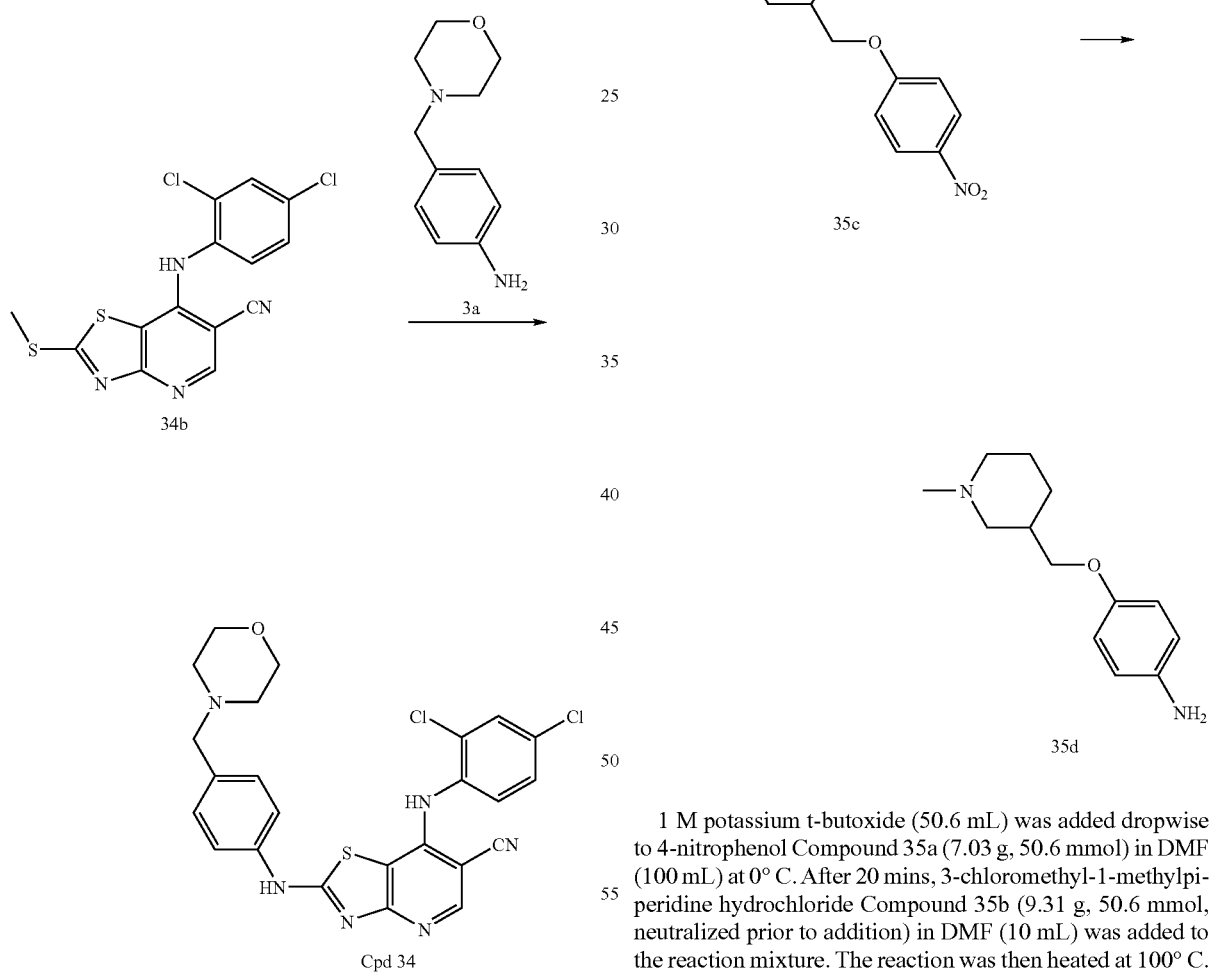

Using the procedure of Example 1, Compound 34b, replacing Compound 1m, and Compound 3a, replacing Compound 1n, were carried forward to prepare Compound 34 as a trifluoroacetate salt. $^1$H NMR (DMSO-d$_6$) δ 9.94 (br s, 1H), 9.48 (s, 1H), 8.53 (s, 1H), 7.84 (s, 1H), 7.81 (d, J=8.0 Hz, 2H), 7.57-7.53 (m, 2H), 7.50 (d, J=8.0 Hz, 1H), 4.08-3.91 (m, 2H), 3.70-3.54 (m, 2H), 3.32-3.01 (m, 4H). MS 511,513(MH$^+$).

EXAMPLE 35

7-(2-chloro-5-methoxy-phenylamino)-2-[4-(1-methyl-piperidin-3-ylmethoxy)-phenylamino]-thiazolo[4,5-b]pyridine-6-carbonitrile (Cpd 35)

1 M potassium t-butoxide (50.6 mL) was added dropwise to 4-nitrophenol Compound 35a (7.03 g, 50.6 mmol) in DMF (100 mL) at 0° C. After 20 mins, 3-chloromethyl-1-methylpiperidine hydrochloride Compound 35b (9.31 g, 50.6 mmol, neutralized prior to addition) in DMF (10 mL) was added to the reaction mixture. The reaction was then heated at 100° C. for 5 days. The cooled reaction was diluted with 1 N NaOH and washed with ethyl ether. The aqueous layer was then adjusted to pH 5 with NaH$_2$PO$_4$ and extracted with ethyl acetate. After drying over MgSO$_4$, the organic layer was evaporated down to give 6.0 g of 1-methyl-3-(4-nitro-phenoxymethyl)-piperidine Compound 35c. Using the procedure of Example 1, Compound 35c was used in place of Compound 1n3 and carried forward to prepare 4-(1-methyl-piperidin-3-ylmethoxy)-phenylamine Compound 35d.

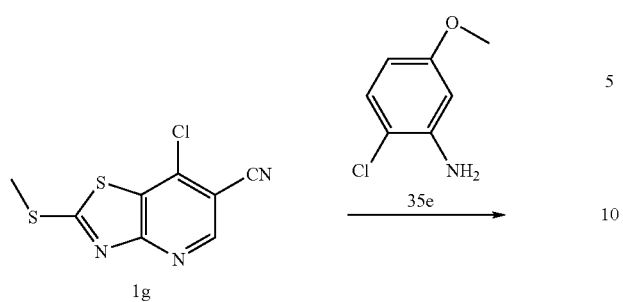

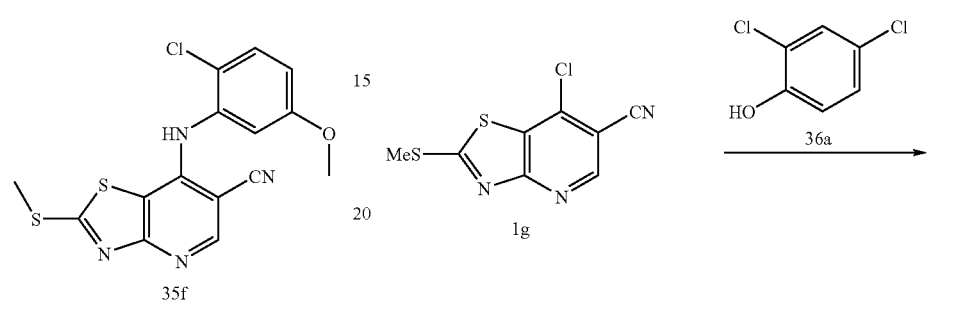

Using the procedure of Example 31, 2-chloro-5-methoxyaniline Compound 35e was used in place of Compound 31a and carried forward to prepare 7-(2-chloro-5-methoxy-phenylamino)-2-methylsulfanyl-thiazolo[4,5-b]pyridine-6-carbonitrile Compound 35f.

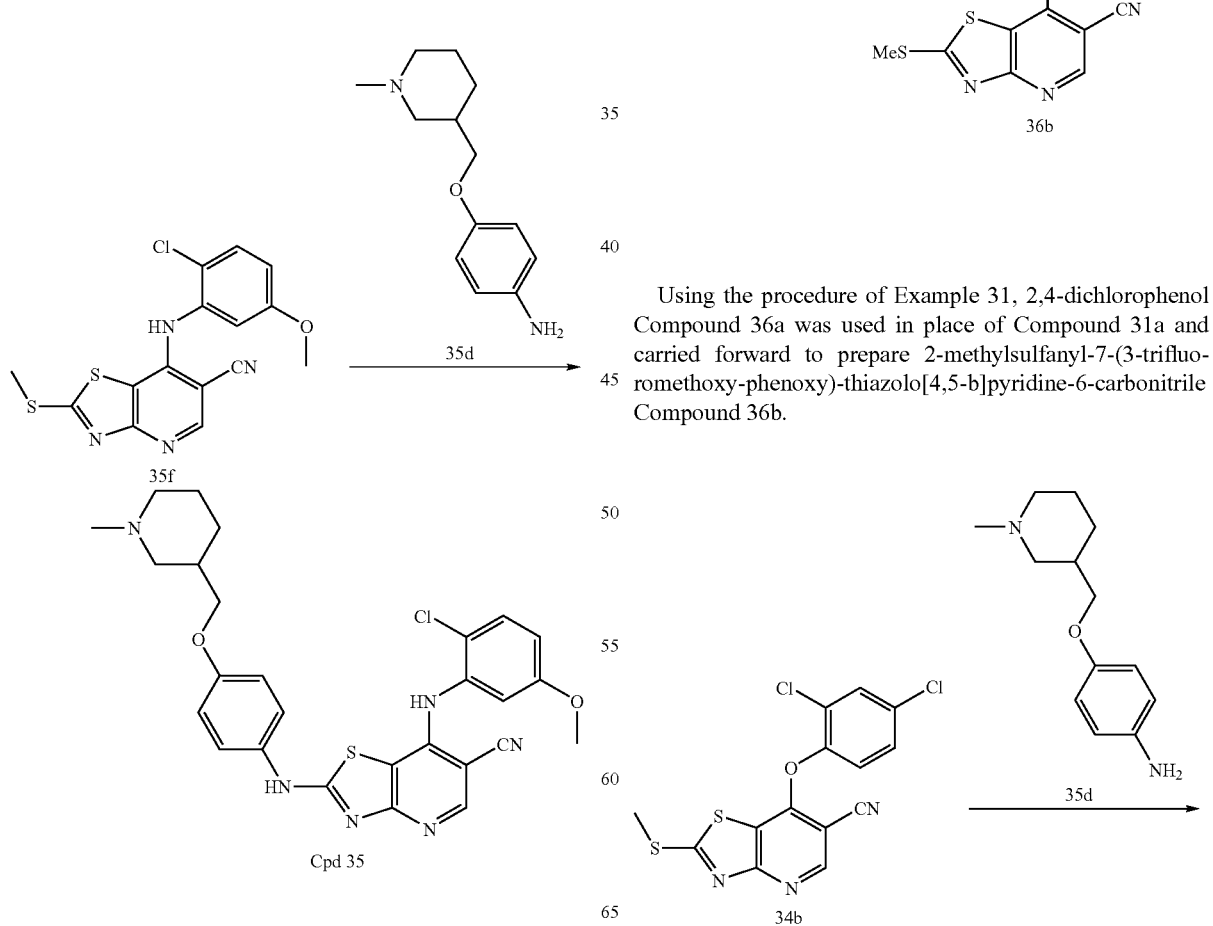

Using the procedure of Example 1, Compound 35f, replacing Compound 1m, and Compound 35d, replacing Compound 1n, were carried forward to prepare Compound 35 as a trifluoroacetate salt. MS 535, 537 (MH$^+$).

EXAMPLE 36

7-(2,4-dichloro-phenoxy)-2-[4-(1-methyl-piperidin-3-ylmethoxy)-phenylamino]-thiazolo[4,5-b]pyridine-6-carbonitrile (Cpd 36)

Using the procedure of Example 31, 2,4-dichlorophenol Compound 36a was used in place of Compound 31a and carried forward to prepare 2-methylsulfanyl-7-(3-trifluoromethoxy-phenoxy)-thiazolo[4,5-b]pyridine-6-carbonitrile Compound 36b.

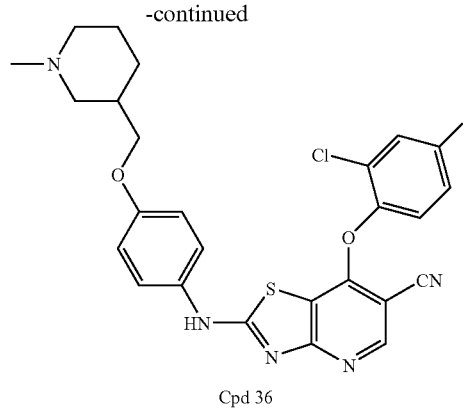

Cpd 36

Using the procedure of Example 1, Compound 34b, replacing Compound 1m, and Compound 35d, replacing Compound 1n, were carried forward to prepare Compound 36 as a trifluoroacetate salt. MS 540, 542, 544 (MH+).

EXAMPLE 37

2-[4-(1-methyl-piperidin-3-ylmethoxy)-phenylamino]-7-(3-trifluoromethoxy-phenoxy)-thiazolo[4,5-b]pyridine-6-carbonitrile (Cpd 37)

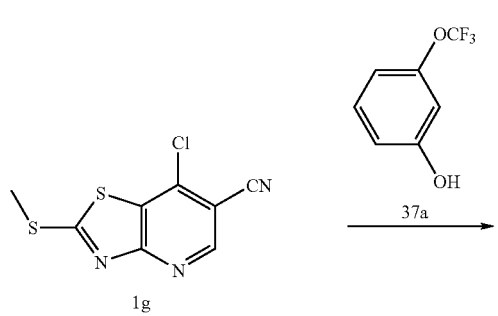

Using the procedure of Example 31, 3-trifluoromethoxyphenol Compound 37a was used in place of Compound 31a and carried forward to prepare 2-methylsulfanyl-7-(3-trifluoromethoxy-phenoxy)-thiazolo[4,5-b]pyridine-6-carbonitrile Compound 37b.

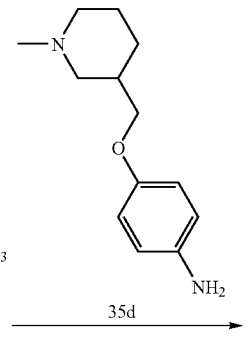

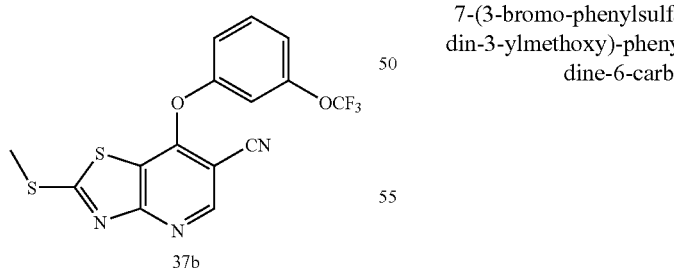

Cpd 37

Using the procedure of Example 1, Compound 37b, replacing Compound 1m, and Compound 35d, replacing Compound 1n, were carried forward to prepare Compound 37 as a trifluoroacetate salt. MS 556 (MH+).

EXAMPLE 38

7-(3-bromo-phenylsulfanyl)-2-[4-(1-methyl-piperidin-3-ylmethoxy)-phenylamino]-thiazolo[4,5-b]pyridine-6-carbonitrile (Cpd 38)

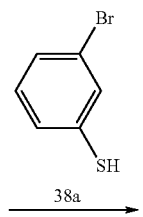

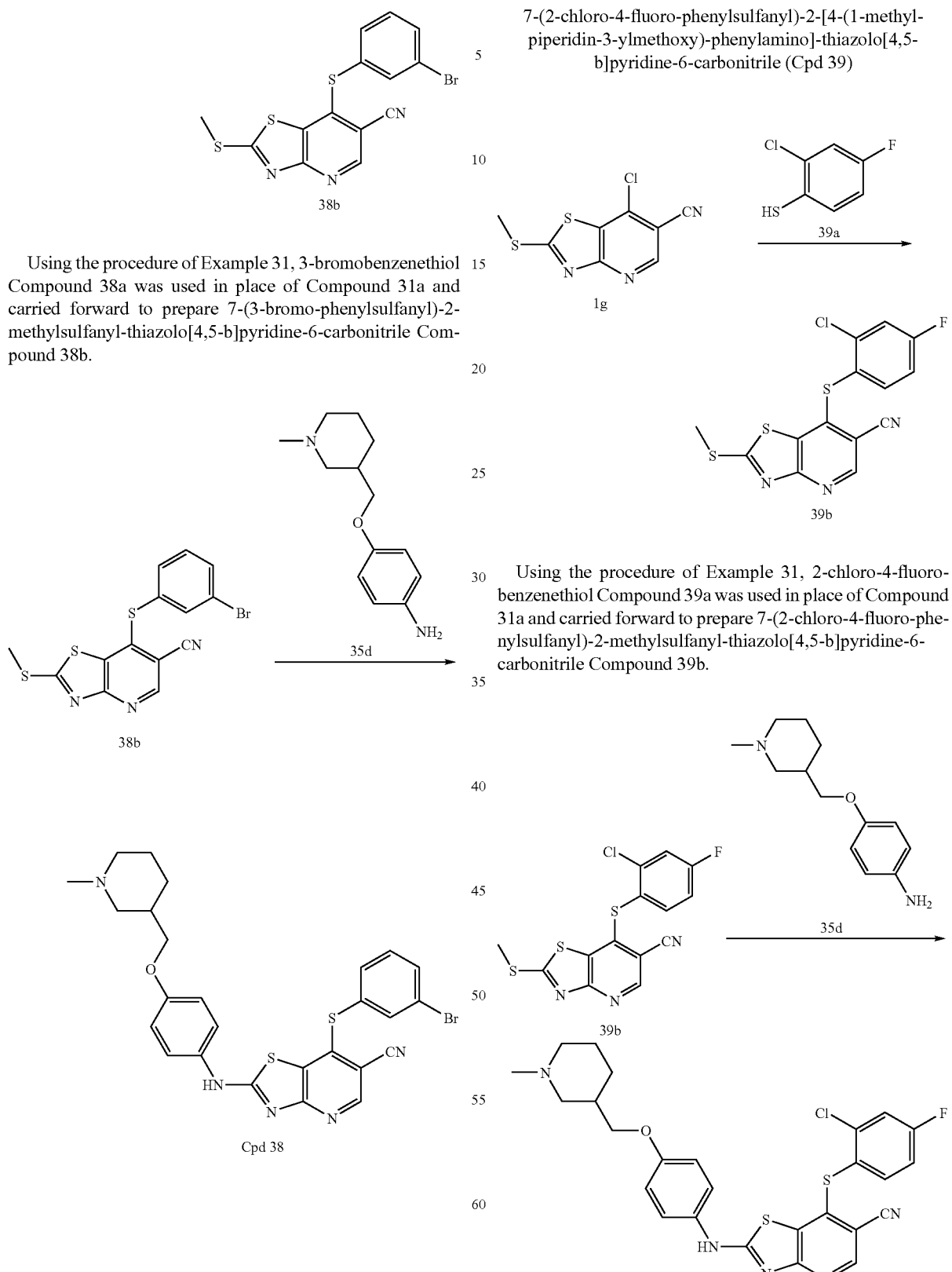

Using the procedure of Example 31, 3-bromobenzenethiol Compound 38a was used in place of Compound 31a and carried forward to prepare 7-(3-bromo-phenylsulfanyl)-2-methylsulfanyl-thiazolo[4,5-b]pyridine-6-carbonitrile Compound 38b.

Using the procedure of Example 1, Compound 38b, replacing Compound 1m, and Compound 35d, replacing Compound 1n, were carried forward to prepare Compound 38 as a trifluoroacetate salt. MS 566, 568 (MH$^+$).

EXAMPLE 39

7-(2-chloro-4-fluoro-phenylsulfanyl)-2-[4-(1-methyl-piperidin-3-ylmethoxy)-phenylamino]-thiazolo[4,5-b]pyridine-6-carbonitrile (Cpd 39)

Using the procedure of Example 31, 2-chloro-4-fluoro-benzenethiol Compound 39a was used in place of Compound 31a and carried forward to prepare 7-(2-chloro-4-fluoro-phenylsulfanyl)-2-methylsulfanyl-thiazolo[4,5-b]pyridine-6-carbonitrile Compound 39b.

Using the procedure of Example 1, Compound 39b, replacing Compound 1m, and Compound 35d, replacing Compound 1n, were carried forward to prepare Compound 38 as a trifluoroacetate salt. MS 540, 542 (MH+).

EXAMPLE 40

7-(5-chloro-benzo[1,3]dioxol-4-ylamino)-2-[4-(1-methyl-piperidin-3-ylmethoxy)-phenylamino]-thiazolo[4,5-b]pyridine-6-carbonitrile (Cpd 40)

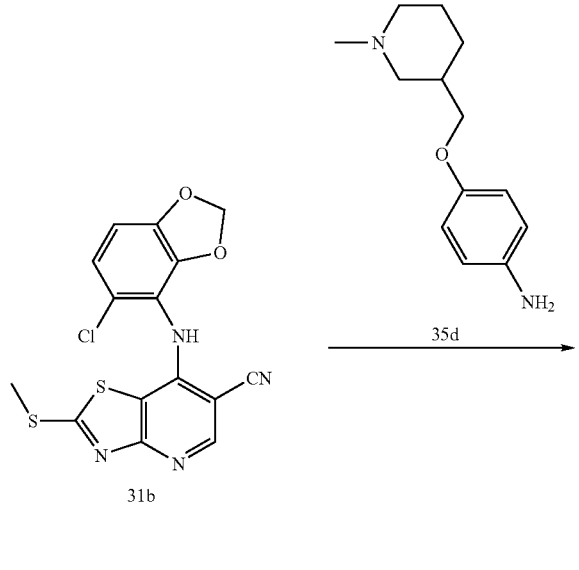

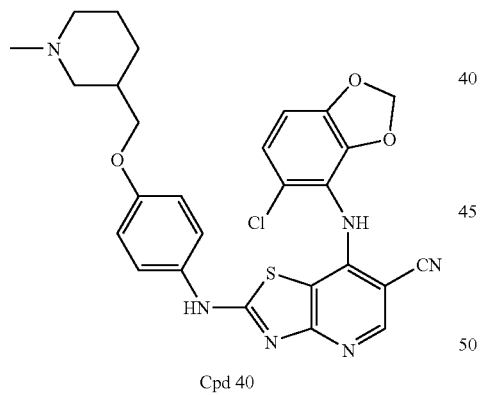

Cpd 40

Using the procedure of Example 1, Compound 31b, replacing Compound 1m, and Compound 35d, replacing Compound 1n, were carried forward to prepare Compound 40 as a trifluoroacetate salt. $^1$H NMR (DMSO-$d_6$) δ 10.73 (s, 1H), 9.35 (br s, 1H), 9.22 (s, 1H), 8.46 (s, 1H), 7.62 (d, J=8.7 Hz, 2H), 7.11 (d, J=8.1 Hz, 1H), 7.08 (d, J=8.1 Hz, 1H), 6.10 (s, 2H), 3.99-3.93 (m, 1H), 3.85-3.78 (m, 1H) 3.62-3.39 (m, 2H), 2.90-2.77 (m, 5H), 2.26-2.14 (m, 1H), 1.94-1.61 (m, 3H), 1.33-1.20 (m, 1 H). MS 549, 551 (MH+).

EXAMPLE 41

7-(5-chloro-benzo[1,3]dioxol-4-ylamino)-2-(4-piperidin-1-ylmethyl-phenylamino)-thiazolo[4,5-b]pyridine-6-carbonitrile (Cpd 41)

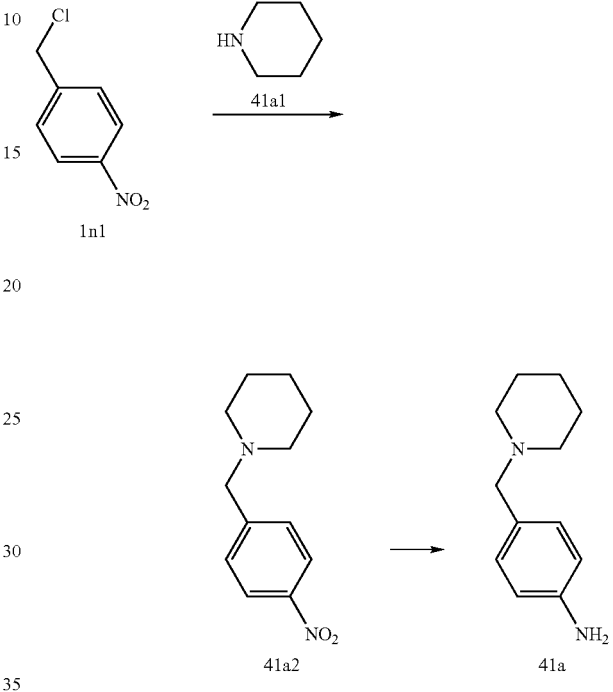

Using the procedure of Example 1, piperidine Compound 41a1 was used in place of Compound 1n2 and was carried forward to prepare 4-piperidin-1-ylmethyl-phenylamine Compound 41a.

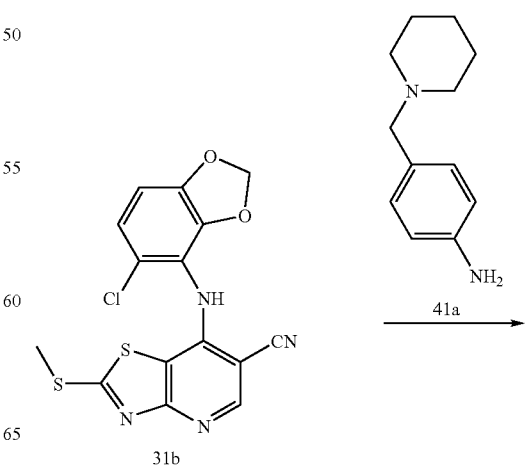

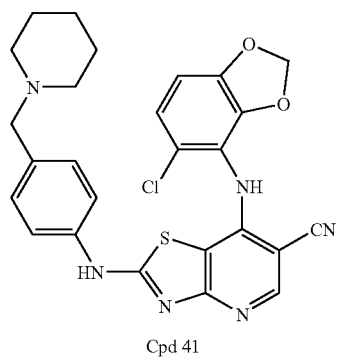

Cpd 41

Using the procedure of Example 1, Compound 31b, used in place of Compound 1m, and Compound 41a, used in place of Compound 1n, were carried forward to prepare Compound 41 which was isolated as a trifluoroacetate salt. $^1$H NMR (DMSO-d$_6$) δ 11.05(s, 1H), 9.40-9.28 (m, 2H), 8.50 (s, 1H), 7.80 (d, J=8.6 Hz, 2H), 7.49 (d, J=8.6Hz, 2H), 7.13 (d, J=8.5 Hz, 1H), 7.10 (d, J=8.5 Hz, 1H), 6.11 (s, 2H), 4.24 (s, 2H), 3.37-3.27 (m, 2H) 2.92-2.78 (m, 2H), 1.87-1.76 (m, 2H), 1.73-1.53 (m, 3H), 1.42-1.28 (m, 1H). MS 519, 521 (MH$^+$).

EXAMPLE 42

7-(5-chloro-benzo[1,3]dioxol-4-ylamino)-2-[3-methoxy-4-(2-morpholin-4-yl-ethoxy)-phenylamino]-thiazolo[4,5-b]pyridine-6-carbonitrile (Cpd 42)

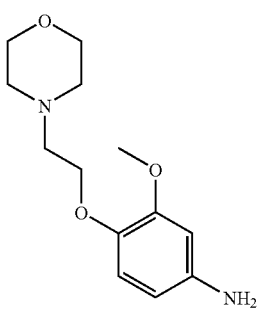

42a

A mixture of 2-methoxy-4-nitrophenol Compound 42a1 (1.0 g, 5.4 mmol), potassium carbonate (1.5 g, 10.9 mmol) and 4-(2-chloroethyl)-morpholine hydrochloride Compound 42a2 (1.05 g, 5.64 mmol) in DMF (10 mL) was heated under microwave conditions to 140° C. for 30 minutes. The reaction mixture was filtered, diluted with EtOAc and subsequently washed with water, then brine. The organic layer was dried over sodium sulfate and concentrated to yield 4-[2-(2-methoxy-4-nitro-phenoxy)-ethyl]-morpholine Compound 42a3 (1.4 g). MS 283 (MH+).

A solution of 10% Pd/C (0.25 g) was added to a solution of 4-[2-(2-methoxy-4-nitro-phenoxy)-ethyl]-morpholine Compound 42a3 (1.4 g, 5.0 mmol) in EtOAc (50 mL). The solution was exposed to 40 PSI of hydrogen gas for a period of 1 hr. The catalyst was removed by filtration through Celite 545 and the solvent was removed to give 3-methoxy-4-(2-morpholin-4-yl-ethoxy)-phenylamine Compound 42a (1.1 g). MS 253 (MH+).

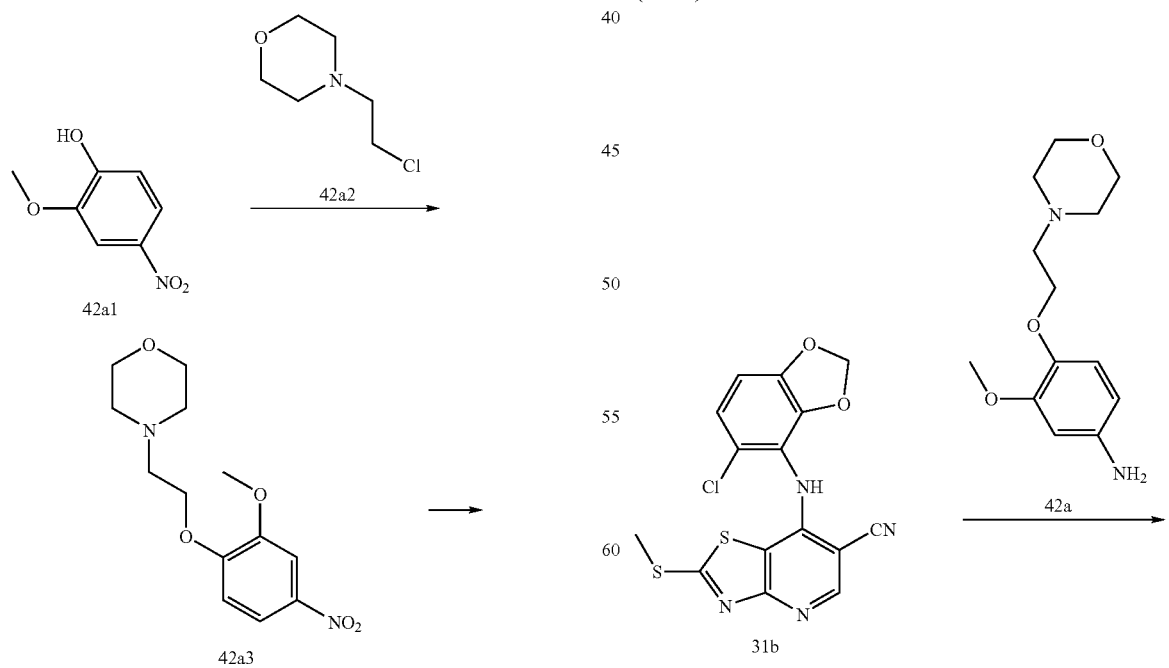

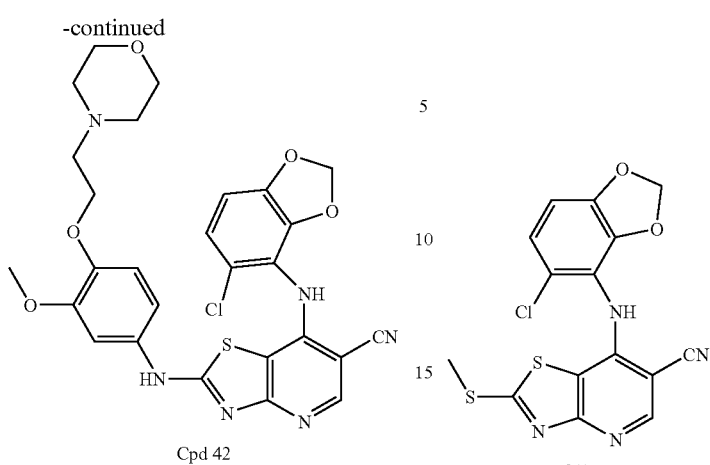

Cpd 42

Using the procedure of Example 1, Compound 31b, used in place of Compound 1m, and Compound 42a, used in place of Compound 1n, were carried forward to prepare Compound 42, which was isolated as a trifluoroacetate salt. MS 581, 583 (MH⁺).

EXAMPLE 43

7-(5-chloro-benzo[1,3]dioxol-4-ylamino)-2-[3-methoxy-4-(tetrahydro-pyran-2-ylmethoxy)-phenylamino]-thiazolo[4,5-b]pyridine-6-carbonitrile (Cpd 43)

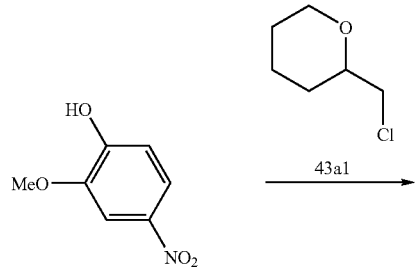

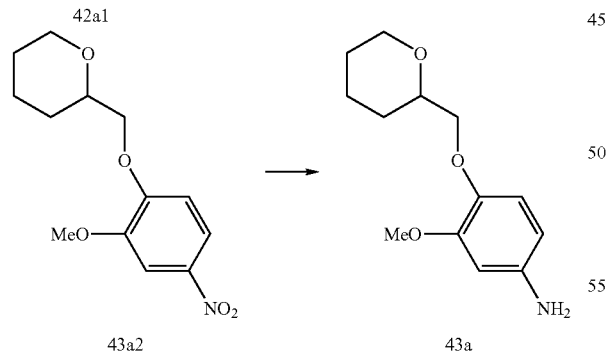

Using the procedure of Example 42, 2-chloromethyl-tetrahydropyran Compound 43a1 was used in place of Compound 42a2 and carried forward to provide 2-(2-methoxy-4-nitro-phenoxymethyl)-tetrahydro-pyran Compound 43a2. Using the procedure of Example 1, Compound 43a2 was used in place of Compound 1n3 and carried forward to prepare 3-methoxy-4-(tetrahydro-pyran-2-ylmethoxy)-phenylamine Compound 43a.

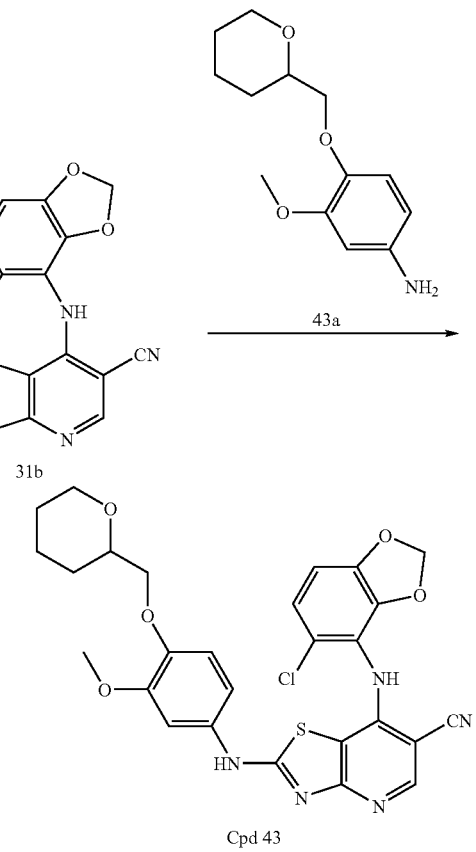

Cpd 43

Using the procedure of Example 1, Compound 31b, used in place of Compound 1m, and Compound 43a, used in place of Compound 1n, were carried forward to prepare Compound 43, which was isolated as a trifluoroacetate salt. MS 566, 568 (MH⁺).

EXAMPLE 44

7-(5-chloro-benzo[1,3]dioxol-4-ylamino)-2-[4-({[(2R)-tetrahydro-furan-2-ylmethyl]-amino}-methyl)-phenylamino]-thiazolo[4,5-b]pyridine-6-carbonitrile (Cpd 44)

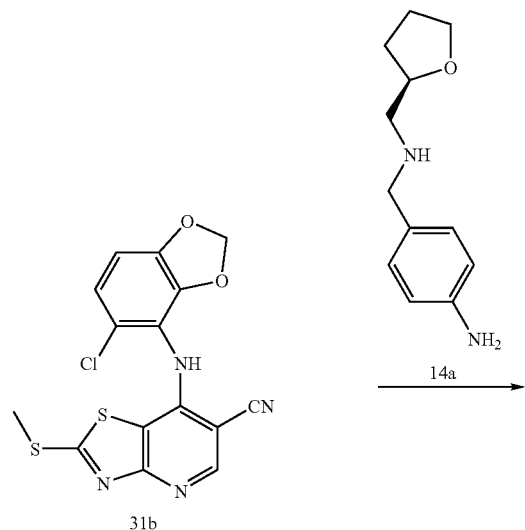

-continued

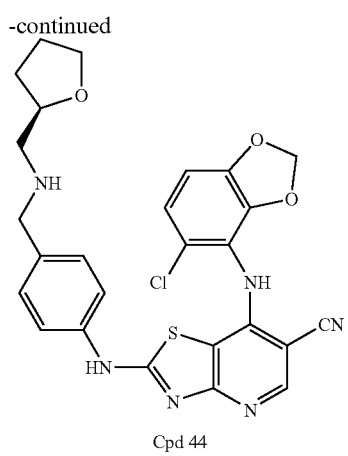

Cpd 44

Using the procedure of Example 1, Compound 31b, used in place of Compound 1m, and Compound 14a, used in place of Compound 1n, were carried forward to prepare Compound 44, which was isolated as a trifluoroacetate salt. $^1$H NMR (DMSO-d$_6$) δ 11.00 (s, 1H), 9.30 (s, 1H), 8.91 (br s, 1H), 8.50 (s, 1H), 7.77 (d, J=8.6 Hz, 2 H), 7.49 (d, J=8.6Hz, 2H), 7.12 (d, J=8.4 Hz, 1H), 7.10(d, J=8.4 Hz, 1H), 6.11 (s, 2H), 4.20-3.67 (m, 5H), 3.07-2.97 (m, 1H), 2.91-2.79 (m, 1H), 2.05-1.94 (m, 1H), 1.91-1.78 (m, 2H), 1.59-1.47 (m, 1H). MS 535, 537 (MH$^+$).

EXAMPLE 45

7-(5-chloro-benzo[1,3]dioxol-4-ylamino)-2-(4-pyr-rolidin-1-ylmethyl-phenylamino)-thiazolo[4,5-b]pyridine-6-carbonitrile (Cpd 45)

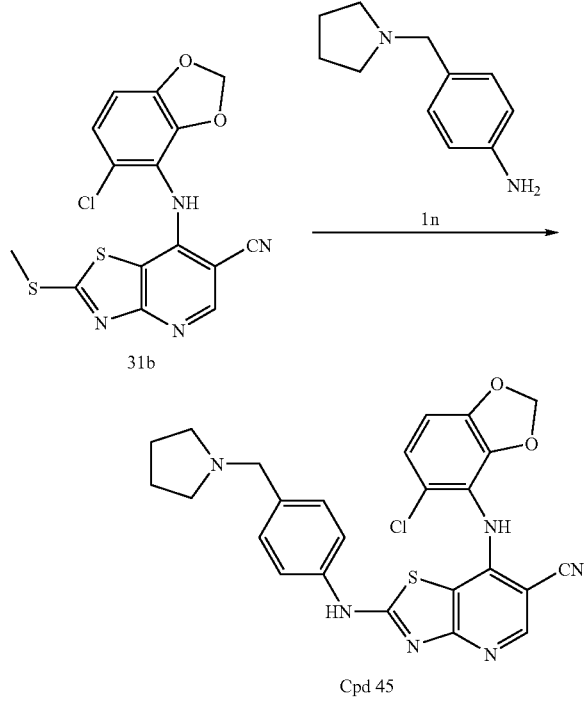

Cpd 45

Using the procedure of Example 1, Compound 31b was used in place of Compound 1m and carried forward to prepare Compound 45, which was isolated as a trifluoroacetate salt. $^1$H NMR (DMSO-d$_6$) δ 11.04 (s, 1H), 9.97 (br s, 1H), 9.32 (s, 1 H), 8.51 (s, 1H), 7.80 (d, J=8.4Hz, 2H), 7.51 (d, J=8.4Hz, 2H), 7.12 (d, J=8.2 Hz, 1H), 7.10 (d, J=8.2 Hz, 1H), 6.12 (s, 2H), 4.32 (s, 2H), 3.42-3.31 (m, 2H), 3.14-3.02 (m, 2H), 2.09-1.97 (m, 2H), 1.92-1.79 (m, 2H). MS 505, 507 (MH$^+$).

EXAMPLE 46

7-(5-chloro-benzo[1,3]dioxol-4-ylamino)-2-[4-(4-methyl-piperazin-1-yl methyl)-phenylamino]-thia-zolo[4,5-b]pyridine-6-carbonitrile (Cpd 46)

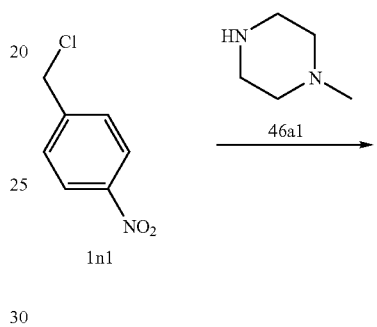

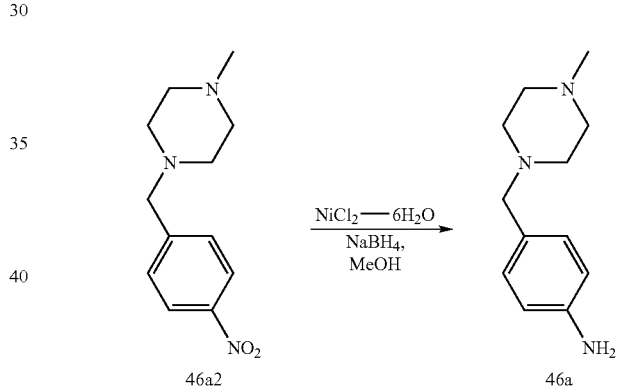

Using the procedure of Example 1, 1-methyl-piperazine Compound 46a1 was used in place of Compound 1n2 and carried forward to prepare 1-methyl-4-(4-nitro-benzyl)-piperazine Compound 46a2. Nickel chloride hexahydrate (45.7 g, 192 mmol) was added to a solution of Compound 46a2 (17.9 g, 87.4 mmol) in methanol (250 mL). Twenty portions of sodium borohydride (500 mg each, 264 mmol total) were then added to the reaction mixture over a period of about 2 hr. The mixture was then carefully diluted at 0° C. with concentrated HCl to give a transparent green solution. The mixture was subsequently washed with ethyl ether. The cooled aqueous layer was adjusted to pH 10 with NH$_4$OH (28%) and then extracted with EtOAc. The combined organic layers were dried over MgSO$_4$, then filtered and evaporated in vacuo to give 4-(4-methyl-piperazin-1-ylmethyl)-phenylamine Compound 46a (17.6 g) as a yellow foam. $^1$H NMR (DMSO-d$_6$) δ 6.91 (d, J=8.2 Hz, 2H); 6.50 (d, J=8.2 Hz, 2H); 4.94 (br s, 2H); 3.28 (s, 2H); 2.44-2.26 (m, 8H); 2.19 (s, 3H).

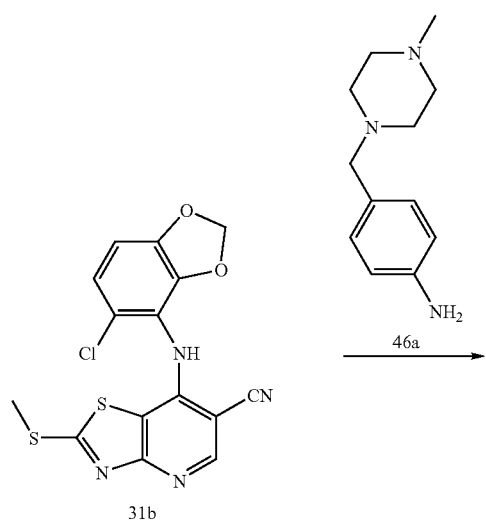
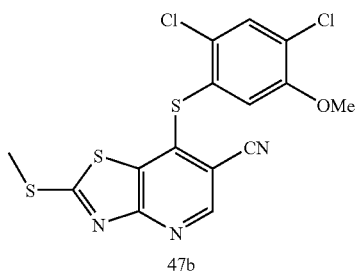

Using the procedure of Example 1, Compound 31b, used in place of Compound 1m, and Compound 46a, used in place of Compound 1n, were carried forward to prepare Compound 46, which was isolated as a trifluoroacetate salt. MS 534, 536 (MH$^+$).

EXAMPLE 47

7-(2,4-dichloro-5-methoxy-phenylamino)-2-(4-morpholin-4-ylmethyl-phenylamino)-thiazolo[4,5-b]pyridine-6-carbonitrile (Cpd 47)

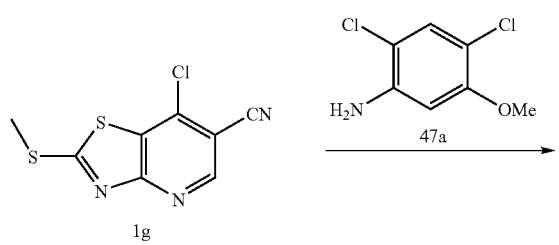

Using the procedure of Example 31, 2,4-dichloro-5-methoxyaniline Compound 47a was used in place of Compound 31a and was carried forward to prepare 7-(2,4-dichloro-5-methoxy-phenylamino)-2-methylsulfanyl-thiazolo[4,5-b]pyridine-6-carbonitrile Compound 47b.

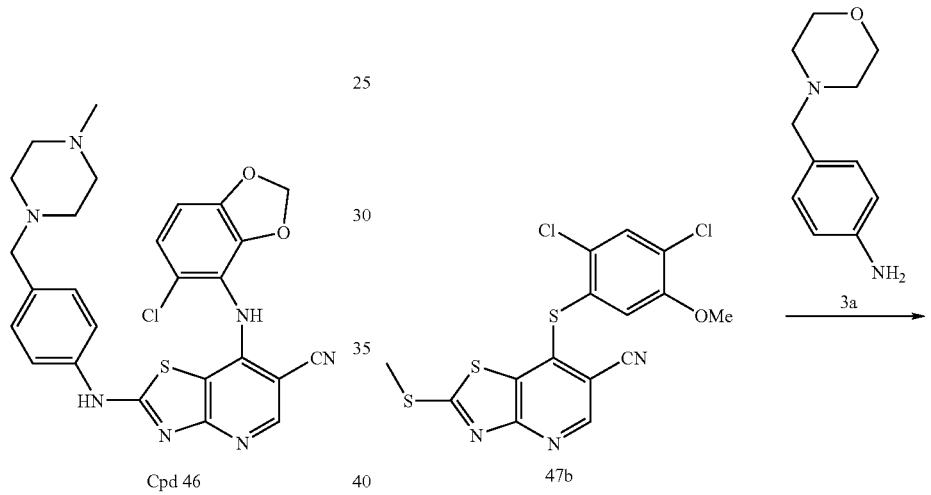

Using the procedure of Example 1, Compound 47b, used in place of Compound 1m, and Compound 3a, used in place of Compound 1n, were carried forward to prepare Compound 47, which was isolated as a trifluoroacetic acid salt. $^1$H NMR (DMSO-d$_6$) δ 11.02 (s, 1H), 10.02 (br s, 1H), 9.55 (s, 1H), 8.54 (s, 1H), 7.84-7.78 (m, 3H), 7.50 (d, J=8.4 Hz, 2H), 7.35 (s, 1H), 4.31 (s, 2H), 4.01-3.82 (m, 5H), 3.67-3.57 (m, 2H), 3.31-3.20 (m, 2H), 3.16-3.03 (m, 2H). MS 541, 543 (MH$^+$).

EXAMPLE 48

7-(3-bromo-phenylamino)-2-(4-morpholin-4-ylm-ethyl-phenylamino)-thiazolo[4,5-b]pyridine-6-carbonitrile (Cpd 48)

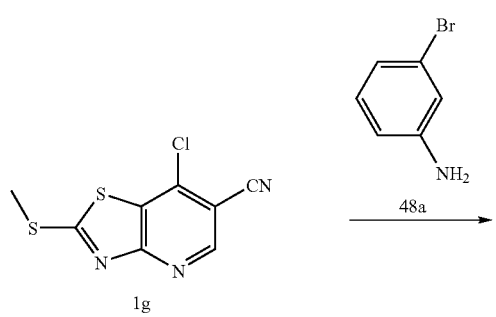

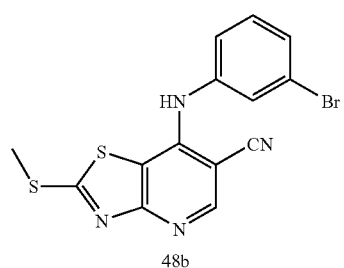

Using the procedure of Example 1, 3-bromo-phenylamine Compound 48a was used in place of Compound 1l and was carried forward to prepare 7-(3-bromo-phenylamino)-2-methylsulfanyl-thiazolo[4,5-b]pyridine-6-carbonitrile Compound 48b.

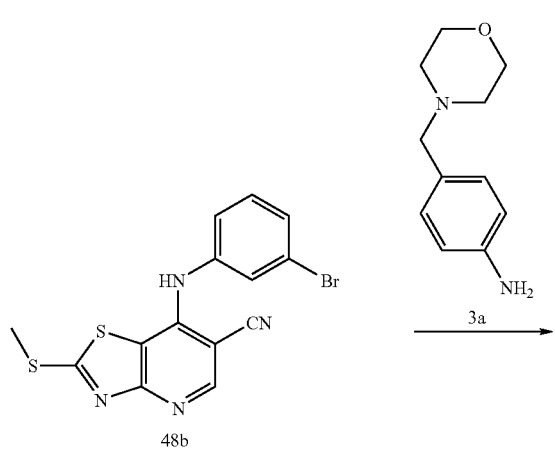

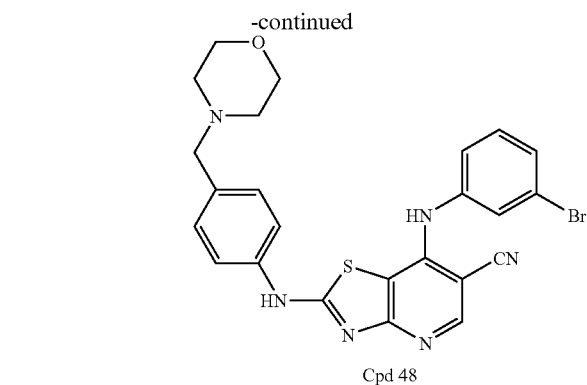

Using the procedure of Example 1, Compound 48a, used in place of Compound 1m, and Compound 3a, used in place of Compound 1n, were carried forward to prepare Compound 48, which was isolated as a trifluoroacetate salt. $^1$H NMR (DMSO-$d_6$) δ 11.07 (s, 1H), 9.90 (br s, 1H), 9.61 (s, 1H), 8.59 (s, 1H), 7.82 (d, J=8.6 Hz, 2H), 7.51 (d, J=8.6 Hz, 2H), 7.47-7.33 (m, 3H), 7.20 (d, J=8.1 Hz, 1H), 4.32 (s, 2H), 4.02-3.91 (m, 2H), 3.67-3.53 (m, 2H), 3.31-3.20 (m, 2H), 3.18-3.02 (m, 2H). MS 521, 523 (MH$^+$).

EXAMPLE 49

7-(5-chloro-benzo[1,3]dioxol-4-ylamino)-2-[4-(2-morpholin-4-yl-ethyl)-phenyl amino]-thiazolo[4,5-b]pyridine-6-carbonitrile (Cpd 49)

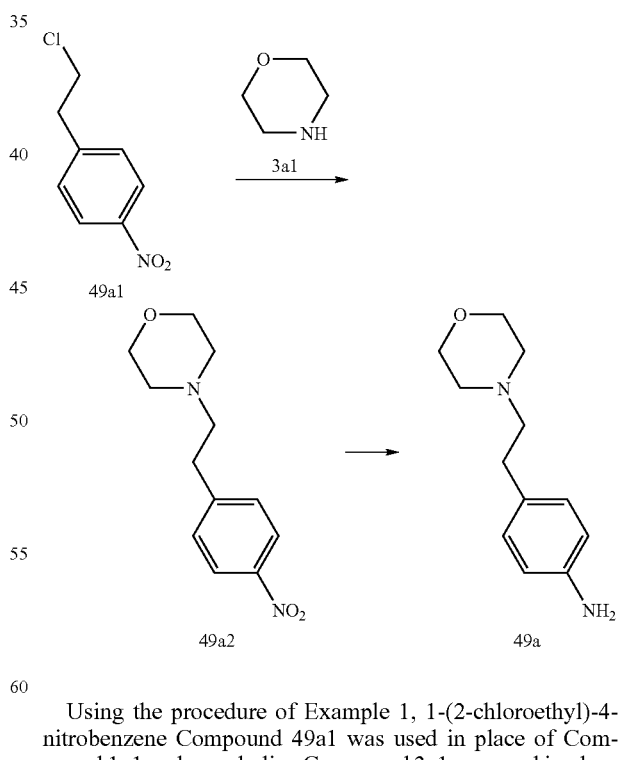

Using the procedure of Example 1, 1-(2-chloroethyl)-4-nitrobenzene Compound 49a1 was used in place of Compound 1n1 and morpholine Compound 3a1 was used in place of Compound 1n2 to prepare 4-[2-(4-nitrophenyl)ethyl]-morpholine Compound 49a2, which was carried forward to prepare 4-(2-morpholin-4-yl-ethyl)-phenylamine Compound 49a.

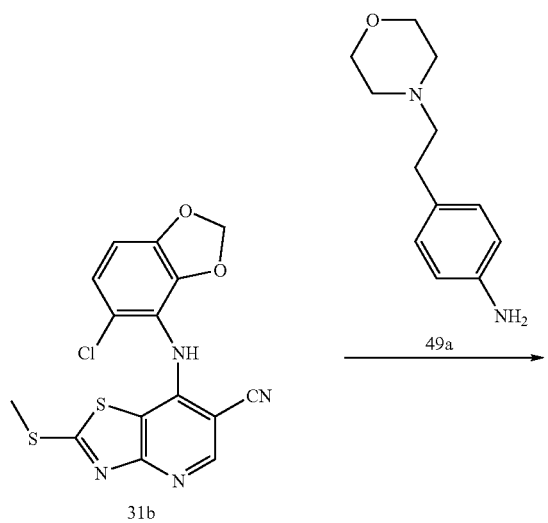

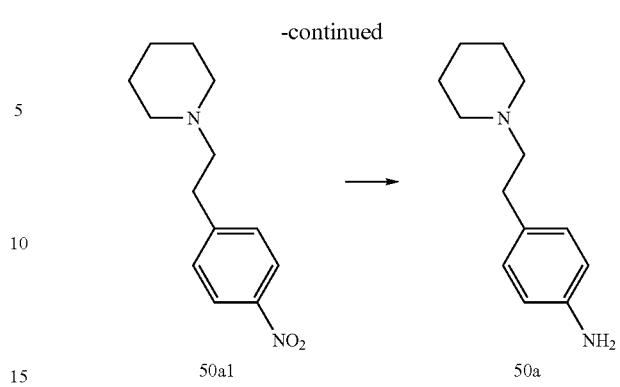

Using the procedure of Example 1, Compound 49a1 was used in place of Compound 1n1 and piperidine Compound 41a1 was used in place of Compound 1n2 to prepare 1-[2-(4-nitro-phenyl)-ethyl]-piperidine Compound 50a1, which was carried forward to prepare 4-(2-piperidin-1-yl-ethyl)-phenylamine Compound 50a.

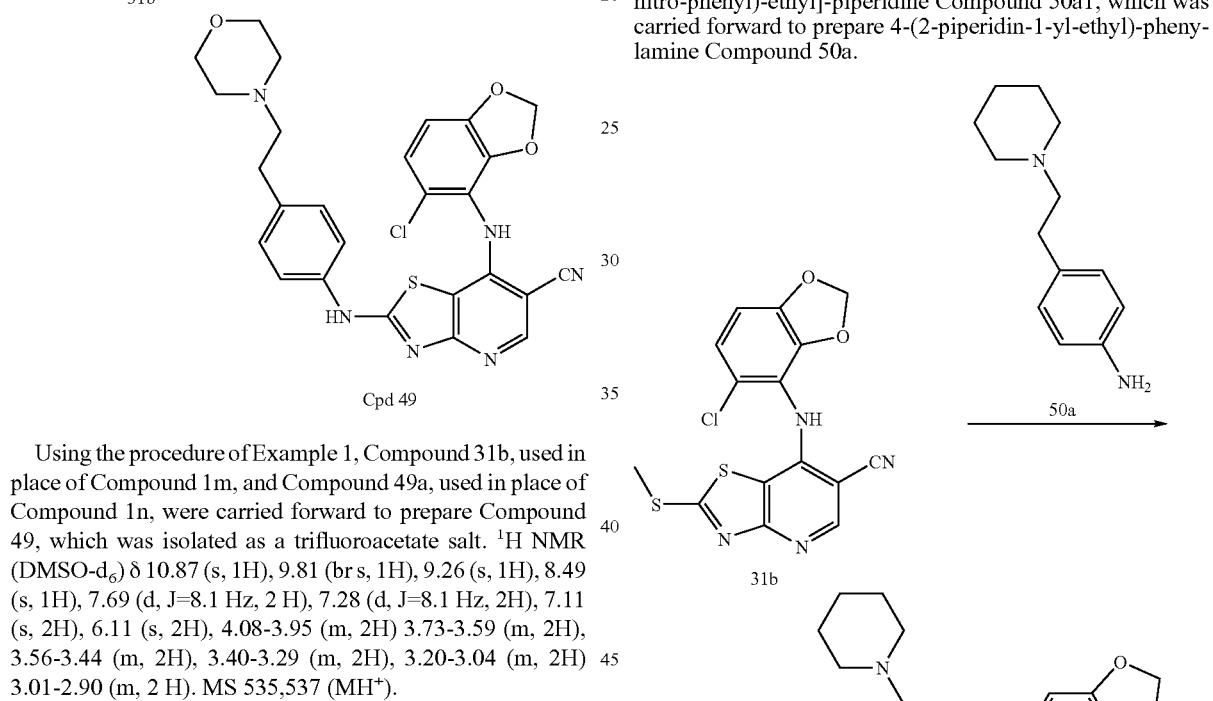

Using the procedure of Example 1, Compound 31b, used in place of Compound 1m, and Compound 49a, used in place of Compound 1n, were carried forward to prepare Compound 49, which was isolated as a trifluoroacetate salt. $^1$H NMR (DMSO-d$_6$) δ 10.87 (s, 1H), 9.81 (br s, 1H), 9.26 (s, 1H), 8.49 (s, 1H), 7.69 (d, J=8.1 Hz, 2H), 7.28 (d, J=8.1 Hz, 2H), 7.11 (s, 2H), 6.11 (s, 2H), 4.08-3.95 (m, 2H) 3.73-3.59 (m, 2H), 3.56-3.44 (m, 2H), 3.40-3.29 (m, 2H), 3.20-3.04 (m, 2H) 3.01-2.90 (m, 2 H). MS 535,537 (MH$^+$).

EXAMPLE 50

7-(5-chloro-benzo[1,3]dioxol-4-ylamino)-2-[4-(2-piperidin-1-yl-ethyl)-phenylamino]-thiazolo[4,5-b]pyridine-6-carbonitrile (Cpd 50)

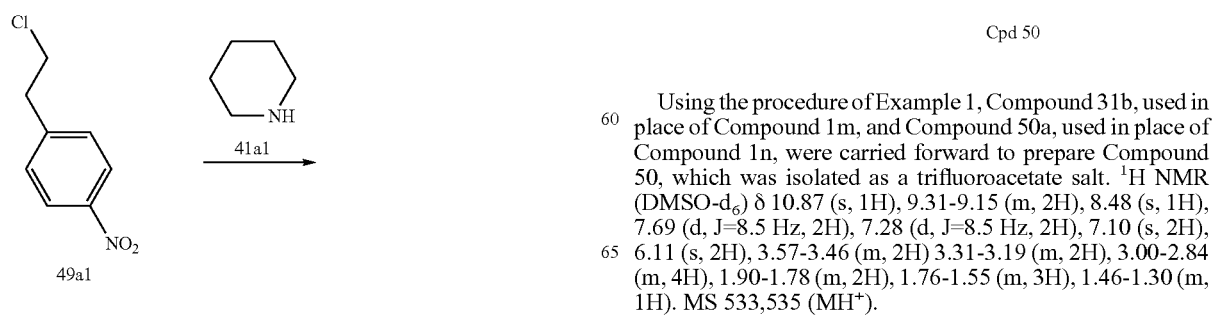

Using the procedure of Example 1, Compound 31b, used in place of Compound 1m, and Compound 50a, used in place of Compound 1n, were carried forward to prepare Compound 50, which was isolated as a trifluoroacetate salt. $^1$H NMR (DMSO-d$_6$) δ 10.87 (s, 1H), 9.31-9.15 (m, 2H), 8.48 (s, 1H), 7.69 (d, J=8.5 Hz, 2H), 7.28 (d, J=8.5 Hz, 2H), 7.10 (s, 2H), 6.11 (s, 2H), 3.57-3.46 (m, 2H) 3.31-3.19 (m, 2H), 3.00-2.84 (m, 4H), 1.90-1.78 (m, 2H), 1.76-1.55 (m, 3H), 1.46-1.30 (m, 1H). MS 533,535 (MH$^+$).

EXAMPLE 51

2-[4-(4-methyl-piperazin-1-ylmethyl)-phenylamino]-7-(4-phenoxy-phenylamino)-thiazolo[4,5-b]pyridine-6-carbonitrile (Cpd 51)

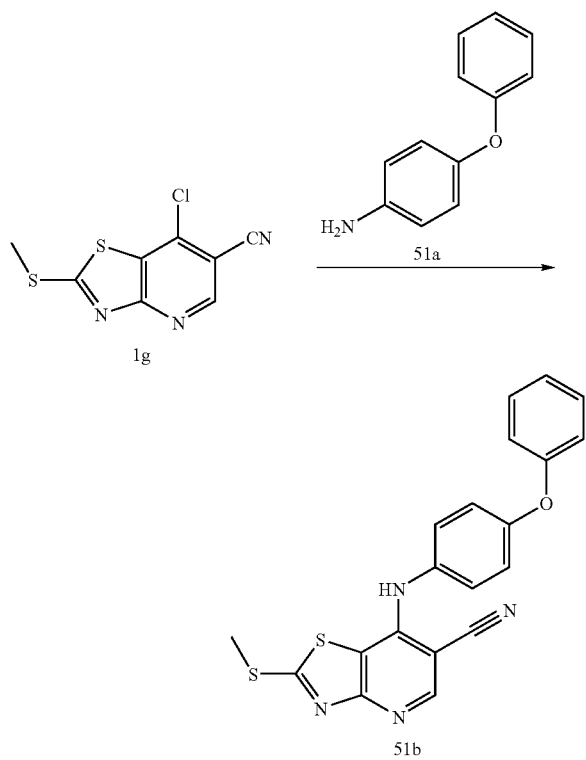

The procedure of Example 1 and 4-phenoxy-phenylamine Compound 51a used in place of 3-chloro-4-fluoro-phenylamine Compound 11 were used to prepare 2-methylsulfanyl-7-(4-phenoxy-phenylamino)-thiazolo[4,5-b]pyridine-6-carbonitrile Compound 51b.

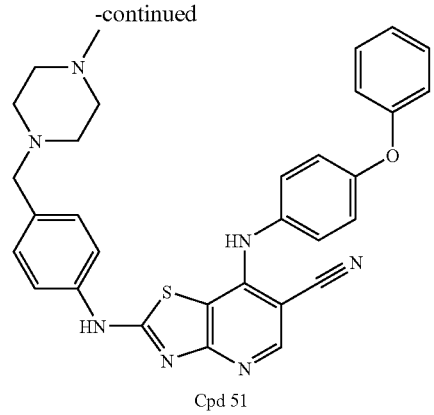

The procedure of Example 1, Compound 51b used in place of Compound 1m, and 4-(4-methyl-piperazin-1-ylmethyl)-phenylamine Compound 46a used in place of Compound 1n were used to prepare Compound 51, which was isolated as a trifluoroacetate salt. MS 548 (MH+).

Biological Examples

The ability of the compounds to treat or ameliorate protein kinase mediated disorders was determined using the following procedures.

EXAMPLE 52

EGFR Kinase Assay

The EGFR kinase used was a fusion of Glutathione-S-Transferase (GST) and a PCR amplified intracellular portion of EGFR (NM_005228). The intracellular portion of EGFR started at nucleotide 2189 (corresponding to amino acid 667) and ended at the termination codon. The portion was PCR amplified with primers that added the lambda attB sequences to each end, recombined into an entry vector, then into a GST destination vector (as described in Gateway Technologies Manual by Invitrogen Corporation, Carlsbad, Calif.).

The destination vector was recombined in the DH10BAC strain of bacteria to produce a bacmid. The bacmid was transfected into Sf 9 cells and the supernatant containing the baculovirus was collected. The GSTEGFR protein was purified using large cultures of Sf 9 cells infected with stock virus. After an appropriate period of time, the cells were collected and lysed. The GSTEGFR was then purified from the lysate on Glutathione-Sepharose columns (as described by Amersham Biosciences, Buckinghamshire, United Kingdom).

The EGFR substrate was prepared by biotinylating poly-GluTyr (128 mg) (Sigma, St. Louis, Mo.) in a 1×PBS buffer incubated together with a 12-fold molar excess of Sulfo-NHS-LC-Biotin on ice for at least 2 hrs. The free biotin was separated from the biotinylated polyGluTyr on a gel filtration column.

A mixture of a 10× kinase buffer (500 mM Tris at pH 8.0, 100 mM Magnesium Chloride and 1 mM Sodium Vanadate), DTT (1 mM final from 500 mM stock), ATP (5 µM final from 10 mM stock), biotinylated polyGluTyr (10 µg/µL stock), γ-$^{33}$PATP (10 µCi/µL stock) and water was added to each well (90 µL/well) of a Streptavidin Flashplate (Perkin Elmer, Wellesley, Mass.).

Test compound in 100% DMSO (2 µL) was added to the appropriate wells. Diluted GSTEGFR (1:300 dilution in 50 mM Tris at pH 8.0 and 0.1% bovine serum albumin) (10 µL) was added to the wells to initiate the reactions.

The plates were incubated at 30° C. for 1 hr with shaking. The reacted contents were removed and the plates were sequentially washed three times with a 1×PBS stop buffer (300 μL without Magnesium and Calcium) and 100 mM EDTA. After the final wash, the same stop buffer (200 μL) was added to the wells. The plates were then sealed and read on the TopCount scintillation counter.

Test compounds were assayed in triplicate at 16 concentrations at half-log dilutions starting at 200 uM. A maximum and minimum signal for the assay was determined on each plate. The percent inhibition of a test compound was calculated accord to the formula $$\left[\frac{(\text{max signal} - \text{test compound})}{(\text{max signal} - \text{min signal})}\right](100) = \% \text{ inhibition}$$

For a series of test concentrations, the $IC_{50}$ was derived by graphing percent inhibition against the log of the concentrations tested for a given compound. The $IC_{50}$ results are shown in Table 1. For those compounds without an $IC_{50}$, the percent inhibition results are shown at a test concentration of 2 μM.

TABLE 1

EGFR $IC_{50}$ (μM)

| Cpd | $IC_{50}$ |
|---|---|
| 1 | 0.02255 |
| 2 | 0.078 |
| 3 | 0.04367 |
| 4 | 0.049 |
| 5 | 0.06367 |
| 6 | 0.053 |
| 7 | 0.0285 |
| 8 | 2.6335 |
| 9 | 2.6305 |
| 10 | 0.0565 |
| 11 | 0.04173 |
| 12 | 15.85 |
| 13 | 3.28 |
| 14 | 0.0293 |
| 15 | 0.07605 |
| 16 | 0.07645 |
| 17 | 0.03994 |
| 18 | 0.08575 |
| 19 | 0.0795 |
| 20 | 0.3776, 0.941 |
| 21 | 0.04459 |
| 22 | 0.85335 |
| 23 | 0.02045 |
| 24 | 0.0333 |
| 25 | 0.04331 |
| 26 | 0.15845 |
| 27 | 0.20705 |
| 28 | 0.3272 |
| 29 | 0.0696 |
| 30 | 0.06772 |
| 31 | 0.06035 |
| 34 | 1.452 |
| 35 | 0.461 |
| 36 | 8.757 |
| 37 | 7.212 |
| 38 | 2.199 |
| 39 | 3.257 |
| 40 | 46% |
| 41 | 44% |
| 42 | 18% |
| 43 | 4% |
| 44 | 47% |
| 51 | 0% |

EXAMPLE 53 c-Src Kinase Assay

A minute of a 10× kinase buffer (80 mM MOPS at pH 7.0, 2 mM EDTA and 100 mM Magnesium Chloride), ATP (5 μM final from a 10 mM stock), a Cdc2 peptide KVEKIGEG-TYGVVYK (100 μM final from a 2.5 mM stock), γ-$^{33}$P ATP (10 μCi/μL stock) and water (20 μL/well) was added to each well of a Streptavidin Flashplate.

Test compound in 100% DMSO (0.5 μL) was added to the appropriate wells. Diluted c-Src kinase (human) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%), and 1 mg/mL bovine serum albumin) (2.5 μL) was added to the wells to initiate the reactions. The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

The percent inhibitions and $IC_{50}$ values were derived according to the procedure described in Example 52. The $IC_{50}$ results are shown in Table 2. For those compounds without an $IC_{50}$, the percent inhibition results are shown at a test concentration of [1]1 μM or [2]1.6 μM.

TABLE 2 c-SRC $IC_{50}$ (μM)

| Cpd | $IC_{50}$ |
|---|---|
| 20 | 0.011 (h) |
| 23 | [1]–2% (h) |
| 24 | [1]15% (h) |
| 25 | 1.406 |
| 35 | [2]11% |
| 36 | [2]4% |
| 37 | [2]3% |
| 38 | [2]4% |
| 39 | >100 |
| 40 | 2.394 |
| 41 | 0.079 |
| 42 | 1.381 |
| 43 | >100 |
| 44 | 0.126 |
| 45 | 0.145 |
| 46 | 0.389 |
| 51 | 0% |

EXAMPLE 54

Lyn Kinase Assay

A mixture of a 10× kinase buffer (500 mM MOPS at pH 7.5, 1 mM EGTA, 1 mM Sodium Vanadate, 1% β-mercaptoethanol and 100 mM Magnesium Acetate), ATP (5 μM final from a 10 mM stock), polyGluTyr (0.1 mg/mL final from a 1 mg/mL stock), γ-$^{33}$P ATP (10 μCi/μL stock) and water (20 μL/well) was added to each well of a Streptavidin Flashplate.

Test compound in 100% DMSO (0.5 μL) was added to the appropriate wells. Diluted Lyn kinase (human) (Upstate Biotechnology, Lake Placid, N.Y.) (diluted in a buffer consisting of 50 mM Tris at pH 7.5, 0.1 mM EGTA, Sodium Vanadate (0.1 mM), β-mercaptoethanol (0.1%) and 1 mg/mL bovine serum albumin) (2.5 μL) was added to the wells to initiate the reactions.

The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

The percent inhibitions and $IC_{50}$ values were derived according to the procedure described in Example 52. The $IC_{50}$ results are shown in Table 3. For those compounds without an $IC_{50}$, the percent inhibition results are shown at a test concentration of [1] 1 μM or [2] 1.6 μM.

TABLE 3

| Cpd | LYN $IC_{50}$ (μM) $IC_{50}$ |
|---|---|
| 20 | 0.011 (h), 0.009 (m) |
| 23 | [1]8% (h), [1]42% (m) |
| 24 | [1]–5% (h), [1]10% (m) |
| 25 | 0.224 (h), 0.79 (m) |
| 51 | [2]37% (h) |

EXAMPLE 55

HER-2 Kinase Assay

The HER-2 kinase used was purified at Proqinase (Freiburg, Germany) from a construct that consisted of a fusion of GST (Glutathione-S-Transferase), HIS6-Thrombin and the nucleotides encoding amino acids 679 to 1255 of HER-2.

A mixture of a 10× kinase reaction buffer (600 mM Hepes at pH 7.5, 30 mM Magnesium Chloride, 0.03 mM Sodium Vanadate and 500 μg/mL PEG 20,000), DTT (1.2 mM final from a 10 mM stock), ATP (1 μM from a 10 mM stock), biotinylated polyGluTyr (1.5 ng/μL final from stock of 1 μg/μL prepared by Upstate Biotechnologies, Lake Placid, N.Y.), Manganese Chloride (3 mM final from a 1 M stock), γγ-$^{33}$P-ATP (10 μCi/μL stock) and water (70 μL/well) was added to each well of a Streptavidin Flashplate (Cat. # SMP103, NEN, Boston, Mass.).

Test compound stock (1 μL) was added to the appropriate wells. Diluted GSTHER2 kinase (6.7 ng/μL diluted into 50 mM Tris-HCl at pH 8.0 and 0.1% bovine serum albumin) (30 μL) was added (total volume of 200 ng/well) to initiate the reactions.

The reaction plates were incubated at 30° C. for 1 hr. The reaction was terminated by aspirating the reaction mixture from the plate wells and washing the wells three times with a 1×PBS stop buffer (300 μL) and 100 mM EDTA. After the final wash, the same stop buffer (200 μL) was again added to the wells. The plates were then sealed and read on the Top-Count scintillation counter.

The $IC_{50}$ was derived according to the procedure described in Example 52. The $IC_{50}$ results are shown in Table 4. For those compounds without an $IC_{50}$, the percent inhibition results are shown at a test concentration of 1 μM.

TABLE 4

| Cpd | HER-2 $IC_{50}$ (μM) $IC_{50}$ |
|---|---|
| 2 | 100 |
| 10 | 10 |
| 17 | 46.03 |
| 19 | 100 |
| 24 | 2.06 |
| 25 | 92.74 |
| 51 | >100 |

EXAMPLE 56 c-Abl Kinase Assay

A mixture of a 10× kinase buffer (80 mM MOPS at pH 7.0, 2 mM EDTA and 100 mM Magnesium Acetate), ATP (5 μM final from a 10 mM stock), a peptide EAIYAAPFAKKK (50 μM final from a 0.5 mM stock), γ-$^{33}$P ATP (10 μCi/μL stock) and water is added to each well (20 μL/well) of a Streptavidin Flashplate.

Test compound in 100% DMSO (0.5 μL) is added to the appropriate wells. Diluted c-Abl kinase (human) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%) and 1 mg/mL bovine serum albumin) (2.5 μL) is added to the wells to initiate the reactions.

The reaction plates are incubated at 30° C. for 40 min. The reaction is terminated by the addition of a 3% phosphoric acid solution (5 μL). The reaction product (10 μL) is spotted onto a P30 filtermat and is washed for 5 minutes in phosphoric acid (75 mM). The wash sequence is repeated two more times and is followed with one final wash in methanol. The plates are then dried, sealed and read on the TopCount scintillation counter after 30 μL scintillation fluid is added.

The percent inhibitions and $IC_{50}$ values are derived according to the procedure described in Example 52.

EXAMPLE 57

Cell Proliferation Inhibition Assay

The ability of a test compound to inhibit unregulated cell proliferation may be determined by measuring incorporation of $^{14}$C-labelled thymidine into newly synthesized DNA within cell lines derived from carcinomas originating from several tissues. Accordingly, the anti-proliferative effect of a compound on cells with a variety of phenotypes may be determined.

Carcinoma cell lines include those such as HeLa cervical adenocarcinoma (American Type Culture Collection (ATCC), Virginia, Cat. #CCL-2), A375 malignant melanoma (ATCC CRL-1619), SK-OV-3 ovarian adenocarcinoma (ATCC HTB-77), HCT-116 colon carcinoma (CCL-247), PC-3 prostate adenocarcinoma (ATCC CRL-1435), and MDA-MB-231 (Xenogen Corp.)

The carcinoma cells are trypsinized and counted. The cells (3000-8000 count) are added to each well of a 96-well CytoStar tissue culture treated scintillating microplate (Amersham #RPNQ0160) in complete medium (100 μL) and the plate is then incubated in complete medium for 24 hrs at 37° C. in an inert atmosphere containing 5% $CO_2$. Test compound (1 μL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}$C-thymidine (56 mC/mmol) (NEN #NEC568 or Amersham #CFA532) and complete medium (20 µL to provide 0.2 µCi/well) is then added to each well and the plate is incubated for a third 24 hr period at 37° C. in an atmosphere containing 5% $CO_2$. The plate contents are then discarded, the plate is washed twice with PBS (200 µL) and then PBS (200 µL) is added to each well. The plate is sealed and the degree of methyl $^{14}$C-thymidine incorporation is quantified on a Packard Top Count.

EXAMPLE 58

In Vivo Models—Inhibition of Tumor Growth

The ability of a test compound to inhibit unregulated growth of human tumor cells in vivo may be evaluated by implanting human tumor cells into the hindflank of athymic mice, administering a test compound and then quantifying any change in tumor size.

Human epidermoid A431 carcinoma cells ($10^6$ count) are implanted subcutaneously into the hindflank of female athymic mice (Charles River) and allowed to grow for 6-10 days. After a measurable tumor is established (as determined by baseline caliper measurement), the animal is administered an oral dose of the test compound (in 10% solutol) daily for a period of 30 days. Tumor size is measured every five days and the degree of inhibition is determined by comparing drug-treated animals to vehicle-treated animals.

Variations of this method are intended to include intraperitoneal injection or intravenous infusion as the route of administration and administration of the test compound either alone or in a combination therapy.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of Formula (I)

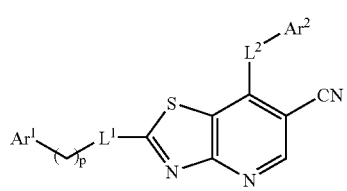

Formula (I)

$L^1$ is selected from the group consisting of $S(C_{1-4}alkyl)$, a bond, $N(R_1)$, $N(R_1)C(O)$ and $C(O)N(R_1)$, wherein $R_1$ is selected from the group consisting of hydrogen, $C_{1-8}alkyl$ and $C_{1-8}alkyl(C_{1-8}alkoxy)$;

p is 0, 1, 2, 3 or 4;

$L^2$ is selected from the group consisting of O, S, $N(R_1)$ and a bond;

$Ar^1$ is aryl, optionally substituted with from one to three substituents independently selected from the group consisting of (1) $C_{1-8}alkyl$,
(2) $C_{2-8}alkenyl$,
(3) $C_{2-8}alkynyl$,
(4) $C_{1-8}alkoxy$,
    wherein (1), (2), (3) and (4) are optionally substituted with one to three substituents independently selected from the group consisting of
    (i) $C_{3-8}cycloalkyl$, and
    (ii) aryl,
    wherein (i) and (ii) are optionally substituted with from one to three substituents independently selected from the group consisting of
        (a) $C_{1-8}alkyl$,
        (b) $C_{1-8}alkoxy$,
        (c) $C_{1-8}alkyl(C_{1-8}alkoxy)$,
        (d) $C_{1-8}alkyl(halogen)_{1-3}$,
        (e) $C_{1-8}alkyl(hydroxy)_{1-3}$,
        (f) $CO_2(C_{1-8}alkyl)$,
        (g) amino optionally mono or disubstituted with $C_{1-8}alkyl$,
        (h) cyano,
        (i) halogen,
        (j) hydroxy,
        (k) $C_{1-8}alkyl(amino)$ optionally mono or disubstituted on amino with $C_{1-8}alkyl$,
        (l) $C_{3-8}cycloalkyl$, and
        (m) $C_{1-8}alkyl(C_{3-8}cycloalkyl)$, and
    (iii) amino optionally mono or disubstituted with a substituent independently selected from the group consisting of
        (a) $C_{1-8}alkyl$,
        (b) $C_{1-8}alkyl(C_{1-8}alkoxy)$,
        (c) $C_{1-8}alkyl(hydroxy)_{1-3}$, and
        (d) $C_{3-8}cycloalkyl$,
(5) amino optionally mono or disubstituted with a substituent independently selected from the group consisting of
    (i) $C_{1-8}alkyl$,
    (ii) $C_{1-8}alkyl(C_{1-8}alkoxy)$,
    (iii) $C_{1-8}alkyl(amino)$ optionally mono or disubstituted on amino with $C_{1-8}alkyl$,
    (iv) $C_{1-8}alkyl(hydroxy)_{1-3}$, and
    (v) $C_{3-8}cycloalkyl$,
(6) cyano,
(7) halogen,
(8) hydroxy,
(9) $C_{3-8}cycloalkyl$,
(10) aryl,
(11) oxy substituted with a substituent selected from the group consisting of
    (i) $CF_3$,
    (ii) $C_{3-8}cycloalkyl$, and
    (iii) aryl,
(12) C(O) substituted with a substituent selected from the group consisting of
    (i) hydrogen,
    (ii) hydroxy,
    (iii) $C_{1-8}alkyl$,
    (iv) $C_{1-8}alkoxy$, and
    (v) amino optionally mono or disubstituted with a substituent independently selected from the group consisting of
        (a) $C_{1-8}alkyl$,
        (b) $C_{1-8}alkyl(C_{1-8}alkoxy)$,
        (c) $C_{1-8}alkyl(amino)$ optionally mono or disubstituted on amino with $C_{1-8}alkyl$,
        (d) $C_{1-8}alkyl(hydroxy)_{1-3}$, (e) $C_{3-8}$cycloalkyl, and
(f) aryl, and
(13) $SO_2$(amino), wherein amino is optionally mono or disubstituted with a substituent independently selected from the group consisting of
(i) $C_{1-8}$alkyl,
(ii) $C_{1-8}$alkyl($C_{1-8}$alkoxy),
(iii) $C_{1-8}$alkyl(amino) optionally mono or disubstituted on amino with $C_{1-8}$alkyl,
(iv) $C_{1-8}$alkyl(hydroxy)$_{1-3}$,
(v) $C_{3-8}$cycloalkyl, and
(vi) aryl,
$Ar^2$ is aryl, optionally substituted with from one to three substituents independently selected from the group consisting of
(1) $C_{1-8}$alkyl,
(2) $C_{2-8}$alkenyl,
(3) $C_{2-8}$alkynyl,
(4) $C_{1-8}$alkoxy,
wherein (1), (2), (3) and (4) are optionally substituted with from one to three substituents independently selected from the group consisting of
(i) $C_{1-8}$alkoxy,
(ii) cyano,
(iii) halogen,
(iv) hydroxy,
(v) $C_{3-8}$cycloalkyl, and
(vi) aryl,
wherein (v) and (vi) are optionally substituted with from one to three substituents independently selected from the group consisting of
(a) $C_{1-8}$alkyl,
(b) $C_{1-8}$alkoxy,
(c) $C_{1-8}$alkyl($C_{1-8}$alkoxy),
(d) amino optionally mono or disubstituted with $C_{1-8}$alkyl,
(e) cyano,
(f) halogen,
(g) $C_{1-8}$alkyl(halogen)$_{1-3}$,
(h) hydroxy,
(i) $C_{1-8}$alkyl(hydroxy)$_{1-3}$, and
(j) $C_{3-8}$cycloalkyl, and
(5) amino optionally mono or disubstituted with a substituent independently selected from the group consisting of
(i) $C_{1-8}$alkyl,
(ii) $C_{1-8}$alkyl($C_{1-8}$alkoxy),
(iii) $C_{1-8}$alkyl(amino) optionally mono or disubstituted on amino with $C_{1-8}$alkyl,
(iv) $C_{1-8}$alkyl(hydroxy)$_{1-3}$, and
(v) $C_{3-8}$cycloalkyl,
(6) oxy substituted with a substituent selected from the group consisting of
(i) $C_{3-8}$cycloalkyl, and
(ii) aryl,
(7) C(O) substituted with a substituent independently selected from the group consisting of
(i) hydrogen,
(ii) $C_{1-8}$alkyl optionally substituted with from one to three substituents independently selected from the group consisting of
(a) cyano,
(b) halogen, and
(c) hydroxy,
(iii) $C_{1-8}$alkoxy,
(iv) hydroxyl, and
(v) $C_{1-8}$alkoxy($C_{1-8}$alkoxy),
(8) cyano,
(9) halogen,
(10) hydroxy,
(11) nitro,
(12) $C_{3-8}$cycloalkyl, and
(13) aryl.

2. The compound of claim 1, wherein $L^1$ is selected from the group consisting of $N(R_1)$, wherein $R_1$ is selected from the group consisting of hydrogen, $C_{1-8}$alkyl and $C_{1-8}$alkyl($C_{1-8}$alkoxy).

3. The compound of claim 1, wherein $L^1$ is NH.

4. The compound of claim 1, wherein p is 0, 1, 2 or 3.

5. The compound of claim 1, wherein $L^2$ is selected from the group consisting of O, S and $N(R_1)$.

6. The compound of claim 1, wherein $L^2$ is selected from the group consisting of O, S and NH.

7. The compound of claim 1, wherein $Ar^1$ is aryl, optionally substituted with from one to three substituents independently selected from the group consisting of
(1) $C_{1-8}$alkyl,
(2) $C_{1-8}$alkoxy,
wherein (1) and (2) are optionally substituted with one to three substituents independently selected from the group consisting of
(i) $C_{3-8}$cycloalkyl,
(ii) aryl,
wherein (i) and (ii) are optionally substituted with from one to three substituents independently selected from the group consisting of
(a) $C_{1-8}$alkyl,
(b) $C_{1-8}$alkoxy,
(c) $C_{1-8}$alkyl($C_{1-8}$alkoxy),
(d) $C_{1-8}$alkyl(halogen)$_{1-3}$,
(e) $C_{1-8}$alkyl(hydroxy)$_{1-3}$,
(f) amino optionally mono or disubstituted with $C_{1-8}$alkyl,
(g) cyano,
(h) halogen,
(i) hydroxy, and
(j) $C_{1-8}$alkyl(amino) optionally mono or disubstituted on amino with $C_{1-8}$alkyl, and
(v) amino optionally mono or disubstituted with a substituent independently selected from the group consisting of
(a) $C_{1-8}$alkyl,
(b) $C_{1-8}$alkyl($C_{1-8}$alkoxy), and
(3) amino optionally mono or disubstituted with a substituent independently selected from the group consisting of
(i) $C_{1-8}$alkyl, and
(ii) $C_{1-8}$alkyl(amino) optionally mono or disubstituted on amino with $C_{1-8}$alkyl,
(4) halogen,
(5) hydroxy,
(6) $C_{3-8}$cycloalkyl,
(7) aryl, and
(8) $SO_2$(amino), wherein amino is optionally mono or disubstituted with a substituent independently selected from the group consisting of
(i) $C_{1-8}$alkyl,
(ii) $C_{1-8}$alkyl($C_{1-8}$alkoxy),
(iii) $C_{1-8}$alkyl(amino) optionally mono or disubstituted on amino with $C_{1-8}$alkyl,
(iv) $C_{1-8}$alkyl(hydroxy)$_{1-3}$.

8. The compound of claim 1, wherein $Ar^1$ is aryl, optionally substituted with from one to three substituents independently selected from the group consisting of (1) $C_{1-8}$alkyl,
(2) $C_{1-8}$alkoxy,
  wherein (1) and (2) are optionally substituted with one to three substituents independently selected from the group consisting of
  amino optionally mono or disubstituted with a substituent independently selected from the group consisting of
    (a) $C_{1-8}$alkyl, and
    (b) $C_{1-8}$alkyl($C_{1-8}$alkoxy),
(3) amino optionally mono or disubstituted with a substituent independently selected from the group consisting of $C_{1-8}$alkyl(amino),
(4) halogen,
(5) hydroxy,
(6) $SO_2$(amino), wherein amino is optionally mono or disubstituted with a substituent independently selected from the group consisting of
  (i) $C_{1-8}$alkyl($C_{1-8}$alkoxy), and
  (ii) $C_{1-8}$alkyl(amino) optionally mono or disubstituted on amino with $C_{1-8}$alkyl.

9. The compound of claim 1, wherein $Ar^2$ is aryl, optionally substituted with from one to three substituents independently selected from the group consisting of
(1) $C_{1-8}$alkyl,
(2) $C_{2-8}$alkenyl,
(3) $C_{2-8}$alkynyl,
(4) $C_{1-8}$alkoxy,
  wherein (1), (2), (3) and (4) are optionally substituted with from one to three substituents independently selected from the group consisting of
  (i) $C_{1-8}$alkoxy,
  (ii) halogen,
  (iii) hydroxy,
  (iv) aryl optionally substituted with from one to three substituents independently selected from the group consisting of
    (a) $C_{1-8}$alkyl,
    (b) $C_{1-8}$alkoxy,
    (c) $C_{1-8}$alkyl($C_{1-8}$alkoxy),
    (d) amino optionally mono or disubstituted with $C_{1-8}$alkyl,
    (e) halogen,
    (f) $C_{1-8}$alkyl(halogen)$_{1-3}$,
    (g) hydroxy, and
    (h) $C_{1-8}$alkyl(hydroxy)$_{1-3}$, and
  (v) amino optionally mono or disubstituted with $C_{1-8}$alkyl,
(5) amino optionally mono or disubstituted with a substituent independently selected from the group consisting of
  (i) $C_{1-8}$alkyl, and
  (ii) $C_{1-8}$alkyl(amino) optionally mono or disubstituted on amino with $C_{1-8}$alkyl,
(6) oxy substituted with a substituent selected from the group consisting of
  (i) $C_{3-8}$cycloalkyl, and
  (ii) aryl,
(7) cyano,
(8) halogen, and
(9) hydroxy.

10. The compound of claim 1, wherein $Ar^2$ is aryl, optionally substituted with from one to three substituents independently selected from the group consisting of
(1) $C_{2-8}$alkynyl,
(2) $C_{1-8}$alkoxy optionally substituted with from one to three substituents independently selected from the group consisting of
  (i) halogen, and
  (ii) aryl optionally substituted with from one to three halogen substituents, and
(3) halogen.

11. The compound of claim 1, wherein
$L^1$ is NH;
p is 0, 1, 2 or 3;
$L^2$ is selected from the group consisting of O, S and NH;
$Ar^1$ is aryl, optionally substituted with from one to three substituents independently selected from the group consisting of
(1) $C_{1-8}$alkyl,
(2) $C_{1-8}$alkoxy,
  wherein (1) and (2) are optionally substituted with one to three substituents independently selected from the group consisting of
  amino optionally mono or disubstituted with a substituent independently selected from the group consisting of
    (a) $C_{1-8}$alkyl, and
    (b) $C_{1-8}$alkyl($C_{1-8}$alkoxy),
(3) amino optionally mono or disubstituted with a substituent independently selected from the group consisting of
  $C_{1-8}$alkyl(amino)
(4) halogen,
(5) hydroxy,
(6) $SO_2$(amino), wherein amino is optionally mono or disubstituted with a substituent independently selected from the group consisting of
  (i) $C_{1-8}$alkyl($C_{1-8}$alkoxy), and
  (ii) $C_{1-8}$alkyl(amino) optionally mono or disubstituted on amino with $C_{1-8}$alkyl
$Ar^2$ is aryl optionally substituted with from one to three substituents independently selected from the group consisting of
(1), $C_{2-8}$alkynyl,
(2) $C_{1-8}$alkoxy optionally substituted with from one to three substituents independently selected from the group consisting of
  (i) halogen, and
  (ii) aryl optionally substituted with from one to three halogen substituents, and
(3) halogen.

12. A pharmaceutical composition comprising an effective amount of a compound of claim 1 and an inert carrier.

13. The pharmaceutical composition of claim 12, wherein the effective amount of the compound is in a range of from about 0.001 mg to about 5000 mg.

\* \* \* \* \*

UNITED STATES PATENT AND TRADEMARK OFFICE
CERTIFICATE OF CORRECTION

PATENT NO.      : 7,659,284 B2                          Page 1 of 1
APPLICATION NO. : 11/226961
DATED           : February 9, 2010
INVENTOR(S)     : Connolly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 605 days.

Signed and Sealed this

Thirtieth Day of November, 2010

David J. Kappos
*Director of the United States Patent and Trademark Office*